(12) United States Patent
Rozen

(10) Patent No.: US 6,833,243 B2
(45) Date of Patent: Dec. 21, 2004

(54) METHODS FOR SELECTING A THERAPY FOR A SUBJECT SUFFERING FROM SCHIZOPHRENIA

(75) Inventor: Rima Rozen, Montreal West (CA)

(73) Assignee: Nuvelo, Inc., Sunnyvale, CA (US)

( * ) Notice: Subject to any disclaimer, the term of this patent is extended or adjusted under 35 U.S.C. 154(b) by 115 days.

(21) Appl. No.: 09/931,795

(22) Filed: Aug. 16, 2001

(65) Prior Publication Data

US 2002/0198211 A1 Dec. 26, 2002

Related U.S. Application Data

(60) Division of application No. 09/592,595, filed on Jun. 12, 2000, which is a continuation-in-part of application No. 09/258,928, filed on Mar. 1, 1999, now Pat. No. 6,218,120, which is a continuation-in-part of application No. 08/738,000, filed as application No. PCT/CA95/00314 on May 25, 1995, now Pat. No. 6,074,821.

(30) Foreign Application Priority Data

May 26, 1994 (GB) ............................................. 9410620

(51) Int. Cl.⁷ .......................... C12Q 1/68; C07H 21/02; C07H 21/04
(52) U.S. Cl. .......................... 435/6; 536/23.1; 536/23.5; 536/23.7
(58) Field of Search ............................ 435/6; 536/23.1, 536/23.5, 23.7

(56) References Cited

U.S. PATENT DOCUMENTS

| 5,972,614 A | 10/1999 | Ruano et al. ................... 435/6 |
| 6,008,221 A | 12/1999 | Smith et al. ................. 514/254 |

FOREIGN PATENT DOCUMENTS

| WO | WO 95/33054 | 12/1995 |
| WO | WO 99/61014 | 12/1999 |
| WO | WO 00/04194 | 1/2000 |
| WO | WO 00/71754 | 11/2000 |

OTHER PUBLICATIONS

Gussekloo et al. Journal of Neurol Neurosurg Psychiatry. 1999. 67: 535–538.*
Zuliani et al. Acta Neurol Scand. 2001: 304–308.*
Joober et al., "Association Between the Methylenetetrahydrofolate Reductase 677C→T Missense Mutation and Schizophrenia," *Mol. Psychiatry* 5(3):323–326 (2000).
Pereira et al., "Loss of Heterozygosity of Methylenetetrahydrofolate Reductase in Colon Carcinomas," *Oncology Report, National Hellenic Research Foundation, Athens, Gr.*, 6(6):597–599 (1999).
Akar et al., "Effect of methylenetetrahydrofolate reductase 677 C–T, 1298 A–C, and 1317 T–C on factor V 1691 mutation in Turkish deep vein thrombosis patients," *Thromb. Res.* 97:163–167 (2000).
Araki et al., "Determination of free and total homocysteine in human plasma by high–performance liquid chromatography with fluorecence detection," *J. Chromatography* 422:43–52 (1987).
Arinami et al., "Methylenetratrahydrofolate Reductase Variant and Schizophrenia/Depression," *Amer. J. of Medical Genetics* 74:526–528 (1997).
Arranz et al., "Evidence for association between polymorphisms in the promoter and coding regions of the 5–HT$_{2A}$ receptor gene and response to clozapine," *Molecular Psychiatry* 3:61–66 (1998).
Bakker et al., "Hyperhomocysteinaemia and associated disease," *Pharm. World Sci.* 19:126–132 (1997).
Boushey et al., "A quantitative assessment of plasma homocysteine as a risk factor for vascular disease. Probable benefits of increasing folic acid intakes," *JAMA* 274:1049–1057 (1995).
Brattstrom et al., "Plasma homocysteine and methionine tolerance in early–onset vascular disease," *Homeostasis* 19:35–44 (1989).
Breier et al., "National Institute of Mental Health longitudinal study of chronic schizophrenia. Prognosis and predictors of outcome," *Arch. Gen. Psychiatry* 48:239–246 (1991).
Chapman et al., "ACE MTHFR, Factor V Leiden, And APOE Polymorphisms In Patients With Vascular And Alzheimer's Dementia," *Stroke* 29:1401–1404 (1988).
Christensen et al., "Correlation of a Common Mutation in the Methylenetetrahydrofolate Reductase Gene With Plasma Homocysteine in Patients With Premature Coronary Artery Disease," *Arteriosclerosis, Thrombosis, and Vascular Biology* 17:569–573 (1997).
Christensen et al., "Genetic polymorphisms in methylenetetrahydrofolate reductase and methionine synthase, folate levels in red blood cells, and risk of neural tube defects," *Am. J. Med. Genet.* 84:151–157 (1999).
Clarke et al., "Hyperhomocysteinemia: an independent risk factor for vascular disease," *N. Engl. J. Med.* 324:1149–1155 (1991).
Cormack, "Directed mutagenesis using the polymerase chain reaction," *Current Protocols in Molecular Biology* 1:8.5.1–8.5.9, John Wiley & Sons, New York (1995).
Dalman et al., "Obstetric complications and the risk of schizophrenia; a longitudinal study of a national birth cohort,"*Arch. Gen. Psychiatry* 56:234–240 (1999).
Drazen et al., "Treatment of Asthma with Drugs Modifying the Leukotriene Pathway," *N.E. Journal of Medicine* 340:197–206 (1999).
Drazen et al., "Pharmacogenetic association between ALOX5 promoter genotype and the response to anti–asthma treatment," *Nature Genetics* 22:168–170 (1999).

(List continued on next page.)

*Primary Examiner*—Carla J. Myers

(57) ABSTRACT

The invention features methods for diagnosing subjects at risk for or suffering from a disease or disorder, such as a psychosis. Methods are also provided for selecting a preferred therapy for a particular subject or group of subjects.

16 Claims, 24 Drawing Sheets

OTHER PUBLICATIONS

Endicott et al., "The global assessment scale, a procedure for measuring overall severity of psychiatric disturbance," *Arch. Gen. Psychiatry* 33:766–771 (1976).

Engbersen et al., "Thermolabile 5, 10–Methylenetetrahydrofolate Reductase as a Cause of Mild Hyperhomocysteinemia," *Am. J. Hum. Genet.* 56:142–150 (1995).

Fletcher et al., "MTHFR association with arteriosclerotic vascular disease," *Human Genet.* 103:11–21 (1998).

Freeman et al., "Folate–responsive Homocystinuria and Schizophrenia. A defect in Methylation Due to Deficient 5, 10–Methylenetetrahydrofolate Reductase Activity," *N.E. Journal of Medicine* 292:491–496 (1975).

Frosst et al., "A candidate genetic risk factor for vascular disease: a common mutation in methylenetetrahydrofolate reductase," *Nature Genetics* 10:111–113 (1995).

Gallagher et al., "Homocysteine and risk of premature coronary heart disease. Evidence for a common gene mutation," *Circulation* 94:2154–2158 (1996).

Goyette et al., "Gene structure of human and mouse methylenetetrahydrofolate reductase (MTHFR)," *Mammalian Genome* 9:652–656 (1998).

Goyette et al., "Human methylenetetrahydrofolate reductase: isolation of cDNA, mapping and mutation identification," *Nature Genetics* 7:195–200 (1994).

Goyette et al., "Seven Novel Mutations in the Methylenetetrahydrofolate Reductase Gene and Genotype/Phenotype Correlations in Severe Methylenetetrahydrofolate Reductase Deficiency," *Am. J. Hum. Genet.* 56:1052–1059 (1995).

Goyette et al., "Severe and mild mutations in cis for the methylenetetrahydrofolate reductase (MTHFR) gene, and description of five novel mutations in MTHFR," *Am. J. Hum. Genet.* 59:1268–1275 (1996).

Grandone et al., "Factor V Leiden, C>T MTHFR polymorphism and genetic susceptibility to preeclampsia," *Thromb. Haemost.* 77:1052–1054 (1997).

Grandone et al., "Methylenetetrahydrofolate reductase (MTHFR) 677–>C mutation and unexplained early pregancy loss [letter]," *Thrombosis & Haemostasis* 79:1056–1057 (1998).

Grieco, "Homocystinuria: pathogenetic mechanisms," *Am. J. Med. Sci.* 273:120–132 (1977).

Gudnason et al., "C677T (thermolabile alanine/valine) polymorphism in methylenetetrahydrofolate reductase (MTHFR): its frequency and impact on plasma homocysteine concentration in different European populations." *Atherosclerosis* 136:347–354 (1998).

Guenther et al., "The structure and properties of methylenetetrahydrofolate reductase from *Escherichia coli*: a model for the role of folate in ameliorating hyperhomocysteinemia in humans," *Nature Struct. Biol.* 6:359–365 (1999).

Haagsma et al., "Influence of sulphasalazine, methotrexate, and the combination of both on plasma homocysteine concentrations in patients with rheumatoid arthritis," *Ann. Rheum. Dis.* 58:79–84 (1999).

Haworth et al., "Symptomatic and asymptomatic methylenetetrahydrofolate reductase deficiency in two adult brothers," *Am. J. of Medical Genetics* 45:572–576 (1993).

Higgins et al., "NHLBI Family Heart Study: Objectives and Design," *Am. J. Epidemiol.* 143:1219–1228 (1996).

Hol et al., "Molecular genetic analysis of the gene encoding the trifunctional enzyme MTHFD (methylenetetrahydrofolate–dehydrogenase, methylenetetrahydrofolate–cyclohydrolase, formyltetrahydrofolate synthetase) in patients with neural tube defects," *Clin. Genet.* 53:119–125 (1998).

Jacques et al., "Relation Between Folate Status, a Common Mutation in Methylenetetrahydrofolate Reductase, and Plasma Homocysteine Concentrations," *Circulation* 93:7–9 (1996).

James et al., "Abnormal folate metabolism and mutation in the methylenetetrahydrofolate reductase gene may be maternal risk factors for Down syndrome," *Am. J. Clin. Nutr.* 70:495–501 (1999).

Joober et al., "Polyglutamine–containing proteins in schizophrenia," *Mol. Psychiatry* 4:53–57 (1999).

Kane et al., "Clozapine for the treatment–resistant schizophrenic. A double–blind comparison with chlorpromazine," *Arch. Gen. Psychiatry* 45:789–796 (1988).

Kang et al., "Thermolabile methylenetetrahydrofolate reductase: An inherited risk factor for coronary artery disease," *Am. J. Human Genet.* 48:536–545 (1991).

Kluijtmans et al., "Molecular genetic analysis in mild hyperhomocysteinemia: A common mutation in methylenetetrahydrofolate reductase gene is a risk factor for cardiovascular disease," *Am. J. Hum. Genet.* 58:35–41 (1996).

Koreen et al., "Plasma homovanillic acid levels in first–episode schizophrenia. Psychopathology and treatment response," *Arch Gen. Psychiatry* 51:132–138 (1994).

Kulvenhoven et al., "The Role of a Common Variant of the Cholesteryl Esterr Transfer Protein Gene in the Progression of Coronary Atherosclerosis," *N.E. Journal of Medicine* 338:86–93 (1998).

Kunigi et al., "C677T polymorphism in methylenetetrahydrofolate reductase gene and psychoses," *Mol. Psychiatr.* 3:435–437 (1998).

Lanoue et al., "Antisense Inhibition of Methylenetetrahydrofolate Reductase Results in Neural Tube Defects in Cultured Mouse Embryos," *Experimental Biology Abstract* (1997).

Mathews et al., "Methylenetetrahydrofolate reductase and methionine synthase: biochemistry and molecular biology," *Eur. J. Pediatr.* 157:S54–S59 (1998).

Matthews, "Methylenetetrahydrofolate reductase from pig liver," *Methods in Enzymology Vitamines and Coenzymes Part G* 122:372–381 (1986).

Molimard et al., "Does use of withdrawal of long–acting $\beta_2$–adrenoceptor induce desensitisation?," *Lancet* 351: 66–67 (1998).

Morita et al., "Genetic polymorphism of 5,10 methylenetetrahydrofolate reductase (MTHFR) as a risk factor for coronary artery disease," *Circulation* 95:2032–2036 (1997).

Mudd et al., "$N^{5,10}$–Methylenetetrahydrofolate reductase deficiency and schizophrenia: a working hypothesis," *J. Psychiat. Res. 11: 259–262 (1974)*.

Niefind et al., "Amino acid similarity coefficients for protein modeling and sequence alignment derived from main–chain folding angles," *J. Mol. Biol.* 219:481–497 (1991).

Nurnberger et al., "Diagnostic interview for genetic studies. Rationale, unique features, and training. NIMH Genetics Initiative," *Arch. Gen. Psychiatry* 51:849–859, discussion 863–864 (1994).

Orita et al., "Rapid and Sensitive Detection of Point Mutations and DNA Polymorphisms Using the Polymerase Chain Reaction," *Genomics* 5:574–579 (1989).

Pasquier et al., "Methylenetetrahydrofolate reductase deficiency revealed by a neuropathy in a psychotic adult [letter]," *Journal of Neurology, Neurosurgyer & Psychiatry* 57:765–766 (1994).

Poirer et al., "Apolipoprotein E4 allele as a predictor of cholinergic deficits and treatment outcome in Alzheimer disease," *Proc. Natl. Acad. Sci. USA* 92:12260–12264 (1995).

Refsum et al., "Homocysteine and vascular disease," *Annu. Rev. Medicine* 48:31–62 (1998).

Regland et al., "Homocysteinemia and schizophrenia as a case of methylation deficiency," *Journal of Neural Transmission–General Section* 98:143–152 (1994).

Regland et al., "Homocysteinemia is a common feature of schizophrenia," *Journal of Neural Transmission–General Section* 100:165–169 (1995).

Regland et al., "Homozygous thermolabile methylenetetrahydrofolate reductase in schizophrenia–like psychosis," *Journal of Neural Transmission 104:931–941 (1997)*.

Rozen, "Molecular genetics of methylenetetrahydrofolate reductase deficiency," *J. Inher. Metab. Dis.* 19:589–594 (1996).

Saint–Girons et al., "Nucleotide sequence of metF, the *E. coli* structure gene for 5–10 methylene tetrahydrofolate reductase and of its control region," *Nucleic Acids Research* 11:6723–6732 (1983).

Schwartz et al., "Myocardial Infarction In Young Women In Relation To Plasma Total Homocysteine, Folate, And A Common Variant In The Methylenetetrahydrofolate Reductase Gene," *Circulation* 96(2):412–417 (1997).

Selhub et al., "Association between plasma homocysteine concentrations and extra–cranial carotid artery stenosis," *N. Engl. J. Med.* 332:286–291 (1995).

Shin–Buehring et al., "A new enzymatic method for pyridoxal–5–phosphate determination," *J. Inherit. Metab. Disorders* 4:123–124 (1981).

Skibola et al., "Polymorphisms in the methylenetetrahydrofolate reductase gene are associated with susceptibility to acute leukemia in adults," *Proc. Natl. Acad. Sci. USA* 96:12810–12815 (1999).

Smeraldi et al., "Polymorphism within the promoter of the serotonin transporter gene and antidepressant efficacy of fluvoxamine," *Molecular Psychiatry* 3:508–511 (1998).

Sohda et al., "Methylenetetrahydrofolate reductase polymorphism and pre–eclampisa," *J. Med. Genet.* 34:525–526 (1997).

Spire–Vayron de la Moureyre et al., "Genotpyic and phenotypic analysis of the polymorphic thiopurine S–methyltransferase gene (TPMT) in a European population," *British Journal of Pharmacology* 125:879–887 (1998).

Stauffer et al., "Cloning and nucleotide sequence of the *Salmonella typhimurium* LT2 metF gene and its homology with the corresponding sequence of *Escherichia coli,*" *Mol. Gen. Genet.* 212:246–251 (1988).

Szymanski et al., "Gender differences in onset of illness, treatment response, course, and biologic indexes in first–episode schizophrenic patients," *Am. J. Psychiatry* 152:698–703 (1995).

Tan et al., "Association between $\beta_2$ adrenoceptor polymorphism and susceptibility to bronchodilator desensitisation in moderately severe stable asthmatics," *Lancet* 350:995–999 (1997).

Tan et al., "Does use of withdrawal of long–acting $\beta_2$–adrenoceptor induce desensitisation?," *Lancet* 351:995–999 (1997).

Third Wave Technologies, "Third Wave Technologies Launches Third Pharmacogenetic Product. Oligonucleotide Sets and Assay Controls Specific for MTHFR Mutation," *News release* Dec. (1999).

Tsuang et al., "Heterogeneity of schizophrenia. Conceptual models and analytic strategies," *Br. J. Psychiatry* 156:17–26 (1990).

Ueda et al., "ACE (I/D) Genotype as a Predictor of the Magnitude and Duration of the Response to an ACE Inhibitor Drug (Enalaprilat) in Humans," *Circulation* 98:2148–2153 (1998).

van der Put et al., "A Second Common Mutation in the Methylenetetrahydrofolate Reductase Gene: An Additional Risk Factor for Neural–Tube Defects?," *Am. J. Hum. Genet.* 62:1044–1051 (1998).

van der Put et al., "Mutated methylenetetrahydrofolate reductase as a risk factor for spina bifida," *Lancet* 346:1070–1071 (1995).

van Ede et al., "Methotrexate in Rheumatoid Arthritis: An update with Focus on Mechanisms Involved in Toxity", *Seminar in Arthritis and Rheumatism,* 27:277–292 (1998).

Viel et al., "Loss of Heterozygosity at the 5, 10–Methylenetetrahydrofolate Reductase locus in Human Ovarian Carcinomas", *British Journal of Cancer* 75:1105–1110 (1997).

Weisberg et al., "A second Genetic Polymorphism in Methylenetetrahydrofolate Reductase (MTHFR) Associated with Decreased Enzyme Activity," *Molecular Genetics and Metabolism* 64:169–172 (1998).

Whitehead et al., "A genetic defect in 5, 10 methylenetetrahydrofolate reductase in neural tube defects," *Q J Med.* 88:763–766 (1995).

Woerner et al., "Anchoring the BPRS: an aid to improved reliability," *Psychopharmacol. Bull.* 24:112–117 (1988).

Wyatt, "Neuroleptics and the natural course of schizophrenia," *Schizophr. Bull.* 17:325–351 (1991).

Yang et al., "Molecular cloning and nucleotide sequence analysis of the *Saccharomyces cerevisiae RAD1* gene," *Mol. Cell. Biol.* 4:2161–2169 (1984).

Zhou et al., "Purification and Characterization of Methylenetetrahydrofolate Reductase from Human Cadaver Liver," *Biochemical Medicine and Metabolic biology* 43:234–242 (1990).

* cited by examiner

```
         10         20         30         40         50
          :          :          :          :          :
AAT TCC GGA GCC ATG GTG AAC GAA GCC AGA GGA AAC AGC AGC CTC AAC CCC
TTA AGG CCT CGG TAC CAC TTG CTT CGG TCT CCT TTG TCG TCG GAG TTG GGG
Asn Ser Gly Ala Met Val Asn Glu Ala Arg Gly Asn Ser Ser Leu Asn Pro›

60         70         80         90        100
          :          :          :          :          :
TGC TTG GAG GGC AGT GCC AGC AGT GGC AGT GAG AGC TCC AAA GAT AGT TCG
ACG AAC CTC CCG TCA CGG TCG TCA CCG TCA CTC TCG AGG TTT CTA TCA AGC
Cys Leu Glu Gly Ser Ala Ser Ser Gly Ser Glu Ser Ser Lys Asp Ser Ser›

110        120        130        140        150
          :          :          :          :          :
AGA TGT TCC ACC CCG GGC CTG GAC CCT GAG CGG CAT GAG AGA CTC CGG GAG
TCT ACA AGG TGG GGC CCG GAC CTG GGA CTC GCC GTA CTC TCT GAG GCC CTC
Arg Cys Ser Thr Pro Gly Leu Asp Pro Glu Arg His Glu Arg Leu Arg Glu›

160        170        180        190        200
          :          :          :          :          :
AAG ATG AGG CGG CGA TTG GAA TCT GGT GAC AAG TGG TTC TCC CTG GAA TTC
TTC TAC TCC GCC GCT AAC CTT AGA CCA CTG TTC ACC AAG AGG GAC CTT AAG
Lys Met Arg Arg Arg Leu Glu Ser Gly Asp Lys Trp Phe Ser Leu Glu Phe›

210        220        230        240        250
          :          :          :          :          :
TTC CCT CCT CGA ACT GCT GAG GGA GCT GTC AAT CTC ATC TCA AGG TTT GAC
AAG GGA GGA GCT TGA CGA CTC CCT CGA CAG TTA GAG TAG AGT TCC AAA CTG
Phe Pro Pro Arg Thr Ala Glu Gly Ala Val Asn Leu Ile Ser Arg Phe Asp›

260        270        280        290        300
          :          :          :          :          :
CGG ATG GCA GCA GGT GGC CCC CTC TAC ATA GAC GTG ACC TGG CAC CCA GCA
GCC TAC CGT CGT CCA CCG GGG GAG ATG TAT CTG CAC TGG ACC GTG GGT CGT
Arg Met Ala Ala Gly Gly Pro Leu Tyr Ile Asp Val Thr Trp His Pro Ala›

310        320        330        340        350
          :          :          :          :          :
GGT GAC CCT GGC TCA GAC AAG GAG ACC TCC TCC ATG ATG ATC GCC AGC ACC
CCA CTG GGA CCG AGT CTG TTC CTC TGG AGG AGG TAC TAC TAG CGG TCG TGG
Gly Asp Pro Gly Ser Asp Lys Glu Thr Ser Ser Met Met Ile Ala Ser Thr›
```

Fig. 1A

```
      360         370         380         390         400
       :           :           :           :           :
  GCC GTG AAC TAC TGT GGC CTG GAG ACC ATC CTG CAC ATG ACC TGC TGC CGT
  CGG CAC TTG ATG ACA CCG GAC CTC TGG TAG GAC GTG TAC TGG ACG ACG GCA
  Ala Val Asn Tyr Cys Gly Leu Glu Thr Ile Leu His Met Thr Cys Cys Arg, 410         420         430         440         450
       :           :           :           :           :
  CAG CGC CTG GAG GAG ATC ACG GGC CAT CTG CAC AAA GCT AAG CAG CTG GGC
  GTC GCG GAC CTC CTC TAG TGC CCG GTA GAC GTG TTT CGA TTC GTC GAC CCG
  Gln Arg Leu Glu Glu Ile Thr Gly His Leu His Lys Ala Lys Gln Leu Gly, 460         470         480         490         500         510
   :           :           :           :           :           :
  CTG AAG AAC ATC ATG GCG CTG CGG GGA GAC CCA ATA GGT GAC CAG TGG GAA
  GAC TTC TTG TAG TAC CGC GAC GCC CCT CTG GGT TAT CCA CTG GTC ACC CTT
  Leu Lys Asn Ile Met Ala Leu Arg Gly Asp Pro Ile Gly Asp Gln Trp Glu, 520         530         540         550         560
               :           :           :           :           :
  GAG GAG GAG GGA GGC TTC AAC TAC GCA GTG GAC CTG GTG AAG CAC ATC CGA
  CTC CTC CTC CCT CCG AAG TTG ATG CGT CAC CTG GAC CAC TTC GTG TAG GCT
  Glu Glu Glu Gly Gly Phe Asn Tyr Ala Val Asp Leu Val Lys His Ile Arg, 570         580         590         600         610
           :           :           :           :           :
  AGT GAG TTT GGT GAC TAC TTT GAC ATC TGT GTG GCA GGT TAC CCC AAA GGC
  TCA CTC AAA CCA CTG ATG AAA CTG TAG ACA CAC CGT CCA ATG GGG TTT CCG
  Ser Glu Phe Gly Asp Tyr Phe Asp Ile Cys Val Ala Gly Tyr Pro Lys Gly, 620         630         640         650         660
           :           :           :           :           :
  CAC CCC GAA GCA GGG AGC TTT GAG GCT GAC CTG AAG CAC TTG AAG GAG AAG
  GTG GGG CTT CGT CCC TCG AAA CTC CGA CTG GAC TTC GTG AAC TTC CTC TTC
  His Pro Glu Ala Gly Ser Phe Glu Ala Asp Leu Lys His Leu Lys Glu Lys, 670         680         690         700         710
           :           :           :           :           :
  GTG TCT GCG GGA GCC GAT TTC ATC ATC ACG CAG CTT TTC TTT GAG GCT GAC
  CAC AGA CGC CCT CGG CTA AAG TAG TAG TGC GTC GAA AAG AAA CTC CGA CTG
  Val Ser Ala Gly Ala Asp Phe Ile Ile Thr Gln Leu Phe Phe Glu Ala Asp,
```

Fig. 1B

```
      720         730         740         750         760
       x           x           x           x           x
ACA TTC TTC CGC TTT GTG AAG GCA TGC ACC GAC ATG GGC ATC ACT TGC CCC
TGT AAG AAG GCG AAA CAC TTC CGT ACG TGG CTG TAC CCG TAG TGA ACG GGG
Thr Phe Phe Arg Phe Val Lys Ala Cys Thr Asp Met Gly Ile Thr Cys Pro, 770         780         790         800         810
       x           x           x           x           x
ATC GTC CCC GGG ATC TTT CCC ATC CAG GGC TAC CAC TCC CTT CGG CAG CTT
TAG CAG GGG CCC TAG AAA GGG TAG GTC CCG ATG GTG AGG GAA GCC GTC GAA
Ile Val Pro Gly Ile Phe Pro Ile Gln Gly Tyr His Ser Leu Arg Gln Leu, 820         830         840         850         860
       x           x           x           x           x
GTG AAG CTG TCC AAG CTG GAG GTG CCA CAG GAG ATC AAG GAC GTG ATT GAG
CAC TTC GAC AGG TTC GAC CTC CAC GGT GTC CTC TAG TTC CTG CAC TAA CTC
Val Lys Leu Ser Lys Leu Glu Val Pro Gln Glu Ile Lys Asp Val Ile Glu, 870         880         890         900         910
       x           x           x           x           x
CCA ATC AAA GAC AAC GAT GCT GCC ATC CGC AAC TAT GGC ATC GAG CTG GCC
GGT TAG TTT CTG TTG CTA CGA CGG TAG GCG TTG ATA CCG TAG CTC GAC CGG
Pro Ile Lys Asp Asn Asp Ala Ala Ile Arg Asn Tyr Gly Ile Glu Leu Ala, 920         930         940         950         960
       x           x           x           x           x
GTG AGC CTG TGC CAG GAG CTT CTG GCC AGT GGC TTG GTG CCA GGC CTC CAC
CAC TCG GAC ACG GTC CTC GAA GAC CGG TCA CCG AAC CAC GGT CCG GAG GTG
Val Ser Leu Cys Gln Glu Leu Leu Ala Ser Gly Leu Val Pro Gly Leu His, 970         980         990         1000        1010        1020
   x           x           x           x           x           x
TTC TAC ACC CTC AAC CGC GAG ATG GCT ACC ACA GAG GTG CTG AAG CGC CTG
AAG ATG TGG GAG TTG GCG CTC TAC CGA TGG TGT CTC CAC GAC TTC GCG GAC
Phe Tyr Thr Leu Asn Arg Glu Met Ala Thr Thr Glu Val Leu Lys Arg Leu, 1030        1040        1050        1060        1070
               x           x           x           x           x
GGG ATG TGG ACT GAG GAC CCC AGG CGT CCC CTA CCC TGG GCT CTC AGT GCC
CCC TAC ACC TGA CTC CTG GGG TCC GCA GGG GAT GGG ACC CGA GAG TCA CGG
Gly Met Trp Thr Glu Asp Pro Arg Arg Pro Leu Pro Trp Ala Leu Ser Ala,
```

Fig. 1C

```
        1080            1090            1100            1110            1120
     x       x       x       x       x       x       x       x       x       x
CAC CCC AAG CGC CGA GAG GAA GAT GTA CGT CCC ATC TTC TGG GCC TCC AGA
GTG GGG TTC GCG GCT CTC CTT CTA CAT GCA GGG TAG AAG ACC CGG AGG TCT
His Pro Lys Arg Arg Glu Glu Asp Val Arg Pro Ile Phe Trp Ala Ser Arg, 1130            1140            1150            1160            1170
     x       x       x       x       x       x       x       x       x       x
CCA AAG AGT TAC ATC TAC CGT ACC CAG GAG TGG GAC GAG TTC CCT AAC GGC
GGT TTC TCA ATG TAG ATG GCA TGG GTC CTC ACC CTG CTC AAG GGA TTG CCG
Pro Lys Ser Tyr Ile Tyr Arg Thr Gln Glu Trp Asp Glu Phe Pro Asn Gly, 1180            1190            1200            1210            1220
     x       x       x       x       x       x       x       x       x       x
CGC TGG GGC AAT TCC TCT TCC CCT GCC TTT GGG GAG CTG AAG GAC TAC TAC
GCG ACC CCG TTA AGG AGA AGG GGA CGG AAA CCC CTC GAC TTC CTG ATG ATG
Arg Trp Gly Asn Ser Ser Ser Pro Ala Phe Gly Glu Leu Lys Asp Tyr Tyr, 1230            1240            1250            1260            1270
     x       x       x       x       x       x       x       x       x       x
CTC TTC TAC CTG AAG AGC AAG TCC CCC AAG GAG GAG CTG CTG AAG ATG TGG
GAG AAG ATG GAC TTC TCG TTC AGG GGG TTC CTC CTC GAC GAC TTC TAC ACC
Leu Phe Tyr Leu Lys Ser Lys Ser Pro Lys Glu Glu Leu Leu Lys Met Trp, 1280            1290            1300            1310            1320
     x       x       x       x       x       x       x       x       x       x
GGG GAG GAG CTG ACC AGT GAA GCA AGT GTC TTT GAA GTC TTT GTT CTT TAC
CCC CTC CTC GAC TGG TCA CTT CGT TCA CAG AAA CTT CAG AAA CAA GAA ATG
Gly Glu Glu Leu Thr Ser Glu Ala Ser Val Phe Glu Val Phe Val Leu Tyr, 1330            1340            1350            1360            1370
     x       x       x       x       x       x       x       x       x       x
CTC TCG GGA GAA CCA AAC CGG AAT GGT CAC AAA GTG ACT TGC CTG CCC TGG
GAG AGC CCT CTT GGT TTG GCC TTA CCA GTG TTT CAC TGA ACG GAC GGG ACC
Leu Ser Gly Glu Pro Asn Arg Asn Gly His Lys Val Thr Cys Leu Pro Trp, 1380            1390            1400            1410            1420
     x       x       x       x       x       x       x       x       x       x
AAC GAT GAG CCC CTG GCG GCT GAG ACC AGC CTG CTG AAG GAG GAG CTG CTG
TTG CTA CTC GGG GAC CGC CGA CTC TGG TCG GAC GAC TTC CTC CTC GAC GAC
Asn Asp Glu Pro Leu Ala Ala Glu Thr Ser Leu Leu Lys Glu Glu Leu Leu,
```

Fig. 1D

```
1430          1440          1450          1460          1470
  :     :     :     :     :     :     :     :     :     :
CGG GTG AAC CGC CAG GGC ATC CTC ACC ATC AAC TCA CAG CCC AAC ATC AAC
GCC CAC TTG GCG GTC CCG TAG GAG TGG TAG TTG AGT GTC GGG TTG TAG TTG
Arg Val Asn Arg Gln Gly Ile Leu Thr Ile Asn Ser Gln Pro Asn Ile Asn>

1480          1490          1500          1510          1520          1530
  :     :     :     :     :     :     :     :     :     :     :     :
GGG AAG CCG TCC TCC GAC CCC ATC GTG GGC TGG GGC CCC AGC GGG GGC TAT
CCC TTC GGC AGG AGG CTG GGG TAG CAC CCG ACC CCG GGG TCG CCC CCG ATA
Gly Lys Pro Ser Ser Asp Pro Ile Val Gly Trp Gly Pro Ser Gly Gly Tyr>

1540          1550          1560          1570          1580
           :     :     :     :     :     :     :     :     :     :
GTC TTC CAG AAG GCC TAC TTA GAG TTT TTC ACT TCC CGC GAG ACA GCG GAA
CAG AAG GTC TTC CGG ATG AAT CTC AAA AAG TGA AGG GCG CTC TGT CGC CTT
Val Phe Gln Lys Ala Tyr Leu Glu Phe Phe Thr Ser Arg Glu Thr Ala Glu>

1590          1600          1610          1620          1630
  :     :     :     :     :     :     :     :     :     :
GCA CTT CTG CAA GTG CTG AAG AAG TAC GAG CTC CGG GTT AAT TAC CAC CTT
CGT GAA GAC GTT CAC GAC TTC TTC ATG CTC GAG GCC CAA TTA ATG GTG GAA
Ala Leu Leu Gln Val Leu Lys Lys Tyr Glu Leu Arg Val Asn Tyr His Leu>

1640          1650          1660          1670          1680
           :     :     :     :     :     :     :     :     :     :
GTC AAT GTG AAG GGT GAA AAC ATC ACC AAT GCC CCT GAA CTG CAG CCG AAT
CAG TTA CAC TTC CCA CTT TTG TAG TGG TTA CGG GGA CTT GAC GTC GGC TTA
Val Asn Val Lys Gly Glu Asn Ile Thr Asn Ala Pro Glu Leu Gln Pro Asn>

1690          1700          1710          1720          1730
  :     :     :     :     :     :     :     :     :     :
GCT GTC ACT TGG GGC ATC TTC CCT GGG CGA GAG ATC ATC CAG CCC ACC GTA
CGA CAG TGA ACC CCG TAG AAG GGA CCC GCT CTC TAG TAG GTC GGG TGG CAT
Ala Val Thr Trp Gly Ile Phe Pro Gly Arg Glu Ile Ile Gln Pro Thr Val>

1740          1750          1760          1770          1780
  :     :     :     :     :     :     :     :     :     :
GTG GAT CCC GTC AGC TTC ATG TTC TGG AAG GAC GAG GCC TTT GCC CTG TGG
CAC CTA GGG CAG TCG AAG TAC AAG ACC TTC CTG CTC CGG AAA CGG GAC ACC
Val Asp Pro Val Ser Phe Met Phe Trp Lys Asp Glu Ala Phe Ala Leu Trp>
```

Fig. 1E

```
        1790        1800        1810        1820        1830
ATT GAG CGG TGG GGA AAG CTG TAT GAG GAG GAG TCC CCG TCC CGC ACC ATC
TAA CTC GCC ACC CCT TTC GAC ATA CTC CTC CTC AGG GGC AGG GCG TGG TAG
Ile Glu Arg Trp Gly Lys Leu Tyr Glu Glu Glu Ser Pro Ser Arg Thr Ile›

1840        1850        1860        1870        1880
ATC CAG TAC ATC CAC GAC AAC TAC TTC CTG GTC AAC CTG GTG GAC AAT GAC
TAG GTC ATG TAG GTG CTG TTG ATG AAG GAC CAG TTG GAC CAC CTG TTA CTG
Ile Gln Tyr Ile His Asp Asn Tyr Phe Leu Val Asn Leu Val Asp Asn Asp›

1890        1900        1910        1920        1930
TTC CCA CTG GAC AAC TGC CTC TGG CAG GTG GTG GAA GAC ACA TTG GAG CTT
AAG GGT GAC CTG TTG ACG GAG ACC GTC CAC CAC CTT CTG TGT AAC CTC GAA
Phe Pro Leu Asp Asn Cys Leu Trp Gln Val Val Glu Asp Thr Leu Glu Leu›

1940        1950        1960        1970        1980        1990
CTC AAC AGG CCC ACC CAG AAT GCG AGA GAA ACG GAG GCT CCA TGACCCTGCG
GAG TTG TCC GGG TGG GTC TTA CGC TCT CTT TGC CTC CGA GGT ACTGGGACGC
Leu Asn Arg Pro Thr Gln Asn Ala Arg Glu Thr Glu Ala Pro›

2000        2010        2020        2030        2040        2050
TCCTGACGCC CTGCGTTGGA GCCACTCCTG TCCCGCCTTC CTCCTCCACA GTGCTGCTTC
AGGACTGCGG GACGCAACCT CGGTGAGGAC AGGGCGGAAG GAGGAGGTGT CACGACGAAG 2060        2070        2080        2090        2100        2110
TCTTGGGAAC TCCACTCTCC TTCGTGTCTC TCCCACCCCG GCCTCCACTC CCCCACCTGA
AGAACCCTTG AGGTGAGAGG AAGCACAGAG AGGGTGGGGC CGGAGGTGAG GGGGTGGACT 2120        2130        2140        2150        2160        2170
CAATGGCAGC TAGACTGGAG TGAGGCTTCC AGGCTCTTCC TGGACCTGAG TCGGCCCCAC
GTTACCGTCG ATCTGACCTC ACTCCGAAGG TCCGAGAAGG ACCTGGACTC AGCCGGGGTG 2180        2190        2200        2210        2220
ATGGGAACCT AGTACTCTCT GCTCTAAAAA AAAAAAAAAA AAAGGAATTC
TACCCTTGGA TCATGAGAGA CGAGATTTTT TTTTTTTTTT TTTCCTTAAG
```

Fig. 1F

```
                                                                 100·
AMVNE  ARGNS  SLNPC  LEGSA  SSGSE  SSKDS  SRCST  PGLDP  ERHER  LREKM  RRRLE  S--GDKW  FSLEF   mthfr
                                                   ms  ffHas  qRdal  ngsLa  evqGqin  vSFEF   ecometf
                                                   ms  ffHan  qREal  ngsLa  evqGqin  vSFEF   stymetf
                                                                 ms  iRdLy  haraspf  iSLEF   ysRAD1

100·
FPPRT  AEGAV  NLISR  FDRMA  AGGPL  YIDVT  WHPAG  DPGSD  KETSS  MMIAS  TAVNY  CGLET  ILHMT    mthfr
FPPRT  sEmeq  tLwns  iDRls  slkPk  fvsVT  y--ga  nsGer  drThs  i-Ikg  ik-dr  tGLEa  apHlT    ecometf
FPPRT  sEmeq  tLwns  iDRls  slkPk  fvsVT  y--ga  nsGer  drThs  v-Ikg  ik-er  tGLEa  apHlT    stymetf
FPPkT  elGtr  NLmeR  mhRMt  AldPL  fltVT  W--ga  -gGtt  aEktl  t-lAS  lAqqt  lnipv  cmHlT    ysRAD1
                                    *                                    *
CCRQR  LEEIT  GHLHK  AKQLG  LKNIM  ALRGD  -PIGDQ  WEEEE  GGFNY  AVGLV  KHIRS  EFGDY  FDICV   mthfr
Cidat  pdElr  tiard  ywnnG  irhIv  ALRGD  lPpGsg  kpE--  ---mY  AsdLV  tllk-  EvaD-  FDIsV   ecometf
Cidat  rdElr  tiard  ywnnG  irhIv  ALRGD  lPpGsg  kpE--  ---mY  AadLV  gllk-  EvaD-  FDIsV   stymetf
Ctnte  kalId  daLdr  cynaG  irNIl  ALRGn  lPIGvv  Wlvsq  snrll  nmrLf>                       ysRAD1
 200·
AGYPK  GHPEA  GSFEA  DLKHL  KEKVS  AGADF  IITQL  FFEAD  TFFRF  VKACT  DMGIT  CPIVP  GIFPI    mthfr
AaYPe  vHPEA  kSaqA  DLlnL  KrKVd  AGAnr  aITQf  FFdve  sylRF  rdrCv  saGId  velIP  GIlPv    ecometf
AaYPe  vHPEA  kSaqA  DLlnL  KrKVd  AGAnr  aITQf  FFdve  sylRF  rdrCv  saGId  velIP  GIlPv    stymetf
                                                   300·
QGYHS  LRQLV  KLSKL  EVPQE  IKDVI  EPIKD  NDAAI  RN-YGI  ELAVS  LCQEL  LASGL  VPGLH  FYTLN   mthfr
snfkq  akkfa  dmtnv  riPaw  maqmf  dgl-D  dDAet  RklvGa  niAmd  mvkiL  sreG-  VkdfH  FYTLN   ecometf
snfkq  akkfa  dmtnv  riPsw  mslmf  Egl-D  nDAet  RklvGa  niAmd  mvkiL  sreG-  VkdfH  FYTLN   stymetf R-EMAT  TEVLK  RLGMW  TEDPR  RPLPW  ALSAH  PKRRE  EDVRP  IFWAS  RPKSY  IYRTD  EWDEF  PNGRW  mthfr
RaEMsy  a-ich  tLGvr  pgl>                                                                ecometf
RaEMsy  a-ich  tLGvr  pgl>                                                                stymetf
      400·
GNSSS  PAFGE  LKDYY  LFYLK  SKSPK  E   mthfr
```

```
AAT TCC GGA GCC ATG GTG AAC GAA GCC AGA GGA AAC AGC AGC CTC AAC CCC TGC TTG GAG    60
                Met Val Asn Glu Ala Arg Gly Asn Ser Ser Leu Asn Pro Cys Leu Glu    16

GGC AGT GCC AGC AGT GGC AGT GAG AGC TCC AAA GAT AGT TCG AGA TGT TCC ACC CCG GGC   120
Gly Ser Ala Ser Ser Gly Ser Glu Ser Ser Lys Asp Ser Ser Arg Cys Ser Thr Pro Gly    36

CTG GAC CCT GAG CGG CAT GAG AGA CTC CGG GAG AAG ATG AGG CGG CGA TTG GAA TCT GGT   180
Leu Asp Pro Glu Arg His Glu Arg Leu Arg Glu Lys Met Arg Arg Arg Leu Glu Ser Gly    56

GAC AAG TGG TTC TCC CTG GAA TTC TTC CCT CCT CGA ACT GCT GAG GGA GCT GTC AAT CTC   240
Asp Lys Trp Phe Ser Leu Glu Phe Phe Pro Pro Arg Thr Ala Glu Gly Ala Val Asn Leu    76

ATC TCA AGG TTT GAC CGG ATG GCA GCA GGT GGC CCC CTC TAC ATA GAC GTG ACC TGG CAC   300
Ile Ser Arg Phe Asp Arg Met Ala Ala Gly Gly Pro Leu Tyr Ile Asp Val Thr Trp His    96

CCA GCA GGT GAC CCT GGC TCA GAC AAG GAG ACC TCC TCC ATG ATG ATC GCC AGC ACC GCC   360
Pro Ala Gly Asp Pro Gly Ser Asp Lys Glu Thr Ser Ser Met Met Ile Ala Ser Thr Ala   116

GTG AAC TAC TGT GGC CTG GAG ACC ATC CTG CAC ATG ACC TGC TGC CGT CAG CGC CTG GAG   420
Val Asn Tyr Cys Gly Leu Glu Thr Ile Leu His Met Thr Cys Cys Arg Gln Arg Leu Glu   136

GAG ATC ACG GGC CAT CTG CAC AAA GCT AAG CAG CTG GGC CTG AAG AAC ATC ATG GCG CTG   480
Glu Ile Thr Gly His Leu His Lys Ala Lys Gln Leu Gly Leu Lys Asn Ile Met Ala Leu   156

CGG GGA GAC CCA ATA GGT GAC CAG TGG GAA GAG GAG GAG GGA GGC TTC AAC TAC GCA GTG   540
Arg Gly Asp Pro Ile Gly Asp Gln Trp Glu Glu Glu Glu Gly Gly Phe Asn Tyr Ala Val   176

GAC CTG GTG AAG CAC ATC CGA AGT GAG TTT GGT GAC TAC TTT GAC ATC TGT GTG GCA GGT   600
Asp Leu Val Lys His Ile Arg Ser Glu Phe Gly Asp Tyr Phe Asp Ile Cys Val Ala Gly   196

TAC CCC AAA GGC CAC CCC GAA GCA GGG AGC TTT GAG GCT GAC CTG AAG CAC TTG AAG GAG   660
Tyr Pro Lys Gly His Pro Glu Ala Gly Ser Phe Glu Ala Asp Leu Lys His Leu Lys Glu   216

AAG GTG TCT GCG GGA GCC GAT TTC ATC ATC ACG CAG CTT TTC TTT GAG GCT GAC ACA TTC   720
Lys Val Ser Ala Gly Ala Asp Phe Ile Ile Thr Gln Leu Phe Phe Glu Ala Asp Thr Phe   236
```

Fig. 6A

```
TTC CGC TTT GTG AAG GCA TGC ACC GAC ATG GGC ATC ACT TGC CCC ATC GTC CCC GGG ATC   780
Phe Arg Phe Val Lys Ala Cys Thr Asp Met Gly Ile Thr Cys Pro Ile Val Pro Gly Ile   256

TTT CCC ATC CAG GGC TAC CAC TCC CTT CGG CAG CTT GTG AAG CTG TCC AAG CTG GAG GTG   840
Phe Pro Ile Gln Gly Tyr His Ser Leu Arg Gln Leu Val Lys Leu Ser Lys Leu Glu Val   276

CCA CAG GAG ATC AAG GAC GTG ATT GAG CCA ATC AAA GAC AAC GAT GCT GCC ATC CGC AAC   900
Pro Gln Glu Ile Lys Asp Val Ile Glu Pro Ile Lys Asp Asn Asp Ala Ala Ile Arg Asn   296

TAT GGC ATC GAG CTG GCC GTG AGC CTG TGC CAG GAG CTT CTG GCC AGT GGC TTG GTG CCA   960
Tyr Gly Ile Glu Leu Ala Val Ser Leu Cys Gln Glu Leu Leu Ala Ser Gly Leu Val Pro   316

GGC CTC CAC TTC TAC ACC CTC AAC CGC GAG ATG GCT ACC ACA GAG GTG CTG AAG CGC CTG  1020
Gly Leu His Phe Tyr Thr Leu Asn Arg Glu Met Ala Thr Thr Glu Val Leu Lys Arg Leu   336

GGG ATG TGG ACT GAG GAC CCC AGG CGT CCC CTA CCC TGG GCT CTC AGT GCC CAC CCC AAG  1080
Gly Met Trp Thr Glu Asp Pro Arg Arg Pro Leu Pro Trp Ala Leu Ser Ala His Pro Lys   356

CGC CGA GAG GAA GAT GTA CGT CCC ATC TTC TGG GCC TCC AGA CCA AAG AGT TAC ATC TAC  1140
Arg Arg Glu Glu Asp Val Arg Pro Ile Phe Trp Ala Ser Arg Pro Lys Ser Tyr Ile Tyr   376

CGT ACC CAG GAG TGG GAC GAG TTC CCT AAC GGC CGC TGG GGC AAT TCC TCT TCC CCT GCC  1200
Arg Thr Gln Glu Trp Asp Glu Phe Pro Asn Gly Arg Trp Gly Asn Ser Ser Ser Pro Ala   396

TTT GGG GAG CTG AAG GAC TAC TAC CTC TTC TAC CTG AAG AGC AAG TCC CCC AAG GAG GAG  1260
Phe Gly Glu Leu Lys Asp Tyr Tyr Leu Phe Tyr Leu Lys Ser Lys Ser Pro Lys Glu Glu   416

CTG CTG AAG ATG TGG GGG GAG GAG CTG ACC AGT GAA GCA AGT GTC TTT GAA GTC TTT GTT  1320
Leu Leu Lys Met Trp Gly Glu Glu Leu Thr Ser Glu Ala Ser Val Phe Glu Val Phe Val   436

CTT TAC CTC TCG GGA GAA CCA AAC CGG AAT GGT CAC AAA GTG ACT TGC CTG CCC TGG AAC  1380
Leu Tyr Leu Ser Gly Glu Pro Asn Arg Asn Gly His Lys Val Thr Cys Leu Pro Trp Asn   456

GAT GAG CCC CTG GCG GCT GAG ACC AGC CTG CTG AAG GAG GAG CTG CTG CGG GTG AAC CGC  1440
Asp Glu Pro Leu Ala Ala Glu Thr Ser Leu Leu Lys Glu Glu Leu Leu Arg Val Asn Arg   476
```

Fig. 6B

```
CAG GGC ATC CTC ACC ATC AAC TCA CAG CCC AAC ATC AAC GGG AAG CCG TCC TCC GAC CCC  1500
Gln Gly Ile Leu Thr Ile Asn Ser Gln Pro Asn Ile Asn Gly Lys Pro Ser Ser Asp Pro   496

ATC GTG GGC TGG GGC CCC AGC GGG GGC TAT GTC TTC CAG AAG GCC TAC TTA GAG TTT TTC  1560
Ile Val Gly Trp Gly Pro Ser Gly Gly Tyr Val Phe Gln Lys Ala Tyr Leu Glu Phe Phe   516

ACT TCC CGC GAG ACA GCG GAA GCA CTT CTG CAA GTG CTG AAG AAG TAC GAG CTC CGG GTT  1620
Thr Ser Arg Glu Thr Ala Glu Ala Leu Leu Gln Val Leu Lys Lys Tyr Glu Leu Arg Val   536

AAT TAC CAC CTT GTC AAT GTG AAG GGT GAA AAC ATC ACC AAT GCC CCT GAA CTG CAG CCG  1680
Asn Tyr His Leu Val Asn Val Lys Gly Glu Asn Ile Thr Asn Ala Pro Glu Leu Gln Pro   556

AAT GCT GTC ACT TGG GGC ATC TTC CCT GGG CGA GAG ATC ATC CAG CCC ACC GTA GTG GAT  1740
Asn Ala Val Thr Trp Gly Ile Phe Pro Gly Arg Glu Ile Ile Gln Pro Thr Val Val Asp   576

CCC GTC AGC TTC ATG TTC TGG AAG GAC GAG GCC TTT GCC CTG TGG ATT GAG CGG TGG GGA  1800
Pro Val Ser Phe Met Phe Trp Lys Asp Glu Ala Phe Ala Leu Trp Ile Glu Arg Trp Gly   596

AAG CTG TAT GAG GAG GAG TCC CCG TCC CGC ACC ATC ATC CAG TAC ATC CAC GAC AAC TAC  1860
Lys Leu Tyr Glu Glu Glu Ser Pro Ser Arg Thr Ile Ile Gln Tyr Ile His Asp Asn Tyr   616

TTC CTG GTC AAC CTG GTG GAC AAT GAC TTC CCA CTG GAC AAC TGC CTC TGG CAG GTG GTG  1920
Phe Leu Val Asn Leu Val Asp Asn Asp Phe Pro Leu Asp Asn Cys Leu Trp Gln Val Val   636

GAA GAC ACA TTG GAG CTT CTC AAC AGG CCC ACC CAG AAT GCG AGA GAA ACG GAG GCT CCA  1980
Glu Asp Thr Leu Glu Leu Leu Asn Arg Pro Thr Gln Asn Ala Arg Glu Thr Glu Ala Pro   656

TGA CCC TGC GTC CTG ACG CCC TGC GTT GGA GCC ACT CCT GTC CCG CCT TCC TCC TCC ACA  2040
End

GTG CTG CTT CTC TTG GGA ACT CCA CTC TCC TTC GTG TCT CTC CCA CCC CGG CCT CCA CTC  2100

CCC CAC CTG ACA ATG GCA GCT AGA CTG GAG TGA GGC TTC CAG GCT CTT CCT GGA CCT GAG  2160

TCG GCC CCA CAT GGG AAC CTA GTA CTC TCT GCT CTA AAA AAA AAA AAA AAA AAG GAA TT   2220
```

Fig. 6C

```
MTHFR:    KHLKEKVSAGADFIITQLFFEADTFFR
          |||  |·     | |  ||·||||
DHFR:     GHLKLFVT----R-IMQD-FESDTFFP
```

EXON 1: 246 bp    (bp 3-248)
                                                                    *
gggtgtggct gcctgccccc tgatgctccc tgccccaccc tgtgcagtag GAACCCAGCC
ATGGTGAACG AAGCCAGAGG AAACAGCAGC CTCAACCCCT GCTTGGAGGG CAGTGCCAGC
AGTGGCAGTG AGAGCTCCAA AGATAGTTCG AGATGTTCCA CCCCGGGCCT GGACCCTGAG
CGGCATGAGA GACTCCGGGA GAAGATGAGG CGGCGATTGG AATCTGGTGA CAAGTGGTTC
TCCCTGGAAT TCTTCCCTCC TCGAACTGCT GAGGGAGCTG TCAATCTCAT CTCAAGgtaa
actcatgcaa ggttaaggtg agaggcggga gtggtggtgc ctgggg EXON 2: 239 bp    (bp 249-487)

acggatgg tatttctcct ggaacctctc ttcagaaaca aaccccctacag GTTTGACCGG
ATGGCAGCAG GTGGCCCCCT CTACATAGAC GTGACCTGGC ACCCAGCAGG TGACCCTGGC
TCAGACAAGG AGACCTCCTC CATGATGATC GCCAGCACCG CCGTGAACTA CTGTGGCCTG
GAGACCATCC TGCACATGAC CTGCTGCCGT CAGCGCCTGG AGGAGATCAC GGGCCATCTG
CACAAAGCTA AGCAGCTGGG CCTGAAGAAC ATCATGGCGC TGCGGGGAGg tgtggagcca
gcactcccct acactctggg ttctggcttt cccggaggc EXON 3: 111 bp    (bp 488-598)

tctggaggtt gggtgagacc cagtgactat gacctccacc aaccctgcag ACCCAATAGG
TGACCAGTGG GAAGAGGAGG AGGGAGGCTT CAACTACGCA GTGGACCTGG TGAAGCACAT
CCGAAGTGAG TTTGGTGACT ACTTTGACAT CTGTGTGGCA Ggtgagtggc tggatcatcc
tggtggcggg gatggagcta gggaggctga EXON 4: 194 bp    (bp 599-792)
ccttgaacag gtggaggcca gcctctcctg actgtcatcc ctattggcag GTTACCCCAA
AGGCCACCCC GAAGCAGGGA GCTTTGAGGC TGACCTGAAG CACTTGAAGG AGAAGGTGTC
TGCGGGAGCC GATTTCATCA TCACGCAGCT TTTCTTTGAG GCTGACACAT TCTTCCGCTT
TGTGAAGGCA TGCACCGACA TGGGCATCAC TTGCCCCATC GTCCCCGGGA TCTTTCCCAT
CCAGgtgagg ggcccaggag agcccataag ctccctccac cccactctca ccgc EXON 5: 251 bp    (bp 793-1043)

gctggccagc agccgccaca gcccctcatg tcttggacag GGCTACCACT CCCTTCGGCA
GCTTGTGAAG CTGTCCAAGC TGGAGGTGCC ACAGGAGATC AAGGACGTGA TTGAGCCAAT
CAAAGACAAC GATGCTGCCA TCCGCAACTA TGGCATCGAG CTGGCCGTGA GCCTGTGCCA
GGAGCTTCTG GCCAGTGGCT TGGTGCCAGG CCTCCACTTC TACACCCTCA ACCGCGAGAT
GGCTACCACA GAGGTGCTGA AGCCTGGG GATGTGGACT GAGGACCCCA Ggtgagggca
gtggcccaga gatccccaga ggagggtcca agagcagccc c EXON 6: 135 bp    (bp 1044-1178)

tccctctagc caatcccttg tctcaattct ctgtccccat cctcacccag GCGTCCCCTA
CCCTGGGCTC TCAGTGCCCA CCCCAAGCGC CGAGAGGAAG ATGTACGTCC CATCTTCTGG
GCCTCCAGAC CAAAGAGTTA CATCTACCGT ACCCAGGAGT GGGACGAGTT CCCTAACGGC
CGCTGgtgag ggcctgcaga ccttccttgc aaatacatct tgttcttgg gagcg

Fig.12A

EXON 7: 181 bp          (bp 1179-1359)

actgccctct gtcaggagtg tgccctgacc tctgggcacc cctctgccag GGGCAATTCC
TCTTCCCCTG CCTTTGGGGA GCTGAAGGAC TACTACCTCT TCTACCTGAA GAGCAAGTCC
CCCAAGGAGG AGCTGCTGAA GATGTGGGGG GAGGAGCTGA CCAGTGAAGC AAGTGTCTTT
GAAGTCTTTG TTCTTTACCT CTCGGGAGAA CCAAACCGGA ATGGTCACAA Agtgagtgat
gctggaagtg gggaccctgg ttcatcccct gccctggcc t EXON 8: 183 bp          (bp 1360-1542)

cagggtgcca aacctgatgg tcgccccagc cagctcaccg tctctcccag GTGACTTGCC
TGCCCTGGAA CGATGAGCCC CTGGCGGCTG AGACCAGCCT GCTGAAGGAG GAGCTGCTGC
GGGTGAACCG CCAGGGCATC CTCACCATCA ACTCACAGCC CAACATCAAC GGGAAGCCGT
CCTCCGACCC CATCGTGGGC TGGGGCCCCA GCGGGGGCTA TGTCTTCCAG AAGgtgtggt
agggaggcac ggggtgcccc cctctcttga ccggcacccg tgg EXON 9: 102 bp          (bp 1543-1644)

gggcgtctgg cagggctggg gttggtgaca ggcacctgtc tctcccacag GCCTACTTAG
AGTTTTTCAC TTCCCGCGAG ACAGCGGAAG CACTTCTGCA AGTGCTGAAG AAGTACGAGC
TCCGGGTTAA TTACCACCTT GTCAATGTGA AGgtaggcca ggccccacgg ttcccacaga
gtaccaggcc cttcgttgaa ca EXON 10: 120 bp         (bp 1645-1764)

actccagttg ttcttggccc aggtcttacc cccacccac atccctcag GGTGAAAACA
TCACCAATGC CCCTGAACTG CAGCCGAATG CTGTCACTTG GGGCATCTTC CCTGGGCGAG
AGATCATCCA GCCCACCGTA GTGGATCCCG TCAGCTTCAT GTTCTGGAAG gtaaaggagc
gggggcaagc ttgccccgcc cacctggaaa accgtgggga EXON 11: 219 bp (stop codon)    (bp 1765-1983)
        432 bp (end of cDNA)    (bp 1765-2196)

ctctgtgtgt gtgtgcatgt gtgcgtgtgt gcggggtat gtgtgtgtag GACGAGGCCT
TTGCCCTGTG GATTGAGCGG TGGGGAAAGC TGTATGAGGA GGAGTCCCCG TCCCGCACCA
TCATCCAGTA CATCCACGAC AACTACTTCC TGGTCAACCT GGTGGACAAT GACTTCCCAC
TGGACAACTG CCTCTGGCAG GTGGTGGAAG ACACATTGGA GCTTCTCAAC AGGCCCACCC
AGAATGCGAG AGAAACGGAG GCTCCATGAC CCTGCGTCCT GACGCCCTGC GTTGGAGCCA
CTCCTGTCCC GCCTTCCTCC TCCACAGTGC TGCTTCTCTT GGGAACTCCA CTCTCCTTCG
TGTCTCTCCC ACCCCGGCCT CCACTCCCCC ACCTGACAAT GGCAGCTAGA CTGGAGTGAG
GCTTCCAGGC TCTTCCTGGA CCTGAGTCGG CCCCACATGG GAACCTAGTA CTCTCTGCTC
TAgccaggag tctgtgctct tttggtgggg agcacttgct cctgcagagg ac

Fig.12B

EXON 1: 243 bp        (bp 3-245)
                                                              *
gggtttggta ccagccctat aataccccg gcccccaccc tctacagcag GAATCCAGCC
ATGGTGAACG AGGCCAGAGG AAGTGGCAGT CCCAACCCGC GATCTGAGGG CAGCAGCAGT
GGCAGCGAGA GTTCCAAGGA CAGTTCAAGA TGTTCCACCC CCAGCCTGGA CCCAGAGCGG
CACGAGAGAC TCCGGGAGAA GATGAGGCGC AGAATGGACT CTGGTGACAA GTGGTTCTCC
CTGGAGTTCT TCCCCCCTCG AACTGCTGAG GGAGCTGTTA ACCTCATCTC CAGgtgagta
gggaggttaa tccgcggggg tcggcaggct tcaggggagc gtg EXON 2: 239 bp        (bp 246-484)

gagctcccta tttaccccag gagcctactt aaggaggaaa tccctacag GTTTGACCGG
ATGGCAGCAG GGGGCCCCCT CTTCGTAGAT GTTACCTGGC ACCCAGCTGG AGACCCTGGC
TCAGACAAGG AGACCTCCTC CATGATGATC GCCAGCACAG CAGTAAACTA CTGCGGCTTG
GAAACCATCC TGCATATGAC CTGCTGCCAG CAGCGCCCGG AGGAGATCAC AGGCCATCTG
CACAGAGCCA AGCAGCTGGG CCTGAAGAAC ATAATGGCGC TGAGGGGAGg tgtggcgcca
gcacccctcc tctttgggtt cttgctttcc tgaaggctt EXON 3: 111 bp        (bp 485-595)

tctggaggtc aggggacacc cagtgaccat gacctccagc aaccctgcag ACCCTGTAGG
TGACCACTGG GAAGCAGAGG AAGGAGGCTT CAGCTATGCC ACAGACCTGG TGAAGCACAT
CCGGACCGAG TTTGCTGACT ATTTTGACAT CTGTGTGGCA Ggtaagtgag gacagagaag
ggtcaggatg agaggatagc cagctagtct t EXON 4: 194 bp        (bp 596-789)

gcaggtaggt tgagaccagc cccctactc ttcttgtctc ctcctggtag GTTACCCCAG
AGGCCACCCC GATGCAGAGA GCTTCGAGGA TGACCTGAAG CATTTGAAGG AGAAGGTATC
TGCAGGCGCC GACTTCATTA TCACTCAGCT CTTCTTTGAG GCCAGCACCT TCTTCAGCTT
TGTGAAGGCC TGCACAGAGA TAGGCATCTC TTGCCCTATC CTGCCTGGGA TCTTCCCTAT
TCAGgtgagg ggcttgggag gacctgattc cctccgtcca gtgcatgcgg aagt EXON 5: 251 bp        (bp 790-1040)

cagtggagca taggccagag atgaccccat gccccttgtg tctctgacag GGCTACACTT
CCCTTCGGCA GCTTGTAAAA CTGTCCAAGC TGGAGGTGCC ACAGAAGATC AAGGATGTAA
TTGAGCCCAT CAAAGACAAC GATGCTGCCA TCCGCAACTA CGGCATTGAG CTGGCTGTAA
GGCTGTGCCG GGAGCTGCTG GACAGTGGCT TGGTGCCAGG CCTCCACTTC TATACCCTCA
ACCGCGAGGT GGCCACCATG GAGGTGCTAA AGCAACTGGG CATGTGGACC GAGGACCCCA
Ggtgagcggt ggdagctgga ggcataccca tgagtcagag tcgcgcaggt g EXON 6: 135 bp        (bp 1041-1175)

ctagctcagt ctacctaagc ccttgtcttt tccctcttcc ttccctccag GCGTCCCTTG
CCCTGGGCTC TCAGTGCGCA TCCCAAGCGC CGGGAGGAAG ATGTCCGTCC CATCTTCTGG
GCCTCCAGAC CAAAGAGCTA CATCTACCGC ACACAGGACT GGGATGAGTT TCCTAACGGC
CGCTGgtgag gagagaagcc agggggtgtt aggaattgct ggtgcctggg tggaa

Fig.13A

EXON 7: 181 bp        (bp 1176-1356)

aataggacaa gatttacaac aaagtgcctt gtcccttata ctcctgccag GGGTAATTCT
TCCTCACCAG CCTTTGGGGA GCTGAAAGAC TACTACCTCT TCTACCTGAA AAGCAAGTCC
CCCAGGGAGG AGCTGCTGAA GATGTGGGGC GAGGAGCTCA CCAGCGAAGA GAGTGTCTTT
GAAGTCTTTG AACACTACCT CTCTGGAGAG CCGAATCGCC ATGGCTACAG Agtgagtggg
gtgaggagga acggcccagc tttgtctcag ccttgg EXON 8: 183 bp        (bp 1357-1539)

cccagtccca gactcagtgc tgccctcgct cagcgcaccc tgccctgcag GTAACCTGCC
TGCCCTGGAA CGATGAACCC CTGGCAGCGG AAACCAGCCT GATGAAGGAA GAGCTGCTCC
GCGTGAACAG GCTGGGCATC CTCACCATCA ACTCTCAGCC CAACATCAAC GCAAAACCAT
CCTCAGACCC TGTTGTGGGC TGGGGCCCCA GTGGGGGTTA TGTCTTCCAG AAGgtatgct
aggatgcagt actctcgata tccccaggga ctgacacaga acc EXON 9: 102 bp        (bp 1540-1641)

gagaacttgg caagtagtgg ggttgacatg ttgggtgtat tctccctcag GCCTACCTCG
AATTCTTCAC CTCCCGTGAA ACTGTGGAGG CGCTTCTGCA GGTGCTGAAG ACATACGAGC
TGCGGGTCAA CTACCACATC GTGGACGTGA AGgtaagcca gctccctccg gcttagacgc
agcaaggctt gaaaacacct aca EXON 10: 120 bp       (bp 1642-1761)

agcagtggga ggttgcggtc accctgcctc agccctgcct ctgttctcag GGAGAGAACA
TCACTAATGC CCCTGAGCTG CAGCCCAATG CCGTGACGTG GGGCATCTTC CCGGGTCGAG
AGATCATCCA GCCTACTGTG GTGGACCCCA TCAGCTTCAT GTTCTGGAAG gtaagggagt
gggagggagt ggaggaccct ggctaccgtg agagcccag EXON 11: 216 bp (stop codon)    (bp 1762-1977)

ggaggtacca gccgtgctga ccctgctcgt gtgtctctgt tcacacgtag GATGAGGCCT
TTGCCCTGTG GATCGAGCAG TGGGGCAAGC TATACGAGGA GGAGTCGCCA TCCCGCATGA
TCATCCAATA CATCCATGAC AACTATTTCC TGGTCAACCT GGTGGACAAC GAGTTCCGC
TGGACAGCTG CCTGTGGCAG GTGGTGGAGG ACACGTTTGA GCTGCTCAAC AGGCATCCCA
CGGAGAGAGA GACACAGGCT CCATGAgcct gcatctctca acaggcacac catggagaga
gagacacagg ctctgtgagc cgtgcatccc tcaacaggca caccacggag agagagacac
aggctccgtg agcctgcatc ccggtatctt cctcacctgg agccctctc cctcatctct
ctacaca

Fig.13B

```
hMTHFR  MVNEARGNSSLNPCLEGSASSGSESSKDSSRCSTPGLDPERHERLREKMRRRLESGDKWF
mMTHFR  □□□□□□□sg□ps□rs□□□-□□□□□□□□□□□□□□□□s□□□□□□□□□□□□□□□□mds□□□□□
bMTHFR  ---------------------------fhasqrda□nqsl-aevq-□qinv hMTHFR  SLEFFPPRTAEGAVNLISRFDRMAAGGPLYIDVTWHPAGDPGSDKETSSMMIASTAVNYC
mMTHFR  □□□□□□□□□□□□□□□□□□□□□□□□□□□□□□□fv□□□□□□□□□□□□□□□□□□□□□□□□□□
bMTHFR  □f□□□□□□□s□meqt□wnsi□□lsslk□kfvs□□-yg□-ns□erdr□h□--□kgik-drt hMTHFR  GLETILHMTCCRQRLEEITGHLHKAKQLGLKNIMALRGDPIGDQWEEEEGGFNYAVDLVK
mMTHFR  □□□□□□d□□□□q□□p□□□□□□□□r□□□□□□□□□□□□□□□v□□h□□a□□□□□s□□t□□□□
bMTHFR  □□□aap□l□□idatpd□lrtiardywnn□irh□v□□□□□lpp-gsgkp□m---□□s□□□t hMTHFR  HIRSEFGDYFDICVAGYPKGHPEAGSFEADLKHLKEKVSAGADFIITQLFFEADTFFRFV
mMTHFR  □□□t□□a□□□□□□□□□□□r□□□d□e□□□d□□□□□□□□□□□□□□□□□□□□□□□s□□□s□□
bMTHFR  llk-□va□-□□□s□□a□□ev□□□□k□aq□□□ln□□r□□d□□□nra□□□f□□dvesyl□□r hMTHFR  KACTDMGITCPIVPGIFPIQGYHSLRQLVKLSKLEVPQEIKDVIEPIKDNDAAIRNYGIE
mMTHFR  □□□□ei□□s□□□l□□□□□□□□□□t□□□□□□□□□□□□□□□□k□□□□□□□□□□□□□□□□□□
bMTHFR  dr□vsa□□dve□i□□□l□vsnfkqakkfadmtnvri□awmaqmfdgld□daetrklv□an hMTHFR  LAVSLCQELLASGLVPGLHFYTLNREMATTEVLKRLGMWTEDPRRPLPWALSAHPKRREE
mMTHFR  □□□x□□r□□□ds□□□□□□□□□□□□□□□v□□m□□□□q□□□□□□□□□□□□□□□□□□□□□□□
bMTHFR  i□mdmvk-i□sreg□kdf□□□□□□□aemsyaicht□□vr------------------- hMTHFR  DVRPIFWASRPKSYIYRTQEWDEFPNGRWGNSSSPAFGELKDYYLFYLKSKSPKEELLKM
mMTHFR  □□□□□□□□□□□□□□□□□□□□□□d□□□□□□□□□□□□□□□□□□□□□□□□□□□□□□r□□□□□
bMTHFR  -------------------------------------------------------- hMTHFR  WGEELTSEASVFEVFVLYLSGEPNRNGHKVTCLPWNDEPLAAETSLLKEELLRVNRQGIL
mMTHFR  □□□□□□□□e□□□□□□eh□□□□□□□□□h□yr□□□□□□□□□□□□□□□□□□m□□□□□□□□□l□□□
bMTHFR  -------------------------------------------------------- hMTHFR  TINSQPNINGKPSSDPIVGWGPSGGYVFQKAYLEFFTSRETAEAALLQVLKKYELRVNYHL
mMTHFR  □□□□□□□□□a□□□□□□v□□□□□□□□□□□□□□□□□□□□□□□□□□□v□□□□□□□□t□□□□□□□□i
bMTHFR  -------------------------------------------------------- hMTHFR  VNVKGENITNAPELQPNAVTWGIFPGREIIQPTVVDPVSFMFWKDEAFALWIERWGKLYE
mMTHFR  □d□□□□□□□□□□□□□□□□□□□□□□□□□□□□□□□□□□□□□□i□□□□□□□□□□□□□□□q□□□□□□
bMTHFR  -------------------------------------------------------- hMTHFR  EESPSRTIIQYIHDNYFLVNLVDNDFPLDNCLWQVVEDTLELLNRPTQNARETEAP
mMTHFR  □□□□□□m□□□□□□□□□□□□□□□□□□□e□□□□s□□□□□□□□□f□□□□□h-pte□□□q□□
bMTHFR  --------------------------------------------------------
```

Fig. 15

METHODS FOR SELECTING A THERAPY FOR A SUBJECT SUFFERING FROM SCHIZOPHRENIA

RELATED APPLICATION

This application is a divisional of pending U.S. patent application Ser. No. 09/592,595 filed Jun. 12, 2000, which is a continuation-in-part of U.S. patent application Ser. No. 09/258,928 filed Mar. 1, 1999 (now U.S. Pat. No. 6,218,120), which is a continuation in part of U.S. patent application Ser. No. 08/738,000 filed Feb. 12, 1997 (now U.S. Pat. No. 6,074,821), which claims priority from PCT CA 95/00314, filed May 25, 1995, and GB 9410620.0, filed May 26, 1994.

BACKGROUND OF THE INVENTION (a) Field of the Invention

The invention relates to a cDNA probe for human methylenetetrahydrofolate reductase (MTHFR), and its uses.

(b) Description of Prior Art

Folic acid derivatives are coenzymes for several critical single-carbon transfer reactions, including reactions in the biosynthesis of purines, thymidylate and methionine. Methylenetetrahydrofolate reductase (MTHFR; EC 1.5.1.20) catalyses the NADPH-linked reduction of 5,10-methylenetetrahydrofolate to 5-methyltetrahydrofolate, a co-substrate for methylation of homocysteine to methionine. The porcine liver enzyme, a flavoprotein, has been purified to homogeneity; it is a homodimer of 77-kDa subunits. Partial proteolysis of the porcine peptide has revealed two spatially distinct domains: an N-terminal domain of 40 kDa and a C-terminal domain of 37 kDa. The latter domain contains the binding site for the allosteric regulator S-adenosylmethionine.

Hereditary deficiency of MTHFR, an autosomal recessive disorder, is the most common inborn error of folic acid metabolism. A block in the production of methyltetrahydrofolate leads to elevated homocysteine with low to normal levels of methionine. Patients with severe deficiencies of MTHFR (0–20% activity in fibroblasts) can have variable phenotypes. Developmental delay, mental retardation, motor and gait abnormalities, peripheral neuropathy, seizures and psychiatric disturbances have been reported in this group, although at least one patient with severe MTHFR deficiency was asymptomatic. Pathologic changes in the severe form include the vascular changes that have been found in other conditions with elevated homocysteine, as well as reduced neurotransmitter and methionine levels in the CNS. A milder deficiency of MTHFR (35–50% activity) has been described in patients with coronary artery disease (see below). Genetic heterogeneity is likely, considering the diverse clinical features, the variable levels of enzyme activity, and the differential heat inactivation profiles of the reductase in patients' cells.

Coronary artery disease (CAD) accounts for 25% of deaths of Canadians. Cardiovascular risk factors (male sex, family history, smoking, hypertension, dyslipoproteinemia and diabetes) account for approximately 60 to 70% of the ability to discriminate CAD patients from healthy subjects. Elevated plasma homocysteine has also been shown to be an independent risk factor for cardiovascular disease.

Homocysteine is a sulfhydryl-containing amino acid that is formed by the demethylation of methionine. It is normally metabolized to cysteine (transsulfuration) or re-methylated to methionine. Inborn errors of metabolism (as in severe MTHFR deficiency) causing extreme elevations of homocysteine in plasma, with homocystinuria, are associated with premature vascular disease and widespread arterial and venous thrombotic phenomena. Milder elevations of plasma homocysteine (as in mild MTHFR deficiency) have been associated with the development of peripheral vascular disease, cerebrovascular disease and premature CAD.

Homocysteine remethylation to methionine requires the folic acid intermediate, 5-methyltetrahydrofolate, which is produced from 5,10-methylenetetrahydrofolate folate through the action of 5,10-methylenetetrahydrofolate reductase (MTHFR). Deficiency of MTHFR results in an inability to metabolize homocysteine to methionine; elevated plasma homocysteine and decreased methionine are the metabolic consequences of the block. Severe deficiencies of MTHFR (less than 20% of activity of controls) as described above, are associated with early-onset neurologic symptoms (mental retardation, peripheral neuropathy, seizures, etc.) and with atherosclerotic changes and thromboembolism. Milder deficiencies of MTHFR (35–50% of activity of controls), with a thermolabile form of the enzyme, are seen in patients with cardiovascular disease without obvious neurologic abnormalities.

In a survey of 212 patients with proven coronary artery disease, the thermolabile form of MTHFR was found in 17% of the CAD group and 5% of controls. In a subsequent report on 339 subjects who underwent coronary angiography, a correlation was found between thermolabile MTHFR and the degree of coronary artery stenosis. Again, traditional risk factors (age, sex, smoking, hypertension, etc.) were not significantly associated with thermolabile MTHFR. All the studies on MTHFR were performed by enzymatic assays of MTHFR in lymphocytes, with measurements of activity before and after heat treatment to determine thermolability of the enzyme.

Since 5-methyltetrahydrofolate, the product of the MTHFR reaction, is the primary form of circulatory folate, a deficiency in MTHFR might lead to other types of disorders. For example, periconceptual folate administration to women reduces the occurrence and recurrence of neural tube defects in their offspring. Neural tube defects are a group of developmental malformations (meningomyelocele, anencephaly, and encephalocele) that arise due to failure of closure of the neural tube. Elevated levels of plasma homocysteine have been reported in mothers of children with neural tube defects. The elevated plasma homocysteine could be due to a deficiency of MTHFR, as described above for cardiovascular disease.

Neuroblastomas are tumors derived from neural crest cells. Many of these tumors have been reported to have deletions of human chromosome region 1p36, the region of the genome to which MTHFR has been mapped. It is possible that MTHFR deletions/mutations are responsible for or contribute to the formation of this type of tumor. MTHFR abnormalities may also contribution to the formation of other types of tumors, such as colorectal tumors, since high dietary folate has been shown to be inversely associated with risk of colorectal carcinomas.

MTHFR activity is required for homocysteine methylation to methionine. Methionine is necessary for the formation of S-adenosylmethionine, the primary methyl donor for methylation of DNA, proteins, lipids, neurotransmitters, etc. Abnormalities in MTHFR might lead to lower levels of methionine and S-adenosylme-thionie, as well as to elevated homocysteine. Disruption of methylation processes could result in a wide variety of conditions, such as neoplasias, developmental anomalies, neurologic disorders, etc.

Although the MTHFR gene in *Escherichia coli* (metF) has been isolated and sequenced, molecular studies of the enzyme in higher organisms have been limited without the availability of an eukaryotic cDNA.

It would be highly desirable to be provided with a cDNA probe for human methylenetetrahydrofolate reductase (MTHFR). This probe would be used for identification of sequence abnormalities in individuals with severe or mild MTHFR deficiency, including cardiovascular patients and patients with neurologic symptoms or tumors. The probe would also be used in gene therapy, isolation of the gene, and expression studies to produce the MTHFR protein. The probe would also provide the amino acid sequence of the human MTHFR protein, which would be useful for therapy of MTHFR deficiency by biochemical or pharmacological approaches.

It would be highly desirable to be provided with a molecular description of mutations in methylenetetrahydrofolate reductase deficiency.

Patients with sequence abnormalities in MTHFR might have different responses to drugs, possibly but not limited to drugs that affect folate metabolism. Therefore, it would be useful to know if these mutations are present before determining the appropriate therapy. The drugs/diseases for which this might be relevant include cancer chemotherapeutic agents, antibiotics, antiepileptic medication, antiarthritic medication, etc.

SUMMARY OF THE INVENTION

One aim of the present invention is to provide a cDNA probe for human methylenetetrahydrofolate reductase (MTHFR).

Another aim of the present invention is to provide a molecular description of mutations in methylenetetrahydrofolate reductase deficiency.

Another aim of the present invention is to provide a nucleic acid and amino acid sequence for human methylenetetrahydrofolate reductase.

Another aim of the present invention is to provide potential therapy for individuals with methylenetetrahydrofolate reductase deficiency.

Another aim of the present invention is to provide a system for synthesis of MTHFR protein in vitro.

A further aim of the present invention is to provide technology/protocol for identification of sequence changes in the MTHFR gene.

In accordance with one aspect of the present invention, there is provided a cDNA probe for human methylenetetrahydrofolate reductase (MTHFR) gene encoded by a nucleotide sequence as set forth in SEQ ID NO:1 or having an amino acid sequence as set forth in SEQ ID NO:2. The probe comprises a nucleotide sequence that hybridizes to the MTHFR nucleotide sequence, or an amino acid sequence that hybridizes to the MTHFR amino acid sequence.

In accordance with another aspect of the present invention, there is provided a method of diagnosis of methylenetetrahydrofolate reductase (MTHFR) deficiency in a patient with MTHFR deficiency. The method comprises the steps of amplifying a DNA sample obtained from the patient or reverse-transcripting a RNA sample obtained from the patient into a DNA and amplifying the DNA, and analyzing the amplified DNA to determine at least one sequence abnormality with respect to a human MTHFR encoded by a nucleotide sequence as set forth in SEQ ID NO:1 or having an amino acid sequence as set forth in SEQ ID NO:2, the sequence abnormality being indicative of MTHFR deficiency.

The sequence abnormality may comprise a mutation selected from a group consisting of 167G/A, 482G/A, 559C/T, 677C/T, 692C/T, 764C/T, 792+1G/A, 985C/T, 1015C/T, 1081C/T, 1298A/C and 1317T/C.

The selected mutation may consist of 677C/T.

The MTHFR deficiency may be associated with a disease, disorder, or dsyfuntion selected from a group consisting of cardiovascular disorders, cancer, osteoporosis, increased risk of occurrence of a neural tube defect in an offspring of said patient, neurological disorders, disorders influenced by folic acid metabolism, metabolic or endocrine disease, inborn errors of metabolism, inflammation, immune disorders, psychiatric illness, neoplastic disease and other related disorders, and renal disease.

The cancer may be selected from a group consisting of neuroblastomas and colorectal carcinomas.

The disorder may consist of osteoporosis.

In accordance with yet another aspect of the present invention, there is provided a method for gene therapy of methylenetetrahydrofolate reductase (MTHFR) deficiency in a patient. The method comprises the steps of producing a recombinant vector for expression of MTHFR under the control of a suitable promoter, the MTHFR being encoded by a nucleotide sequence as set forth in SEQ ID NO:1 or having an amino acid sequence as set forth in SEQ ID NO:2, and transfecting the patient with the vector for expression of MTHFR.

In accordance with yet another aspect of the present invention, there is provided a human methylenetetrahydrofolate reductase (MTHFR) protein encoded by a nucleotide sequence as set forth in SEQ ID NO:1 or having an amino acid sequence as set forth in SEQ ID NO:2.

In accordance with yet another aspect of the present invention, there is provided a recombinant human methylenetetrahydrofolate reductase (MTHFR) protein encoded by a nucleotide sequence as set forth in SEQ ID NO:1 or having an amino acid sequence as set forth in SEQ ID NO:2.

In accordance with yet another aspect of the present invention, there is provided a method of treatment of MTHFR-deficiency in a patient that comprises administering such a MTHFR protein.

The MTHFR deficiency may be associated with a cancer.

The cancer may be selected from a group consisting of neuroblastomas and colorectal carcinomas.

In accordance with yet another aspect of the present invention, there is provided a method of preventing an occurrence of a neural tube defect in an offspring of a patient. The method comprises administering to the patient such a MTHFR protein.

In accordance with yet another aspect of the present invention, there is provided a method for determining drug susceptibility, drug response or drug toxicity of a patient having a methylenetetrahydrofolate reductase (MTHFR) deficiency. The method comprises the steps of amplifying a DNA sample obtained from the patient or reverse-transcripting a RNA sample obtained from the patient into a DNA and amplifying said DNA, analyzing the amplified DNA to determine a sequence abnormality in a MTHFR sequence, the MTHFR sequence being encoded by a nucleotide sequence as set forth in SEQ ID NO:1 or having an amino acid sequence as set forth in SEQ ID NO:2, and administering the drug to the patient and determining the sequence abnormality associated with the patient susceptibility, response or toxicity to the drug. Further, in human therapeutic approaches, both pharmacokinetics and pharmacodynamics may be influenced by folic acid metabolism. Pharmacokinetics includes, but is not excluded to, factors such as absorption, distribution, metabolism, and excretion. Other considerations include safety and toxicity. Examples of toxicities from therapeutics include, but are not limited to, blood dyscrasias, cutaneous toxicities, systemic toxicity, CNS toxicity, hepatic toxicity, cardiovascular toxicity, pulmonary toxicity, and renal toxicity.

The sequence abnormality may comprise a mutation selected from a group consisting of 167G/A, 482G/A, 559C/T, 677C/T, 692C/T, 764C/T, 792+1G/A, 985C/T, 101SC/T, 1081C/T, 1298A/C and 1317T/C and the drug may be selected from a group consisting of cancer chemotherapeutic agents, antibiotics, antiepileptic agents, antiarthritic agents, and anti-inflammatory agents. Examples of chemotherapeutic agents include alkylating agents (nitrogen mustards, ethylenimines and methylmelamines, alkyl sulfonates, nitrosoureas, triazenes), antimetabolites (folic acid analogs, pyrimidine analogs, purine analogs and related inhibitors), and natural products (vinca alkyloids, epipodophyllotoxins, antibiotics, enzymes, biological response modifiers). Examples of anti-inflammatory agents include non-steroidal anti-inflammatory agents, steroids, antihistaminergics, 5-LO inhibitors, cytokine agonists, and cytokine antagonists. The drug may also include therapies for metabolic or endocrine disease such as hormone agonists and antagonists, intracellular response modifiers, and secretegogues. Other possible drugs include therapies for cardiovasular disease or disorders such as antianemic, antiangina, antiarrythmics, antihypertensives, positive inotropic agents, and antithrombotics. The drug may also be a therapy for an immune disorder, such as immune modulators, immunosuppression agents, and immunostimulation agents. Additionally, any other drug for the treatment of a metabolic disease, inborn errors of metabolism, psychiatric disorders, neoplastic disease and other related disorders, and renal disease is relevant to the invention The MTHFR deficiency may be associated with a disorder selected from a group consisting of cardiovascular disorders, coronary and arterial disorders, neurological disorders, increased risk of occurrence of a neural tube defect in an offspring, cancer, osteoporosis and other disorders influenced by folic acid metabolism.

In accordance with yet another aspect of the present invention, there is provided a method of treatment of a patient having a cancer comprising the step of inhibiting gene expression for a MTHFR protein or a mRNA produced form the gene.

In accordance with yet another aspect of the present invention, there is provided a method of treatment of a patient having a cancer comprising the step of inhibiting the MTHFR protein.

The use of MTHFR alleles as diagnostic, therapeutic, prognostic, and pharmacogenomic markers may also be applied to neurological disorders such as psychoses and to other diseases and disorders that may be treated with anti-psychotic therapeutics. The presence of particular MTHFR alleles may be used to predict the safety and efficacy of a particular therapy and to select preferred therapies for these subjects.

Accordingly, in one aspect, the invention provides a method of diagnosing a psychosis in a subject. This method involves analyzing the MTHFR nucleic acid in a sample obtained from the subject and determining the presence of at least one heterozygous MTHFR mutant allele in the subject that is indicative of the subject having the psychosis.

In a related aspect, the invention features a method of determining a risk for a psychosis or a propensity for a psychosis in a subject. This method includes analyzing the MTHFR nucleic acid in a sample obtained from said subject and determining the presence of at least one heterozygous MTHFR mutant allele in the subject that is indicative of the risk for a psychosis or the propensity for a psychosis in the subject.

In another aspect, the invention provides a method of diagnosing a psychosis in a subject. This method involves analyzing the MTHFR nucleic acid in a sample obtained from the subject and determining the presence of a heterozygous MTHFR mutation at position 677 and/or the presence of at least one other MTHFR mutation at a position other than 677. These mutations are indicative of the subject having the psychosis.

The invention also provides a related method of diagnosing a risk for a psychosis or a propensity for a psychosis in a subject. This method includes analyzing the MTHFR nucleic acid in a sample obtained from the subject and determining the presence of a heterozygous MTHFR mutation at position 677 and the presence of at least one other MTHFR mutation at a position other than 677. These mutations are indicative of the risk for a psychosis or the propensity for a psychosis in the subject.

In addition to their use in diagnosing a psychosis or an increased risk for a psychosis, the determination of one or more mutations in an MTHFR allele may also be used to classify subjects into a subgroup for a clinical trial of an anti-psychotic therapy, to determine a preferred anti-psychotic therapy for a subject, or to determine whether the MTHFR mutations are indicative of a response to an anti-psychotic therapy.

Accordingly, the invention also provides a method for stratification of subjects involved in a clinical trial of an anti-psychotic therapy. This method involves analyzing the MTHFR nucleic acid in a sample obtained from a subject and determining before, during, or after the clinical trial the presence of at least one MTHFR mutant allele in the subject that places the subject into a subgroup for the clinical trial. In one preferred embodiment, the anti-psychotic therapy is a therapy for schizophrenia.

In another aspect, the invention provides a method for selecting a therapy for a subject suffering from a psychosis. This method include analyzing the MTHFR nucleic acid in a sample obtained from the subject and determining the presence of at least one MTHFR mutant allele in the subject that is indicative of the safety or efficacy of the therapy.

In yet another aspect, the invention features a method for determining whether a mutant MTHFR allele is indicative of a response to a therapy for a psychosis. This method includes (a) determining whether the response of a first subject or set of subjects at increased risk for or diagnosed with the psychosis differs from the response of a second subject or set of subjects at increased risk for or diagnosed with the psychosis, (b) analyzing the MTHFR nucleic acid in a sample obtained from the first and second subjects or sets of subjects, and (c) determining whether at least one MTHFR mutant allele differs between the first and second subjects or sets of subjects. If the MTHFR mutant allele is correlated to a response to the therapy, the mutant allele is determined to be indicative of the safety or efficacy of the therapy.

The invention also provides a method for preventing, delaying, or treating a psychosis in a subject. This method includes (a) analyzing the MTHFR nucleic acid in a sample obtained from the subject, (b) determining the presence of at least one MTHFR mutant allele in the subject that is predictive of the safety or efficacy of at least one antipsychotic therapy, (c) determining a preferred therapy for the subject, and (d) administering the preferred therapy to the subject.

In another aspect, the invention provides a pharmaceutical composition including a compound which has a differential effect in subjects having at least one copy of a particular MTHFR allele and has a pharmaceutically acceptable carrier, excipient, or diluent. This compound is preferentially effective to treat a subject having the particular MTHFR allele. In a preferred embodiment, the composition is adapted to be preferentially effective based on the unit dosage, presence of additional active components, complexing of the compound with stabilizing components, or inclusion of components enhancing delivery or slowing excretion of the compound. In another preferred embodiment, the compound is deleterious to subjects having at least one copy of the particular MTHFR allele or in subjects not having at least one copy of the particular MTHFR allele, but not in both. In yet another preferred embodiment, the subject suffers from a disease or condition selected from the group consisting of amyotrophic lateral sclerosis, anxiety, dementia, depression, epilepsy, Huntington's disease, migraine, demyelinating disease, multiple sclerosis, pain, Parkinson's disease, schizophrenia, psychoses, and stroke. In still another preferred embodiment, the pharmaceutical composition is subject to a regulatory restriction or recommendation for use of a diagnostic test determining the presence or absence of at least one particular MTHFR allele. In another preferred embodiment, the pharmaceutical composition is subject to a regulatory limitation or recommendation restricting or recommending restriction of the use of the pharmaceutical composition to subjects having at least one particular MTHFR allele. In yet another preferred embodiment, the pharmaceutical composition is subject to a regulatory limitation or recommendation indicating the pharmaceutical composition is not to be used in subjects having at least one particular MTHFR allele. In still another preferred embodiment, the pharmaceutical composition is packaged, and the packaging includes a label or insert restricting or recommending the restriction of the use of the pharmaceutical composition to subjects having at least one particular MTHFR allele. In yet another embodiment, the pharmaceutical composition is packaged, and the packaging includes a label or insert requiring or recommending the use of a test to determine the presence or absence of at least one particular MTHFR allele in a subject. Preferably, the compound is an anti-psychotic therapy, such as a therapy for schizophrenia.

In preferred embodiments of each of the aspects of the invention, the mutant MTHFR allele encodes an MTHFR protein with reduced activity or reduced thermal stability. It is also contemplated that the MTHFR protein may have a reduced half-life. Preferably, the MTHFR mutation is a missense mutation. Preferred MTHFR mutations include a G/A mutation at position 167, a G/A mutation at position 482, a C/T mutation a position 559, a C/T mutation at position 677, a C/T mutation at position 692, a C/T mutation at position 764, a G/A mutation at position 792+1, a C/T mutation at position 985, a C/T mutation at position 1015, a C/T mutation at position 1081, an A/C mutation at position 1298, and a T/C mutation at position 1317. It is also contemplated that the mutations at these positions may involve changes to other nucleotides. In other preferred embodiments, the subject has at least two MTHFR mutant alleles. Preferably the two or more mutant MTHFR alleles have at least one of the following: a G/A mutation at position 167, a G/A mutation at position 482, a C/T mutation a position 559, a C/T mutation at position 677, a C/T mutation at position 692, a C/T mutation at position 764, a G/A mutation at position 792+1, a C/T mutation at position 985, a C/T mutation at position 1015, a C/T mutation at position 1081, an A/C mutation at position 1298, or a T/C mutation at position 1317. In yet other preferred embodiments, the MTHFR mutation results in a change in the amino acid at position 226 of the encoded protein from alanine found in wild-type MTHFR to any other amino acid, including valine or residues other than valine. In still other preferred embodiments, the mutation results in a change in amino acid 433 of the encoded protein from glutamic acid to any other amino acid, including alanine or residues other than alanine. When two mutations are present at different nucleotide positions, the mutations may be in the same or different MTHFR alleles. The MTHFR mutation may, without limitation, also be an insertion, deletion, or frameshift mutation.

Preferably, the psychosis being diagnosed or treated is schizophrenia. The psychosis may also be any other psychosis such as manic-depressive disease, depression with psychotic features, organic psychotic disorders, psychosis in alcohol or drug intoxication, postinfection psychosis, postpartum psychosis, senile psychosis, traumatic psychosis, manic-depressive psychosis, psychosis from toxic agents, and acute idiopathic psychotic illnesses.

The use of MTHFR alleles as diagnostic, therapeutic, prognostic, and pharmacogenomic markers may also be applied to other neurological disorders. Examples of neurological disorders include, but are not limited to, mood disorders, neurodegenerative diseases, cognitive disorders, seizure disorders such as epilepsy, headaches such as migraines, pain associated with the central nervous system, demyelinating diseases, spasticity, neural tube defects, neurofibromatosis, and ischemic cerebrovascular diseases such as thrombotic and hemorrhagic strokes. Mood disorders include but are not excluded to conditions such as unipolar depression, bipolar depression and anxiety. Examples of neurodegenerative diseases include amyotrophic lateral sclerosis, Parkinson's disease, acquired or symptomatic parkinsonism, Huntington's disease, and heredodegenerative disease. Examples of cognitive disorders include dementia, dementia of the Alzheimer's type, vascular dementia, multi-infarct dementia and posttraumatic dementia. Demyelinating diseases consist of diseases such as the following: multiple sclerosis (MS), Marburg and Balo forms of MS, neuromyelitis optica, perivenous encephalitits, acute disseminated encephalomyelitits, and acute necotizing hemmorhhagic encephalitis.

The methods of the invention may also be applied to non-psychiatric conditions for which anti-psychotic drugs are used. Examples of these conditions include nausea, vomiting, movement disorders associated with neurodegenerative diseases such as Huntington's disease and Tourette's syndrome, pruritis, and chronic hiccough. Cardiovascular disorders, cancers, neoplastic disease and other related disorders, osteoporosis, neural tube defects, neurological disorders, disorders influenced by folic acid metabolism, metabolic or endocrine disease, inborn errors of metabolism, inflammation, immune disorders, psychiatric illness, and renal disease are also relevant to these methods.

It is to be understood that the methods of the invention may be applied to any other diseases or disorders. Examples of other diseases or disorders may include those that are indirectly or directly affected by an increase or decrease in MTHFR activity, homocysteine levels, methionine levels, S-adenosylmethionine activity, or methylation.

The therapies relevant to the methods of the present invention include all clinically used therapies and therapies in preclinical or clinical development for the aforementioned diseases and disorders. Preferred therapies include the therapies listed in databases such as Life Cycle, R&D Focus, IMS World Publications, London UK or in any other database of therapies that are in development and/or that are FDA approved. Preferred anti-psychotic therapies include conventional neuroleptics such as phenothiazines (e.g. chlorpromazine), thioxanthenes (e.g. thiothixene), butyrophenones (e.g. haloperidol, one of the most useful conventional anti-psychotics), dibenzoxazepines, dibenzodiazepines, diphenylbutylpiperidines, and other heterocyclic compounds. Preferred atypical neuroleptics include compounds such as clozaril, risperidone, olanzapine, quetiapine, ziprasidone, amisulpride, sertindole, and iloperidone. Additionally, anti-psychotic therapies, such as loxapine, may have pharmacology intermediate between that of conventional and atypical neuroleptics. In preferred embodiments, the treatment or prevention of a neurological disease includes administration of one or more therapeutically active compounds that bind to a dopamine, histamine, muscarinic cholinergic, α-adrenergic, or serotonin receptors.

Examples of other pharmaceutically active compounds which may be used as anti-psychotics include synthetic organic molecules, naturally occurring organic molecules, nucleic acid molecules, biosynthetic proteins or peptides, naturally occurring peptides or proteins, and modified naturally occurring peptides or proteins. In preferred embodiments, the preferred therapy consists of an altered dose regime compared to other clinically used dose regimes or to the administration of a combination of therapeutics. It is also contemplated that the preferred therapy may consist of other medical treatments, such as surgical procedures, electroconvulsive therapy, or psychotherapy. Examples of psychotherapies include dynamic psychotherapy, cognitive-behavioral therapy, interpersonal therapy, behavioral therapy, group psychotherapy, and family therapy. For the administration of a therapeutically active compound to a subject, any mode of administration or dosing regime may be used. It is to be understood that for any particular subject, specific dosage regimes should be adjusted over time according to the individual need and the professional judgment of the person administering or supervising the administration of the compositions.

Descriptions of clinically used therapies (for example, for psychosis) and guidelines for their use are readily available in common references such as the Physicians Desk Reference (PDR). Additionally, therapeutics are described and listed in medical, pharmacy, and pharmacology journals and textbooks, such as *Goodman and Gilman's The Pharamcological Basis of Therapeutics*, (Hardman and Limbird (eds.) Ninth Edition, McGraw-Hill, New York, 1996). Additional information on FDA approved therapeutics and therapies in clinical trials for particular indications, diseases, or disorders may be easily found in electronic databases available through subscription and pharmaceutical company information.

By "preferred therapy" is meant a therapy for a disease, disorder, or dysfunction that is efficacious, safe, and/or has reduced toxicity compared to another therapy for the disease or disorder. The preferred therapy selected based on one or more mutations in one or more MTHFR alleles is preferably effective in at least 20, 30, 50, 70, or 90% of the subjects having the MTHFR mutation(s). By "effective" is meant ablates, reduces, or stabilizes symptoms in a subject suffering from a disease, disorder, or dysfunction prevents the onset of symptoms in a subject at risk for a disease, disorder, or dysfuction, or results in a later age-at-onset of symptoms in the subject compared to the average age-at-onset for the corresponding untreated subjects with the same MTHFR mutation(s). The effectiveness of the therapy for the treatment of a psychosis may be evaluated based on the Clinical Global Impression (CGI), Diagnostic Interview for Genetic Studies (DIGS), Global Assessment Score (GAS), or Brief Psychiatric Rating Scale (BPRS) using standard procedures. Preferably, the total BPRS score is lowered by 5, more preferably 10, and most preferably 15 points. By "reduced toxicity" is meant lower level of adverse pharmacological or physiological effects. Preferably, the therapy produces clinically unacceptable side-effects in 5, 10, 20, 30, or 50% fewer of the subjects having the MTHFR mutations(s) than in subjects who do not have one or ore of the MTHFR mutations.

A "polymorphism" is intended to mean a mutation or allelic variance present in 1% or more of alleles of the general population. A polymorphism is disease-causing when it is present in patients with a disease but not in the general population. However, a polymorphism present both in patients having a disease and in the general population is not necessarily benign. The definition of a disease-causing substitution, as distinct from a benign polymorphism, is based on 3 factors: (1) absence of the change in at least 50 independent control chromosomes; (2) presence of the amino acid in the bacterial enzyme, attesting to its evolutionary significance and (3) change in amino acid not conservative. Although expression of the substitutions is required to formally prove that they are not benign, the criteria above allow us to postulate that the changes described in this report are likely to affect activity.

BRIEF DESCRIPTION OF THE DRAWINGS

FIGS. 1A to 1F illustrate the first cDNA coding sequence (SEQ ID NO:1 and NO:2) for methylenetetrahydrofolate reductase (MTHFR);

FIG. 2 is the alignment of amino acids for human methylenetetrahydrofolate reductase (MTHFR), the metF genes from *E. Coli* (ECOMETF), and *S. Typhimurium* (STYMETF), and an unidentified open reading frame in *Saccharomyces cerevisiae* that is divergently transcribed from an excision repair gene (ysRAD1);

FIGS. 6A to 6C illustrate the total available sequence (SEQ ID NO:3 and NO:4) of human MTHFR cDNA;

FIGS. 12A–12B illustrate the exonic sequences of the human MTHFR gene with their flanking intronic sequences;

FIGS. 13A–13B illustrate the exonic sequences of the mouse MTHFR gene with their flanking intronic sequences;

FIG. 15 illustrates the alignment of MTHFR amino acid sequences for the human MTHFR (hMTHFR), mouse MTHFR (MMTHFR) and the MetF gene of bacteria (bMTHFR).

DETAILED DESCRIPTION OF THE INVENTION

Sequencing of Peptides from Porcine MTHFR

Figure 3A:
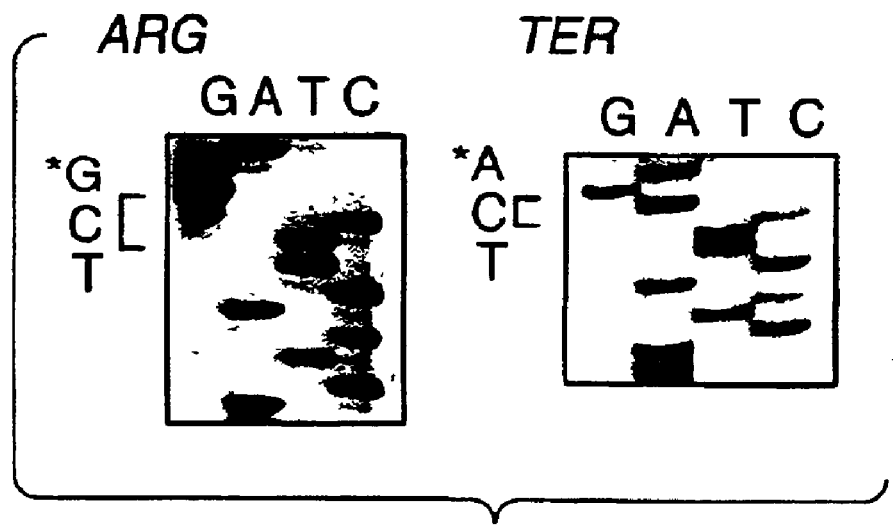
FIGS. 3A and 3B illustrate the sequencing and restriction enzyme analysis for the Arg to Ter substitution.

Homogeneous native porcine MTHFR was digested with trypsin to generate a 40 kDa N-terminal fragment and a 31 kDa C-terminal fragment; the 31 kDa fragment is a proteolytic product of the 37 kDa fragment. The fragments were separated by SDS-PAGE, electroeluted, and the denatured fragments were digested with lysyl endopeptidase (LysC). The resulting peptides were separated by reversed-phase HPLC and subjected to sequence analysis by Edman degradation (details contained in Goyette P et al., *Nature Genetics*, 1994, 7:195–200).

Isolation and Sequencing of cDNAs

Two degenerate oligonucleotides were synthesized based on the sequence of a 30 amino acid porcine MTHFR peptide (first underlined peptide in FIG. 2). These were used to generate a 90 bp PCR product, encoding the predicted peptide, from reverse transcription-PCR reactions of 500 ng pig liver polyA+ RNA. A pig-specific (non-degenerate, antisense) PCR primer was then synthesized from this short cDNA sequence. Using this primer and a primer for phage arms, a human liver λgt10 cDNA library (Clontech) was screened by PCR; this technique involved the generation of phage lysate stocks (50,000 pfu) which were boiled for 5 min and then used directly in PCR reactions with these two primers. PCR fragments were then sequenced directly (Cycle Sequencing™ kit, GIBCO), and a positive clone was identified by comparison of the deduced amino acid sequence to the sequence of the pig peptide (allowing for inter-species variations). The positive stock was then replated at lower density and screened with the radiolabelled positive PCR product by plaque hybridization until a well-isolated plaque was identified. Phage DNA was purified and the insert was then subcloned into pBS+ (Bluescript) and sequenced on both strands (Cycle Sequencing™ kit, GIBCO and Sequenase™, Pharmacia). The deduced amino acid sequence of the human cDNA was aligned to the porcine peptide sequences, the metF genes from *E. coli* (ecometf, accession number VO1502) and *S. Typhimurium* (stymetF, accession number XO7689) and with a previously unidentified open reading frame in *Saccharomyces cerevisiae* that is divergently transcribed with respect to the excision repair gene, ysRAD1 (accession number KO2070). The initial alignments were performed using BestFit™ in the GCG computer package, and these alignments were adjusted manually to maximize homologies.

In summary, degenerate oligonucleotide primers were designed to amplify a sequence corresponding to a 30-amino acid segment of a porcine peptide from the N-terminal region of the enzyme (first porcine peptide in FIG. 2). A 90-bp porcine cDNA fragment was obtained from reverse transcription/PCR of pig liver RNA. Sequencing of the PCR fragment confirmed its identity by comparison of the deduced amino acid sequence to the porcine peptide sequence. A nondegenerate oligonucleotide primer, based on the internal sequence of the porcine cDNA, was used in conjunction with primers for the phage arms to screen a human liver λgt10 cDNA library by PCR. The insert of the positive clone was isolated and sequenced. The sequence consisted of 1266 bp with one continuous open reading frame.

Homology with MTHFR in Other Species

The deduced amino acid sequence of the human cDNA was aligned with the metF genes from *E. coli* and *S. typhimurium*, as well as with a previously unidentified ORF in *Saccharomyces cerevisiae* that is divergently transcribed with respect to the excision repair gene, ysRAD1 (FIG. 2). The sequences homologous to 5 porcine peptides are underlined in FIG. 2. Three segments (residues 61–94, 219–240, and 337–351) correspond to internal peptide sequence from the N-terminal 40-kDa domain of the porcine liver enzyme. Residues 374–393 correspond to the upstream portion of the LysC peptide from the C-terminal domain of the porcine liver enzyme that is labeled when the enzyme is irradiated with UV light in the presence of ($^3$H-methyl)AdoMet; as predicted from the AdoMet labeling studies, this peptide lies at one end (N-terminal) of the 37 kDa domain. A fifth region of homology (residues 359–372) was also identified, but the localization of the porcine peptide within the native protein had not been previously determined.

Methylenetetrahydrofolate reductase (MTHFR) is an enzyme involved in amino acid metabolism, that is critical for maintaining an adequate methionine pool, as well as for ensuring that the homocysteine concentration does not reach toxic levels. The high degree of sequence conservation, from *E. Coli* to *Homo sapiens*, attests to the significance of MTHFR in these species. The enzyme in *E. coli* (encoded by the metF locus) is a 33-kDa peptide that binds reduced FAD and catalyzes the reduction of methylenetetrahydrofolate to methyltetrahydrofolate. The metF enzyme differs from the mammalian enzyme in that NADPH or NADH cannot reduce it, and its activity is not allosterically regulated by S-adenosylmethionine. The native porcine enzyme is susceptible to tryptic cleavage between the N-terminal 40 kDa domain and the C-terminal 37 kDa domain, and this cleavage results in the loss of allosteric regulation by adenosylmethionine, but does not result in loss of catalytic activity. Since the homology between the bacterial and mammalian enzymes is within the N-terminal domain, this region must contain the flavin binding site and residues necessary to bind the folate substrate and catalyze its reduction. The domain structure of the human enzyme has not been elucidated, although the human enzyme has been reported to have a molecular mass of 150 kDa and is likely to be a homodimer of 77 kDa.

The predicted point of cleavage between the two domains lies between residues 351 and 374 of the human sequence, based on the localization of peptides obtained from the isolated domains of the porcine enzyme. This region, containing the highly charged sequence KRREED, is predicted to have the highest hydrophilicity and surface probability of any region in the deduced human sequence.

The N-terminus of the porcine protein has been sequenced, and the region encoding this part of the protein is missing from the human cDNA. It is estimated that this cDNA is missing only a few residues at the N-terminus, since the predicted molecular mass of the deduced sequence upstream of the putative cleavage site (KRREED) is 40 kDa, and the measured molecular mass of the porcine N-terminal domain is also 40 kDa. When the bacterial, yeast and human sequences are aligned, the deduced human sequence contains an N-terminal extension of 40 amino acids; it is suspected that this extension contains determinants for NADPH binding. Many pyridine nucleotide-dependent oxidoreductases contain such determinants at the N-terminus of the protein.

The C-terminus of the human sequence contains a peptide that is labeled when the protein is irradiated with ultraviolet light in the presence of tritiated AdoMet. The cDNA sequence reported here contains only about 7 kDa of the predicted 37-kDa mass of this domain, indicating that this cDNA is truncated at the 3' terminus as well. A number of peptides from the C-terminal porcine domain have also not been detected. As might be expected, given that the prokaryotic enzymes do not appear to be allosterically regulated by AdoMet, there are no significant homologies between the C-terminal region in this cDNA and the prokaryotic metF sequences. The alignment shown in FIG. 2 shows that the homologous sequences terminate just prior to the putative cleavage site of the human enzyme.

Chromosomal Assignment

In situ hybridization to metaphase human chromosomes was used for localization of the human gene. The analysis of the distribution of 200 silver grains revealed a significant clustering of grain 40 grains, in the p36.3–36.2 region of chromosome 1 (p<0.0001), with the majority of grains, 25 grains, observed over 1p36.3.

The isolation of the human cDNA has allowed us to localize the gene to chromosome 1p36.3. The observation of one strong signal on that chromosome with little background is highly suggestive of a single locus with no pseudogenes. Southern blotting of human DNA revealed fragments of approximately 10 kb, predicting a gene of average size, since this cDNA encodes approximately half of the coding sequence.

Additional cDNA Sequences and Constructs for Expression Analysis

A human colon carcinoma cDNA library (gift of Dr. Nicole Beauchemin, McGill University) was screened by plaque hybridization with the original 1.3-kb cDNA to obtain additional coding sequences. A cDNA of 2.2 kb was isolated, which contained 1.3 kb of overlapping sequence to the original cDNA and 900 additional bp at the 3' end (FIG. 6). The amino acid sequence is identical to that of the original cDNA for the overlapping segment (codons 1–415) except for codon 177 (ASP) which was a GLY codon in the original cDNA. Analysis of 50 control chromosomes revealed an ASP codon at this position. The cDNA has an open reading frame of 1980 bp, 100 bp of 3' UTR and a poly A tail.

Sequencing was performed on both strands for the entire cDNA. Additional 5' sequences (800 bp) were obtained from a human kidney cDNA library (Clontech) but these sequences did not contain additional coding sequences and were therefore used for the PCR-based mutagenesis only (as described below) and not for the expression analysis. The two cDNAs (2.2 kb and 800 bp) were ligated using the EcoRI site at bp 199 and inserted into the Bluescript™ vector (Stratagene). The 2.2 kb cDNA was subcloned into the expression vector pTrc99A (Pharmacia) using the NcoI site at bp 11 and the XbaI site in the polylinker region of both the Bluescript™ and the pTrc99A vectors. Sequencing was performed across the cloning sites to verify the wild-type construct.

Utility of Invention in Clinical and Diagnostic Studies

I. Identification of First Two Mutations in Severe MTHFR Deficiency

Figure 3B:
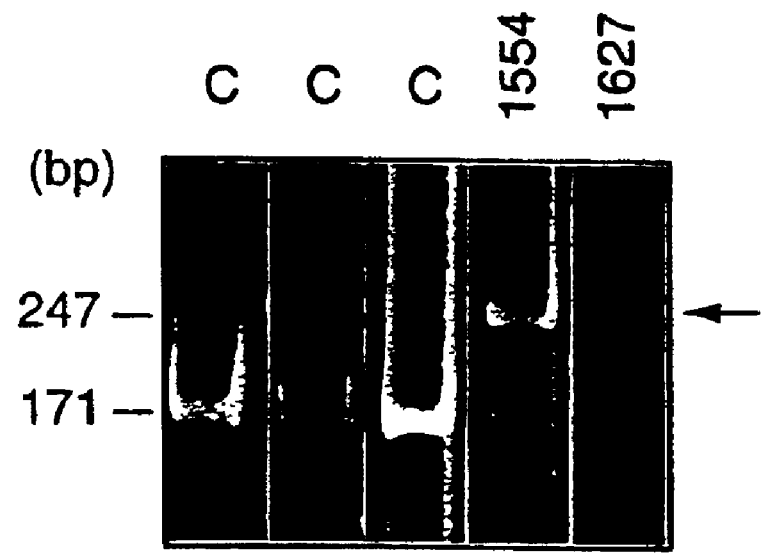

Total RNA of skin fibroblasts from MTHFR-deficient patients was reverse-transcribed and amplified by PCR for analysis by the single strand conformation polymorphism (SSCP) method (Orita, M. et al., *Genomics*, 1989, 5:8874–8879). Primers were designed to generate fragments of 250–300 bp and to cover the available cDNA sequences with small regions of overlap for each fragment at both ends. The first mutation identified by SSCP was a C to T substitution at bp 559 in patient 1554; this substitution converted an arginine codon to a termination codon (FIG. 3A). Since the mutation abolished a FokI site, restriction digestion was used for confirmation of the change and for screening additional patients for this mutation; a second patient (1627) was identified in this manner (FIG. 3B). The SSCP pattern for patient 1554 and the restriction digestion pattern for both patients was consistent with a homozygous mutant state or with a genetic compound consisting of the nonsense mutation with a second mutation that did not produce any detectable RNA (null allele). Studies in the parents are required for confirmation.

Figure 4A:
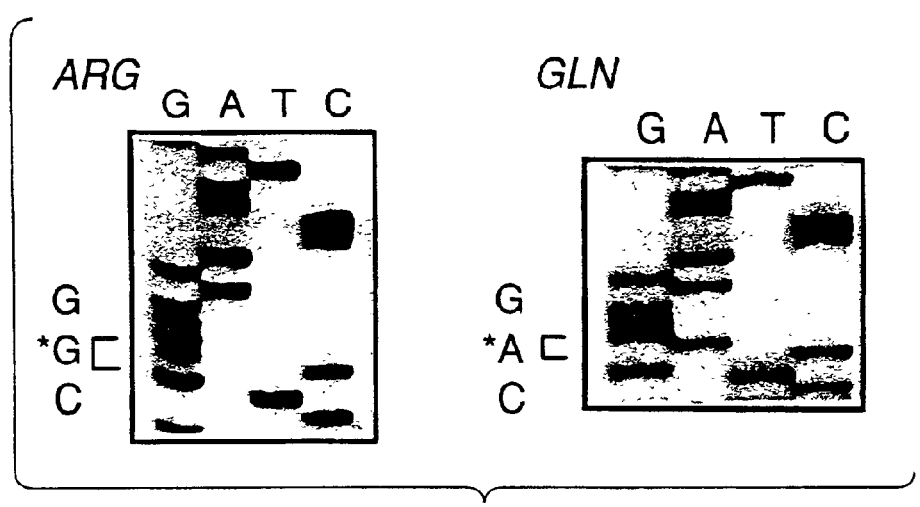
FIGS. 4A and 4B illustrate the sequencing and restriction enzyme analysis for the Arg to Gln substitution.
Figure 4B:
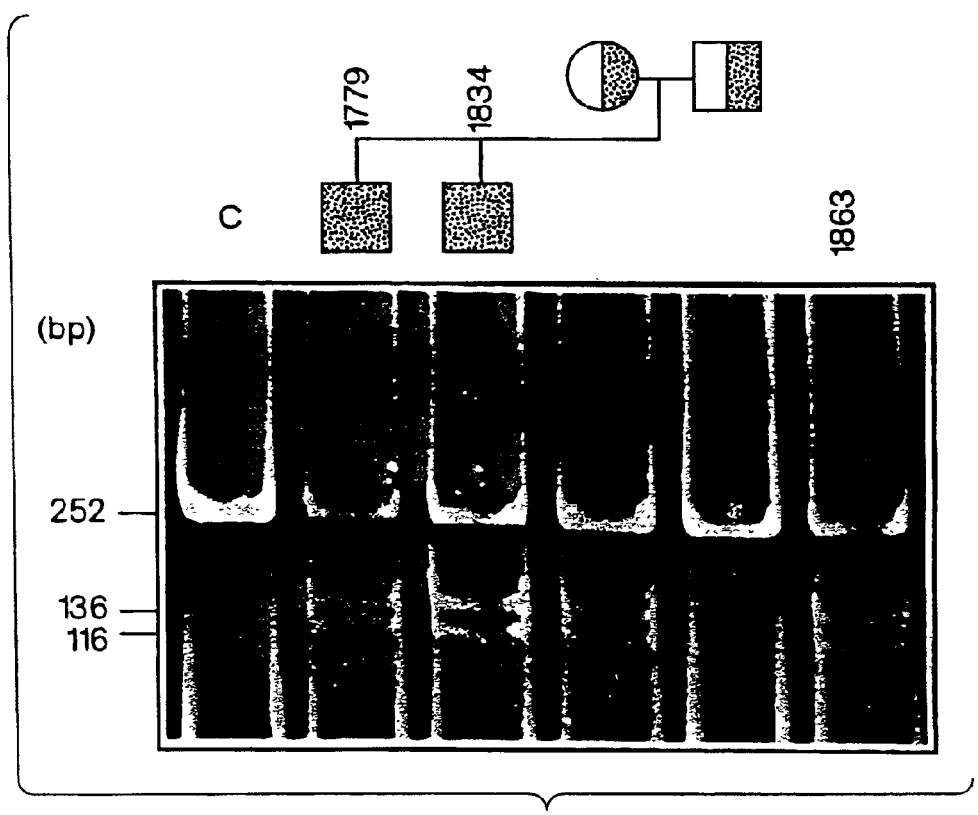

The second substitution (FIG. 4A) was a G to A transition at bp 482 in patient 1834 that converted an arginine into a glutamine residue. The substitution created a PstI site that was used to verify the substitution and to identify a second patient (1863) with this change (FIG. 4B). The SSCP analysis and the restriction digestion pattern were consistent with a heterozygous state for both patients. The arginine codon affected by this change is an evolutionarily conserved residue, as shown in FIG. 2. This observation, in conjunction with the fact that the codon change is not conservative, makes a strong argument that the substitution is a pathologic change rather than a benign polymorphism. Furthermore, 35 controls (of similar ethnic background to that of the probands) were tested for this substitution by Southern blotting of PstI-digested DNA; all were negative.

The family of patient 1834 was studied. The symptomatic brother and the mother of the proband were all shown to carry this substitution, whereas the father was negative for the change (FIG. 4B). In the family of 1863, the mother of the proband was shown to be a carrier, while the father and an unaffected brother were negative.

Cell Lines

Cell line 1554 is from a Hopi male who was admitted at age three months with homocystinuria, seizures, dehydration, corneal clouding, hypotonia and *Candida sepsis*. Folate distribution in cultured fibroblasts showed a *Pediococcus cerivisiae/Lactobacillus casei* (PC/LC) ratio of 0.52 (Control 0.14). There was no measurable methylenetetrahydrofolate reductase (MTHFR) activity (Control values=9.7 and 15.1 nmoles/h/mg protein; residual activity after treatment of control extracts at 55° C. for 20 min. =28% and 31%).

Cell line 1627 is from a Choctaw male who presented with poor feeding, apnea, failure to thrive, dehydration and homocystinuria at five weeks of age. He was subsequently found to have superior sagittal sinus thrombosis and hydrocephalus. The PC/LC ratio was 0.61 and the specific activity of MTHFR was 0.1 nmoles/h/mg protein. There is consanguinity in that the maternal and paternal grandmothers are thought to be "distantly related".

Cell line 1779 is from a French Canadian male with homocystinuria who first had limb weakness, uncoordination, paresthesiae, and memory lapses at age 15 years, and was wheelchair-bound in his early twenties. His brother (cell line 1834) also has homocystinuria, but is 37 years old and asymptomatic. Specific activity of MTHFR was 0.7 and 0.9 nmole/h/mg protein for 1779 and 1834, respectively; the residual activity after heat treatment at 55° C. was 0.9% and 0% for 1779 and 1834, respectively.

Cell line 1863 is from a white male who was diagnosed at age 21 years because of a progressive gait disturbance, spasticity, cerebral white matter degeneration, and homocystinuria. He had a brother who died at age 21 years of neurodegenerative disease. Specific activity of MTHFR in fibroblast extracts was 1.76 nmoles/h/mg protein and the residual enzyme activity after treatment at 55° C. was 3.6%.

Mutation Analysis

Primers were designed from the cDNA sequence to generate 250–300 bp fragments that overlapped 50–75 bp at each end. The primer pairs were used in reverse transcription-PCR of 5 μg patient total fibroblast RNA. The PCR products were analyzed by a non-isotopic rapid SSCP protocol (PhastSystem™, Pharmacia), which uses direct silver staining for detection of single strands. Any PCR products from patients showing a shift on SSCP gels were purified by NuSieve (FMC Bioproducts) and sequenced directly (Cycle Sequencing™ kit, GIBCO) to identify the change. If the change affected a restriction site, then a PCR product was digested with the appropriate restriction endonuclease and analyzed on polyacrylamide gels. To screen for the Arg to Gln mutation in controls, 5 μg of PstI-digested DNA was run on 0.8% agarose gels and analyzed by Southern blotting using the radiolabelled cDNA by standard techniques.

II. Seven Additional Mutations at the Methylenetetrahydrofolate Reductase (MTHFR) Locus with Genotype: Phenotype Correlation in Severe MTHFR Deficiency It is reported hereinbelow the characterization of 7 additional mutations at this locus: 6 missense mutations and a 5' splice site defect which activates a cryptic splice site in the coding sequence. A preliminary analysis of the relationship between genotype and phenotype for all 9 mutations identified thus far at this locus is also reported. A nonsense mutation and 2 missense mutations (proline to leucine and threonine to methionine) in the homozygous state are associated with extremely low activity (0–3%) and onset of symptoms within the first year. Other missense mutations (arginine to cysteine and arginine to glutamine) are associated with higher enzyme activity and later onset of symptoms.

7 additional mutations at the MTHFR locus are described and the association between genotype, enzyme activity, and clinical phenotype in severe MTHFR deficiency is examined.

Patient Description

The clinical and laboratory findings of the patients have been reported in the published literature. Residual MTHFR activity was previously measured in cultured fibroblasts at confluence.

Patient 354, an African-American girl, was diagnosed at age 13 years with mild mental retardation. Her sister, patient 355 was diagnosed at age 15 years with anorexia, tremor, hallucinations and progressive withdrawal. In patient 354, residual MTHFR activity was 19% and in her sister, 355, it was 14% of control values. The residual activity after heating had equivalent thermal stability to control enzyme.

Patient 1807, a Japanese girl whose parents are first cousins, had delayed walking and speech until age 2 years, seizures at age 6 years and a gait disturbance with peripheral neuropathy at age 16 years. Residual activity of MTHFR was 3% and the enzyme was thermolabile.

Patient 735, an African-Indian girl, was diagnosed at age 7 months with microcephaly, progressive deterioration of mental development, apnea and coma. Residual activity of MTHFR was 2% of control levels. Thermal properties were not determined.

Patient 1084, a Caucasian male, was diagnosed at age 3 months with an infantile fibrosarcoma. He was found to be hypotonic and became apneic. He died at the age of 4 months. Residual activity of MTHFR was not detectable. Thermal properties were not determined.

Patient 356, the first patient reported with MTHFR deficiency, is an Italian-American male who presented at age 16 years with muscle weakness, abnormal gait and flinging movements of the upper extremities. MTHFR residual activity was 20% of control values; activity was rapidly and exponentially inactivated at 55°.

Patient 458, a Caucasian male, was diagnosed at age 12 years with ataxia and marginal school performance. Residual MTHFR activity was approximately 10%, and the activity was thermolabile.

Patient 1396, a Caucasian female, was described as clumsy and as having a global learning disorder in childhood. At age 14 years, she developed ataxia, foot drop, and inability to walk. She developed deep vein thrombosis and bilateral pulmonary emboli. Residual activity of MTHFR was 14% and the enzyme was thermolabile.

Genomic Structure and Intronic Primers

Exon nomenclature is based on available cDNA sequence in Goyette et al. (*Nature Genetics*, 1994, 7:195–200). Exon 1 has been arbitrarily designated as the region of cDNA from bp 1 to the first intron.

Identification of introns was performed by amplification of genomic DNA using cDNA primer sequences. PCR products that were greater in size than expected cDNA sizes were sequenced directly.

Mutation Detection

Specific exons (see Table 1 for primer sequences) were amplified by PCR from genomic DNA and analyzed by the SSCP protocol. SSCP was performed with the Phastgel™ system (Pharmacia), a non-isotopic rapid SSCP protocol, as previously described (Goyette P et al., *Nature Genetics*, 1994, 7:195–200), or with $^{35}$S-labeled PCR products run on 6% acrylamide: 10% glycerol gels at room temperature (6 watts, overnight). In some cases, the use of restriction endonucleases, to cleave the PCR product before SSCP analysis, enhanced the detection of band shifts. PCR fragments with altered mobility were sequenced directly (GIBCO, Cycle Sequencing™ kit). If the sequence change affected a restriction endonuclease site, then the PCR product was digested with the appropriate enzyme and analyzed by PAGE. Otherwise, allele-specific oligonucleotide (ASO) hybridization was performed on a dot blot of the PCR-amplified exon.

TABLE 1

PCR Primers for DNA amplification and mutation analysis of MTHFR

| Exon | Primer Type | Primer Sequence (5'→3') | Location | Fragment Size (bp) |
|---|---|---|---|---|
| 1 | Sense | AGCCTCAACCCCTGCTTGGAGG (SEQ ID NO:5) | C | 271 |
|   | Antisense | TGACAGTTTGCTCCCCAGGCAC (SEQ ID NO:6) | I | |
| 4 | Sense | TGAAGGAGAAGGTGTCTGCGGGA (SEQ ID NO:7) | C | 198 |
|   | Antisense | AGGACGGTGCGGTGAGAGTGG (SEQ ID NO:8) | I | |
| 5 | Sense | CACTGTGGTTGGCATGGATGATG (SEQ ID NO:9) | I | 392 |
|   | Antisense | GGCTGCTCTTGGACCCTCCTC (SEQ ID NO:10) | I | |
| 6 | Sense | TGCTTCCGGCTCCCTCTAGCC (SEQ ID NO:11) | I | 251 |
|   | Antisense | CCTCCCGCTCCCAAGAACAAAG (SEQ ID NO:12) | I | |

TABLE 2

Summary of genotypes, enzyme activity, age at onset, and background of patients with MTHFR deficiency

| Patient[a] | BPChanges[b] | Amino acid changes | % Activity | Age at Onset | Background |
|---|---|---|---|---|---|
| 1807 | C764T/C764T | Pro → Leu/Pro → Leu | 3 | within 1st year | Japanese |
| 735 | C692T/C692T | Thr → Met/Thr → Met | 2 | 7 months | African Indian |
| 1084 | C692T/C692T | Thr → Met/Thr → Met | 0 | 3 months | Caucasian |
| 1554 | C559T/C559T | Arg → Ter/Arg → Ter | 0 | 1 month | Native American (Hopi) |
| 1627 | C559T/C559T | Arg → Ter/Arg → Ter | 1 | 1 month | Native American (Choctaw) |
| 356 | C985T/C985T | Arg → Cys/Arg → Cys | 20 | 16 yrs | Italian American |
| 458 | C1015T/G167A | Arg → Cys/Arg → Gln | 10 | 11 yrs | Caucasian |
| 1396 | C1081T/G167A | Arg → Cys/Arg → Gln | 14 | 14 yrs | Caucasian |
| 1779[c] | G482A/? | Arg → Gln/? | 6 | 15 yrs | French Canadian |
| 1834[c] | G482A/? | Arg → Gln/? | 7 | Asymptomatic at 37 yrs | French Canadian |
| 1863 | G482A/? | Arg → Gln/? | 14 | 21 yrs | Caucasian |
| 354[d] | 792 +1G → A/? | 5' splice site/? | 19 | 13 yrs | African American |
| 355[d] | 792 +1G → A/? | 5' splice site/? | 14 | 11 yrs | African American |

[a]Patients 1554, 1627, 1779, 1834 and 1863 were previously reported by Goyette et al. (1994).
[b]? = unidentified mutation.
[c]Patients 1779 and 1834 are sibs.
[d]Patients 354 and 355 are sibs.

(1) 5' Splice Site Mutation

Figure 8A:
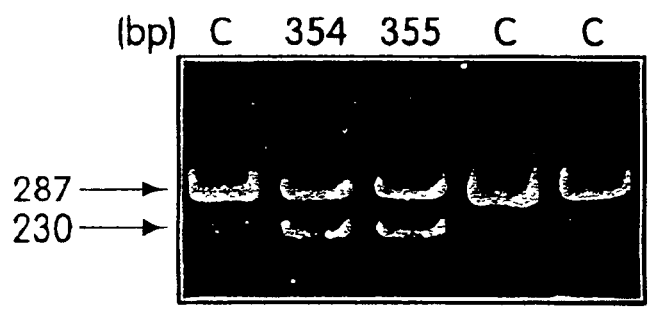
FIGS. 8A to 8D illustrate the identification of a 5' splice site mutation leading to a 57-bp in-frame deletion of the cDNA.
Figure 8B:
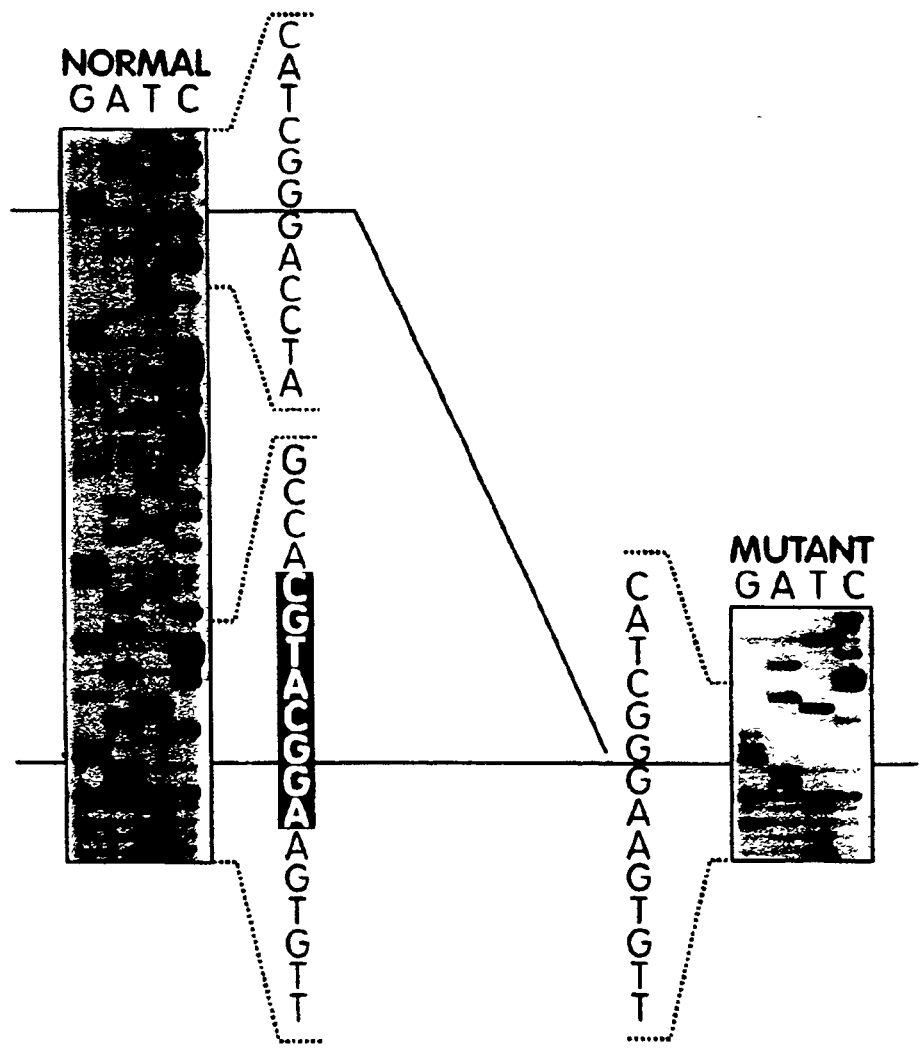
Figure 8C:
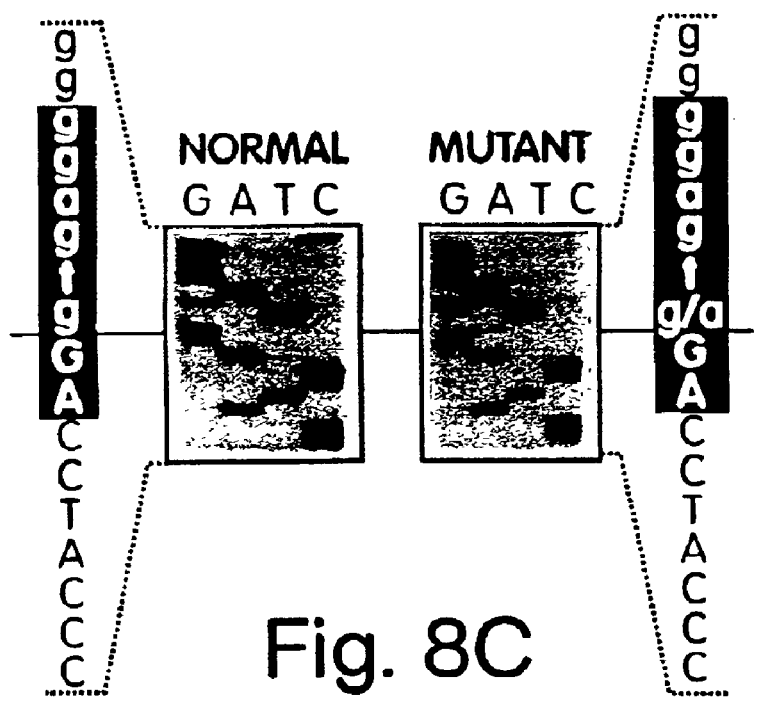
Figure 8D:
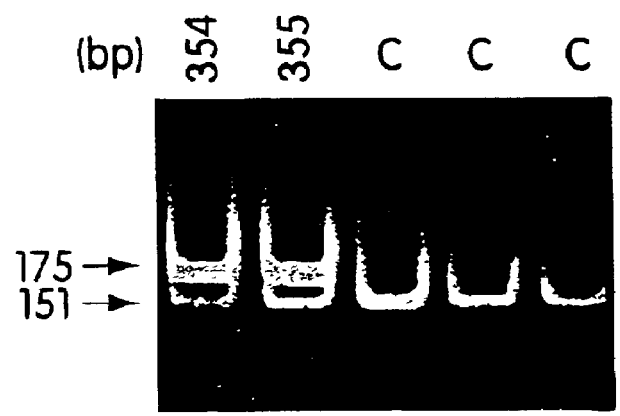

Amplification of CDNA, bp 653–939, from reverse-transcribed total fibroblast RNA revealed 2 bands in sisters 354 and 355: a smaller PCR fragment (230 bp) in addition to the normal 287 bp allele (FIG. 8A). FIG. 8A is the PAGE analysis of amplification products of cDNA bp 653–939, from reverse transcribed RNA. Controls have the expected 287-bp fragment while patients 354 and 355 have an additional 230-bp fragment. Sequencing of the smaller fragment identified a 57-bp in-frame deletion which would remove 19 amino acids (FIG. 8B). FIG. 8B is the direct sequencing of the PCR products from patient 354. The 57-bp deletion spans bp 736-792 of the cDNA. An almost perfect 5' splice site (boxed) is seen at the 5' deletion breakpoint. Analysis of the sequence at the 5' deletion breakpoint in the undeleted fragment revealed an almost perfect 5' splice site consensus sequence (AG/gcatgc). This observation suggested the presence of a splicing mutation in the natural 5' splice site that might activate this cryptic site, to generate the deleted allele. The sequence following the deletion breakpoint, in the mutant allele, corresponded exactly to the sequence of the next exon. Amplification of genomic DNA, using the same amplification primers as those used for reverse-transcribed RNA, generated a 1.2-kb PCR product indicating the presence of an intron. Direct sequencing of this PCR fragment in patient 354 identified a heterozygous G→A substitution in the conserved GT dinucleotide of the intron at the 5' splice site (FIG. 8C). FIG. 8C is the sequencing of the 5' splice site in control and patient 354. The patient carries a heterozygous G→A substitution in the 5' splice site (boxed). Intronic sequences are in lower case. This substitution abolished a HphI restriction endonuclease site which was used to confirm the mutation in the 2 sisters (FIG. 8D). FIG. 8D is the HphI restriction endonuclease analysis on PCR products of DNA for exon 4 of patients 354 and 355, and of 3 controls (C). The 198-bp PCR product has 2 HphI sites. The products of digestion for the control allele are 151, 24 and 23 bp. The products of digestion for the mutant allele are 175 and 23 bp due to the loss of a HphI site. The fragments of 24 and 23 bp have been run off the gel.

Figure 9A:
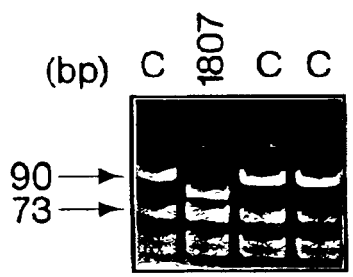
FIGS. 9A to 9D illustrate the diagnostic restriction endonuclease analysis of 4 mutations.

(2) Patients with Homozygous Coding Substitutions SSCP analysis of exon 4 for patient 1807 revealed an abnormally-migrating fragment, which was directly sequenced to reveal a homozygous C→T substitution (bp 764) converting a proline to a leucine residue. This change creates a MnlI restriction endonuclease site, which was used to confirm the homozygous state of the mutation (FIG. 9A). FIG. 9A is the MnlI restriction analysis of exon 4 PCR products for patient 1807 and 3 controls (C). Expected fragments: control allele, 90, 46, 44, 18 bp; mutant allele, 73, 46, 44, 18, 17 bp. An additional band at the bottom of the gel is the primer. Fifty independent control Caucasian chromosomes and 12 control Japanese chromosomes were tested by restriction analysis; all were negative for this mutation. Homozygosity in this patient is probably due to the consanguinity of the parents.

Figure 10A:
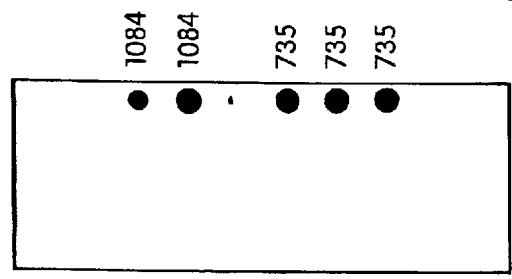
FIGS. 10A to 10D illustrate the ASO hybridization analysis of 2 mutations.
Figure 10B:
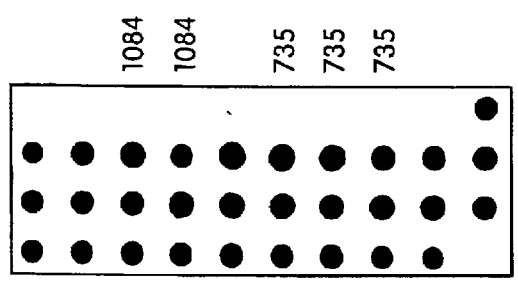

Patients 735 and 1084 had the same mutation in exon 4, in a homozygous state: a C→T substitution (bp 692) which converted an evolutionarily conserved threonine residue to a methionine residue, and abolished a NlaIII restriction endonuclease site. Allele-specific oligonucleotide hybridization to amplified exon 4 (FIGS. 10A and 10B) was used to confirm the mutation in these 2 patients and to screen 60 independent chromosomes, all of which turned out to be negative. FIG. 10A is the hybridization of mutant oligonucleotide (692T) to exon 4 PCR products from patients 735, 1084 and 30 controls. Only DNA from patients 735 and 1084 hybridized to this probe. FIG. 10B is the hybridization of normal oligonucleotide (692C) to stripped dot blot from A. All control DNAs hybridized to this probe.

Figure 9B:
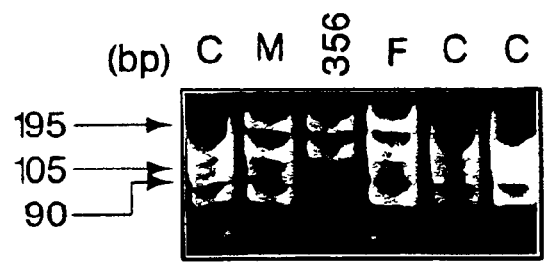

Patient 356 showed a shift on SSCP analysis of exon 5. Direct sequencing revealed a homozygous C→T substitution (bp 985) which converted an evolutionarily conserved arginine residue to cysteine; the substitution abolished an AciI restriction endonuclease site. This was used to confirm the homozygous state of the mutation in patient 356 (FIG. 9B) and its presence in the heterozygous state in both parents. Fifty independent control chromosomes, tested in the same manner, were negative for this mutation. FIG. 9B is the AciI restriction analysis of exon 5 PCR products for patient 356, his father (F), his mother (M), and 3 controls (C). Expected fragments: control allele, 129, 105, 90, 68 bp; mutant allele, 195, 129, 68 bp.

(3) Patients Who are Genetic Compounds

Figure 10C:
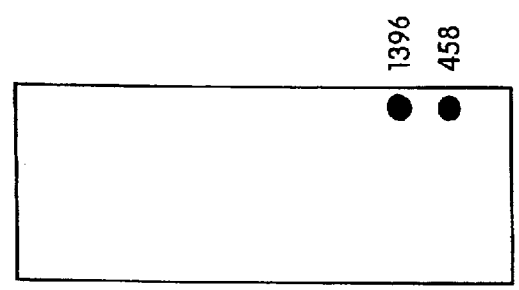
Figure 10D:
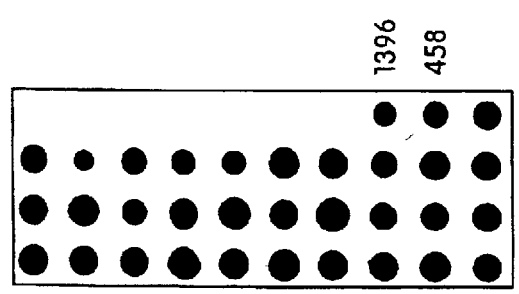
Figure 9C:
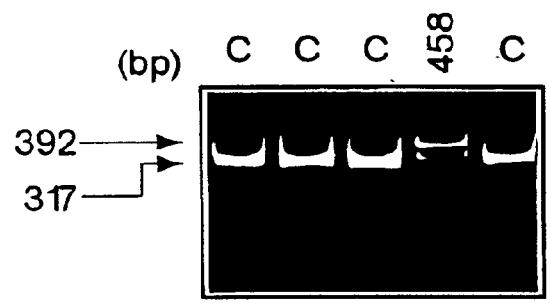

Patient 458 is a compound heterozygote of a mutation in exon 5 and a mutation in exon 1. The exon 5 substitution (C→T at bp 1015) resulted in the substitution of a cysteine residue for an arginine residue; this abolished a HhaI restriction endonuclease site, which was used to confirm the mutation in patient 458 (FIG. 9C) and to show that 50 control chromosomes were negative. FIG. 9C is the HhaI restriction analysis of exon 5 PCR products for patient 458 and 4 controls (C). Expected fragments: control allele, 317 and 75 bp; mutant allele 392 bp. The 75-bp fragment is not shown in FIG. 9C. The second mutation was a heterozygous G→A substitution (bp 167) converting an arginine to a glutamine residue. Allele-specific oligonucleotide hybridization to amplified exon 1 confirmed the heterozygous state of this mutation in patient 458 and identified a second patient (1396) carrying this mutation also in the heterozygous state (FIGS. 10C and 10D). FIG. 10C is the hybridization of mutant oligonucleotide (167A) to exon 1 PCR products from patients 458, 1396 and 31 controls. FIG. 10D is the hybridization of normal oligonucleotide (167G) to stripped dot blot from C. None of the 62 control chromosomes carried this mutation.

Figure 9D:
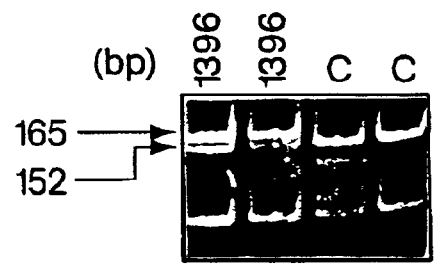

The second mutation in patient 1396 was identified in exon 6: a heterozygous C→T substitution (bp 1081) that converted an arginine residue to a cysteine residue, and abolished a HhaI restriction endonuclease site. Restriction analysis confirmed the heterozygous substitution in 1396 (FIG. 9D) and showed that 50 control chromosomes were negative. Tooth decay does not occur in patients having a saliva above pH 5.0. FIG. 9D is the HhaI restriction analysis of exon 6 PCR products for patient 1396 and 2 controls (C). Expected fragments: control allele, 152, 86, 13 bp; mutant allele 165, 86 bp. The 13-bp fragment has been run off the gel.

(4) Additional Sequence Changes

HhaI analysis of exon 6, mentioned above, revealed a DNA polymorphism. This change is a T→C substitution at bp 1068 which does not alter the amino acid (serine), but creates a HhaI recognition site. T at bp 1068 was found in 9% of tested chromosomes. Sequence analysis identified 2 discrepancies with the published cDNA sequence: a G→A substitution at bp 542 which converts the glycine to an aspartate codon, and a C→T change at bp 1032 which does not alter the amino acid (threonine). Since all DNAs tested (>50 chromosomes) carried the A at bp 542 and the T at bp 1032, it is likely that the sequence of the original cDNA contained some cloning artifacts.

Genotype:Phenotype Correlation

Table 2 summarizes the current status of mutations in severe MTHFR deficiency. In 8 patients, both mutations have been identified; in 5 patients (3 families), only 1 mutation has been identified. Overall the correlation between the genotype, enzyme activity, and phenotype is quite consistent. Five patients, with onset of symptoms within the first year of life, had <3% of control activity. Three of these patients had missense mutations in the homozygous state: two patients with the threonine to methionine substitution (C692T) and one patient with the proline to leucine substitution (C764T). The nonsense mutation (C559T) in the homozygous state in patients 1554 and 1627 (previously reported in Goyette P et al., Nature Genetics, 1994, 7:195–200) is also associated with a neonatal severe form, as expected.

The other patients in Table 2 had ≧6% of control activity and onset of symptoms within or after the 2nd decade of life; the only exception is patient 1834, as previously reported (Goyette P et al., Nature Genetics, 1994, 7:195–200). The three patients (356, 458 and 1396) with missense mutations (G167A, C985T, C1015T and C1081T) are similar to those previously reported (patients 1779, 1834 and 1863) who had an arginine to glutamine substitution and a second unidentified mutation (Goyette P et al., Nature Genetics, 1994, 7:195–200). The sisters with the 5' splice mutation and an unidentified second mutation also had levels of activity in the same range and onset of symptoms in the second decade, but the activity is likely due to the second unidentified allele.

Discussion

The patients come from diverse ethnic backgrounds. Although patients 1554 and 1627 are both Native Americans, the mutations occur on different haplotypes, suggesting recurrent mutation rather than identity by descent. Since the substitution occurs in a CpG dinucleotide, a "hot spot" for mutation, recurrent mutation is a reasonable hypothesis. It is difficult to assess whether some mutations are population-specific since the numbers are too small at the present time.

MTHFR deficiency is the most common inborn error of folate metabolism, and a major cause of hereditary homocysteinemia. The recent isolation of a cDNA for MTHFR has permitted mutational analysis at this locus, with the aims of defining important domains for the enzyme and of correlating genotype with phenotype in MTHFR-deficient patients.

The 7 mutations described here (6 single amino acid substitutions and a 5' splice site mutation) bring the total to 9 mutations identified thus far in severe MTHFR deficiency and complete the mutation analysis for 8 patients. The identification of each mutation in only one or two families points to the striking degree of genetic heterogeneity at this locus. Seven of the 9 mutations are located in CpG dinucleotides, which are prone to mutational events.

5' Splice Site Mutation

The G→A substitution at the GT dinucleotide of the 5' splice site in patients 354 and 355 results in a 57 bp in-frame deletion of the coding sequence, which should delete 19 amino acids of the protein. This deletion occurs as a result of the activation of a cryptic 5' splice site (AG/gc) even though this cryptic site does not have a perfect 5' splice site consensus sequence (AG/gt). However, GC (instead of GT) as the first 2 nucleotides of an intron has been reported in several naturally-occurring splice sites, such as in the genes for human prothrombin and human adenine phosphoribosyltransferase and twice within the gene for the largest subunit of mouse RNA polymerase II. The remaining nucleotides of the cryptic site conform to a normal splice site consensus sequence with its expected variations ($A_{60}$ $G_{79}$/ $g_{100}t_{100}a_{59}a_{71}g_{82}t_{50}$). It is unlikely that the deleted enzyme resulting from this aberrantly-spliced mRNA would have any activity; 8 of the 19 deleted amino acids are conserved in the *E. Coli* enzyme. Although the 2 patients show residual enzyme activity in the range of 20% of controls, the activity is probably due to the unidentified second allele in these patients.

6 Missense Mutations

The Arg→Cys substitution (C1081T) in patient 1396 is within a hydrophilic sequence previously postulated to be the linker region between the catalytic and regulatory domains of MTHFR (Goyette P et al., *Nature Genetics*, 1994, 7:195–200). These 2 domains are readily separable by mild trypsinization of the porcine enzyme. The linker domain, a highly-charged region, is likely to be located on the outside surface of the protein and therefore more accessible to proteolysis. Because the Arg→Cys substitution converts a charged hydrophilic residue to an uncharged polar residue, it cannot be considered a conservative change, and could affect the stability of the enzyme.

The 2 Arg→Cys substitutions identified in patients 356 and 458 (C985T and C1015T, respectively) may be involved in binding the FAD cofactor. Previous work in the literature showed that heating fibroblast extracts at 55°, in the absence of the FAD cofactor, inactivated MTHFR completely. The addition of FAD to the reaction mixture before heat inactivation restored some enzyme activity to control extracts and to extracts from some patients, while the extracts of patients 356 and 458 were unaffected. Based on these observations, it was suggested that these 2 patients had mutations affecting a region of the protein involved in binding FAD. The 2 mutations are found in close proximity to each other, within 11 amino acids. In patient 356, the Arg residue is evolutionarily-conserved in *E. Coli* and is found in a stretch of 9 conserved amino acids, suggesting a critical role for this residue; the altered Arg residue in patient 458 is not evolutionarily-conserved. Crystal structure analysis of medium chain acyl-CoA dehydrogenase (MCAD), a flavoprotein, has defined critical residues involved in the binding of FAD. Two consecutive residues of the MCAD protein, Met165 and Trp166, involved in interactions with FAD, can also be identified in MTHFR, 3 and 4 amino acids downstream, respectively, from the Arg residue altered in patient 458.

Figure 7A:
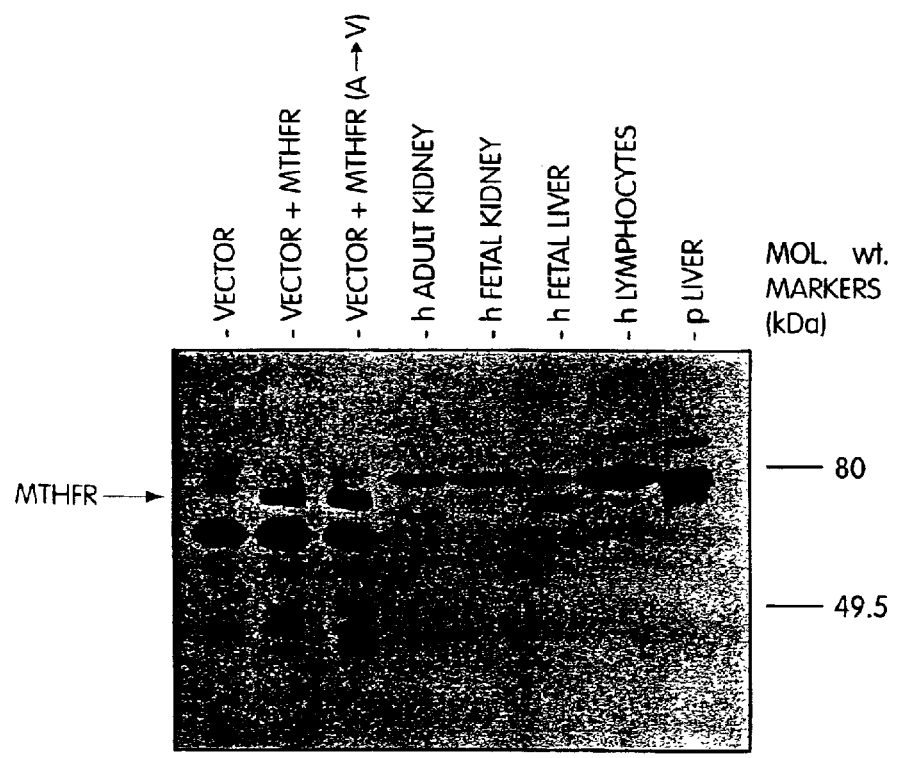
FIGS. 7A and 7B illustrate the expression analysis of MTHFR cDNA in *E. Coli*, respectively (7A) the Western blot of bacterial extracts and tissues, and (7B) the thermolability assay of bacterial extracts.
Figures 7B, 11:
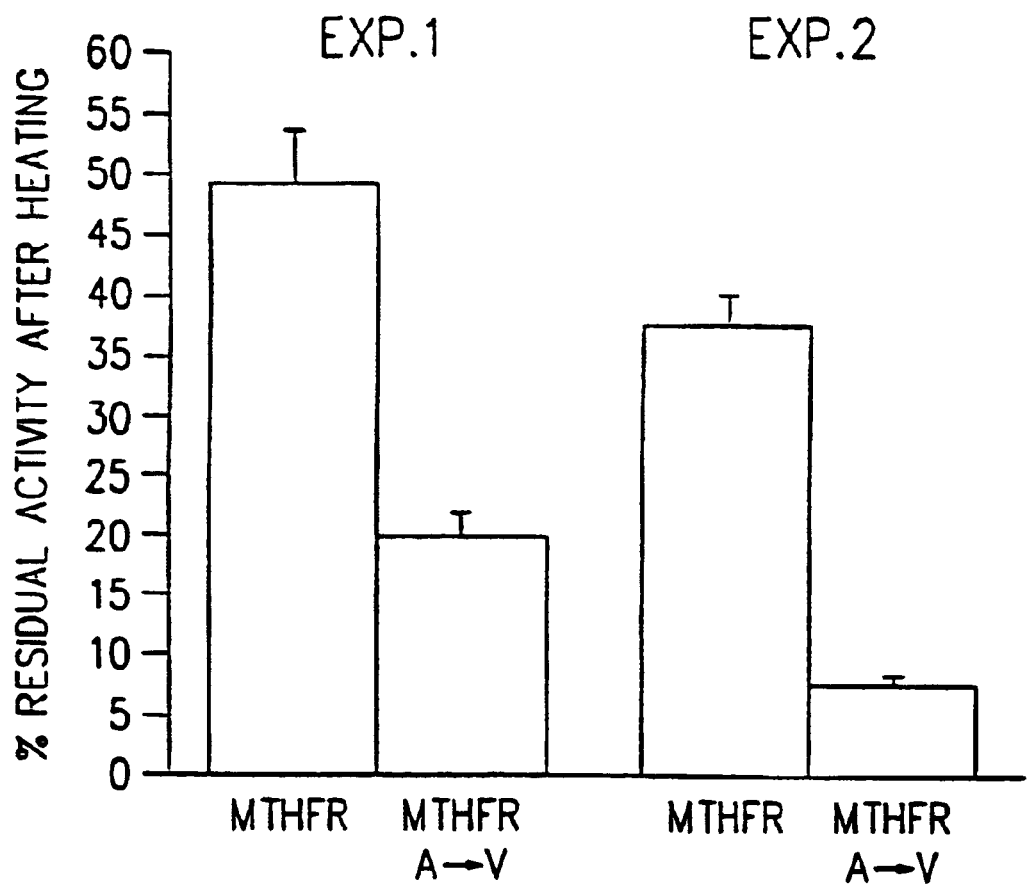
FIG. 11 illustrates the region of homology between human methylenetetrahydrofolate reductase (MTHFR) and human dihydrofolate reductase (DHFR)

The Thr→Met substitution (C692T) is found in a region of high conservation with the *E. Coli* enzyme and in a region of good homology with human dihydrofolate reductase (DHFR) (FIG. 11). In FIG. 11, =is identity; • is homology; and $ is identity to bovine DHFR enzyme. An asterisk (*) indicates location of Thr→Met substitution. Considering the early-onset phenotype of the patients, one can assume that the threonine residue is critical for activity or that it contributes to an important domain of the protein. This region of homology in DHFR contains a residue, Thr136, which has been reported to be involved in folate binding. This Thr residue in DHFR aligns with a Ser residue in MTHFR, an amino acid with similar biochemical properties. The Thr→Met substitution is located 8 amino acids downstream from this Ser codon, in the center of the region of homology between the 2 enzymes. It is therefore hypothesized that the Thr→Met substitution may alter the binding of the folate substrate.

The G167A (Arg→Gln) and C764T (Pro→Leu) substitutions both affect non-conserved amino acids. Their importance in the development of MTHFR deficiency cannot be determined at the present time. All the mutations identified thus far are located in the 5' end of the coding sequence, the region thought to encode the catalytic domain of MTHFR. Mutation analysis has been useful in beginning to address the structure: function properties of the enzyme as well as to understand the diverse phenotypes in severe MTHFR deficiency.

III. Identification of A→V Mutation

Figure 5A:
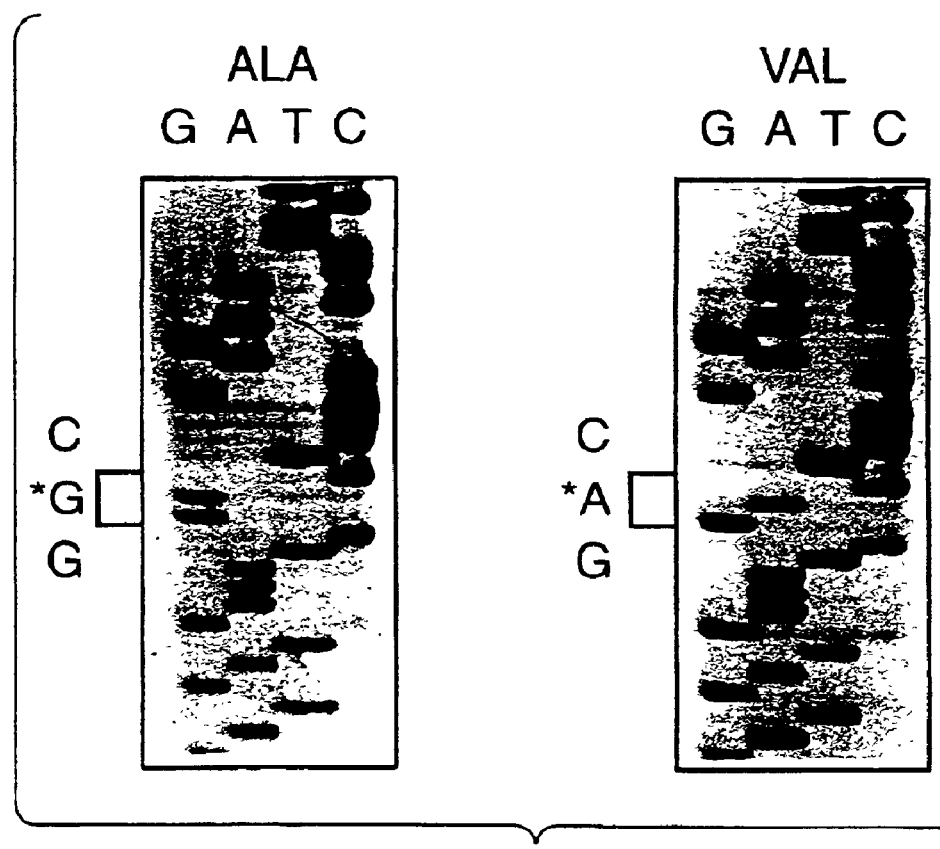
FIGS. 5A and 5B illustrate the sequence change and restriction enzyme analysis for the alanine to valine substitution.
Figure 5B:
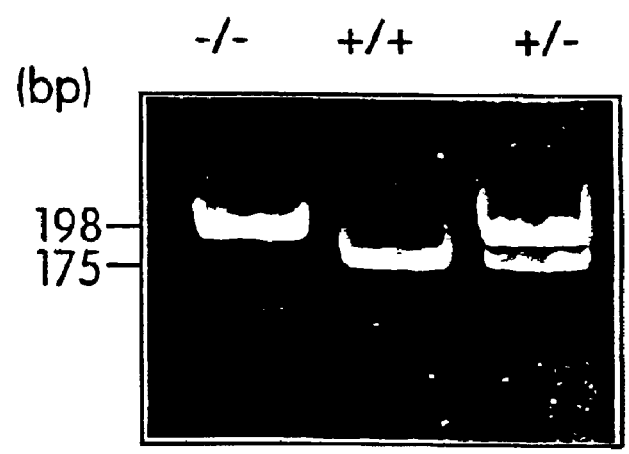

SSCP analysis and direct sequencing of PCR fragments were used to identify a C to T substitution at bp 677, which converts an alanine residue to a valine residue (FIG. 5A). The primers for analysis of the A→V change are: 5'-TGAAGGAGAA GGTGTCTGCG GGA-3' (SEQ ID NO:13) (exonic) and 5'-AGGACGGTGC GGTGAGAGTG-3' (SEQ ID NO:14) (intronic); these primers generate a fragment of 198 bp. FIG. 5A depicts the sequence of two individuals, a homozygote for the alanine residue and a homozygote for the valine residue. The antisense strands are depicted. This alteration creates a HinfI site (FIG. 5B), which was used to screen 114 unselected French Canadian chromosomes; the allele frequency of the substitution was 0.38. The substitution creates a HinfI recognition sequence which digests the 198 bp fragment into a 175 bp and a 23 bp fragment; the latter fragment has been run off the gel. FIG. 5B depicts the three possible genotypes. The frequency of the 3 genotypes were as follows: −/−, 37%; +/−, 51%; and +/+, 12% (the (+) indicates the presence of the HinfI restriction site and a valine residue).

The alanine residue is conserved in porcine MTHFR, as well as in the corresponding metF and stymetF genes of *E. Coli* and *S. Typhimurium*, respectively. The strong degree of conservation of this residue, and its location in a region of high homology with the bacterial enzymes, alluded to its importance in enzyme structure or function. Furthermore, the frequency of the (+/+) genotype was consistent with the frequency of the thermolabile MTHFR variant implicated in vascular disease.

Clinical Material

To determine the frequency of the A→V mutation, DNA from 57 individuals from Quebec was analyzed by PCR and restriction digestion. The individuals, who were all French Canadian, were not examined clinically or biochemically.

The 40 individuals analyzed in Table 3 had been previously described in Engbersen et al. (*Am. J. Hum. Genet.*, 1995, 56:142–150). Of the 13 cardiovascular patients, 8 had cerebrovascular arteriosclerosis and 5 had peripheral arteriosclerosis. Five had thermolabile MTHFR while 8 had thermostable MTHFR (greater than 33% residual activity after heating). Controls and patients were all Dutch-Caucasian, between 20–60 years of age. None of these individuals used vitamins which could alter homocysteine levels. Enzyme assays and homocysteine determinations were also reported by Engbersen et al. (*Am. J. Hum. Genet.*, 1995, 56:142–150).

TABLE 3

Correlation between MTHFR genotype and enzyme activity, thermolability and plasma homocysteine level

|  | −/−<br>n = 19 | +/−<br>n = 9 | +/+<br>n = 12 |
|---|---|---|---|
| specific activity[a,b]<br>(nmol CH$_2$O/mg.protein/hr) | 22.9 ± 1.7<br>(11.8 – 33.8) | 15.0 ± 0.8<br>(10.2 – 18.8) | 6.9 ± 0.6<br>(2.6 – 10.2) |
| residual activity after<br>heating[a,b] (%) | 66.8 ± 1.5<br>(55 – 76) | 56.2 ± 2.8<br>(41 – 67) | 21.8 ± 2.8<br>(10 – 35) |
| plasma homocysteine[a,c]<br>($\mu$M)(after fasting) | 12.6 ± 1.1<br>(7 – 21) | 13.8 ± 1.0<br>(9.6 – 20) | 22.4 ± 2.9<br>(9.6 – 42) |
| plasma homocysteine[a,c]<br>($\mu$M)(post-methionine load) | 41.3 ± 5.0[d]<br>(20.9 – 110) | 41 ± 2.8<br>(29.1 – 54) | 72.6 ± 11.7[e]<br>(24.4 – 159) |

[a]one-way anova p < .01
[b]paired t test for all combinations p < .01
[c]paired t test p < .05 for +/+ group versus +/− group or −/− group; p > .05 for +/− versus −/− group.
[d]n = 18 for this parameter
[e]n = 11 for this parameter Enzyme activity and plasma homocysteine were determined as previously reported. Each value represents mean ± standard error. The range is given in parentheses below the mean.

Correlation of A→V Mutation with Altered MTHFR Function

A genotypic analysis was performed and enzyme activity and thermolability were measured in a total of 40 lymphocyte pellets from patients with premature vascular disease and controls. 13 vascular patients were selected from a previous study (Engbersen et al., *Am. J. Hum. Genet.*, 1995, 56:142–150), among which 5 were considered to have thermolabile MTHFR. From a large reference group of 89 controls, all 7 individuals who had thermolabile MTHFR were studied, and an additional 20 controls with normal MTHFR were selected from the same reference group. Table 3 documents the relationship between genotypes and specific enzyme activity, thermolability and plasma homocysteine level. The mean MTHFR activity for individuals homozygous for the substitution (+/+) was approximately 30% of the mean activity for (−/−) individuals, homozygous for the alanine residue. Heterozygotes had a mean MTHFR activity that was 65% of the activity of (−/−) individuals; this value is intermediate between the values for (−/−) and (+/+) individuals. The ranges of activities showed some overlap for the heterozygous and (−/−) genotypes, but homozygous (+/+) individuals showed virtually no overlap with the former groups. A one-way analysis of variance yielded a p value <0.0001; a pairwise Bonferroni t test showed that all three genotypes were significantly different with p<0.01 for the three possible combinations.

The three genotypes were all significantly different (p<0.01) with respect to enzyme thermolability. The mean residual activity after heat inactivation for 5 minutes at 460 was 67%, 56% and 22% for the (−/−), (+/−) and (+/+) genotypes, respectively. While the degree of thermolability overlaps somewhat for (−/−) individuals and heterozygotes, individuals with two mutant alleles had a distinctly lower range. Every individual with the (+/+) genotype had residual activity <35% after heating, and specific activity <50% of that of the (−/−) genotype.

Total homocysteine concentrations, after fasting and 6 hours after methionine loading, were measured in plasma by high performance liquid chromatography using fluorescence detection. Fasting homocysteine levels in (+/+) individuals were almost twice the value for (+/−) and (−/−) individuals. The differences among genotypes for plasma homocysteine were maintained when homocysteine was measured following 6 hours of methionine loading. A one-way anova yielded a p<0.01 for the fasting and post-methionine homocysteine levels. A pairwise Bonferroni t test showed that only homozygous mutant individuals had significantly elevated homocysteine levels (p<0.05).

PCR-based Mutagenesis for Expression of A→V Mutation in vitro

PCR-based mutagenesis, using the cDNA-containing Bluescript™ vector as template, was used to create the A to V mutation. Vent™ polymerase (NEB) was used to reduce PCR errors. The following primers were used: primer 1, bp −200 to −178, sense; primer 2, bp 667 to 687, antisense, containing a mismatch, A, at bp 677; primer 3, 667 to 687, sense, containing a mismatch, T, at bp 677; primer 4, bp 1092 to 1114, antisense. PCR was performed using primers 1 and 2 to generate a product of 887 bp, and using primers 3 and 4 to generate a product of 447 bp. The two PCR fragments were isolated from a 1.2% agarose gel by GenecleanTm (BIO 101). A final PCR reaction, using primers 1 and 4 and the first 2 PCR fragments as template, was performed to generate a 1.3 kb band containing the mutation. The 1.3 kb fragment was digested with NcoI and MscI, and inserted into the wild-type cDNA-containing expression vector by replacing the sequences between the NcoI site at bp 11 and the MscI site at bp 943. The entire replacement fragment and the cloning sites were sequenced to verify that no additional changes were introduced by PCR.

Expression Analysis of Wild-Type and Mutagenized cDNA

Overnight cultures of JM$_{105}$™ containing vector alone, vector+wild-type MTHFR cDNA, or vector+mutagenized cDNA were grown at 370 C. in 2×YT media with 0.05 mg/ml ampicillin. Fresh 10 ml. cultures of each were inoculated with approximately 50 $\mu$L of overnight cultures for a starting O.D. of 0.05, and were grown at 37° C. to an O.D. of 1 at 420 nM. Cultures were then induced for 2 hrs. with 1 mM IPTG and pelleted. The cells were resuspended in TE buffer with 2 $\mu$g/ml aprotinin and 2$\mu$g/ml leupeptin (3.5×wet weight of cells). Cell suspensions were sonicated on ice for 3×15 sec. to break open cell membranes and then centrifuged for 30 min. at 4° C. to pellet cell debris and unlysed cells. The supernatant was removed and assayed for protein concentration with the Bio-Rad™ protein assay. Western analysis was performed using the Amersham ECL™ kit according to the instructions of the supplier, using antiserum generated against purified porcine liver MTHFR. Enzymatic assays were performed by established procedures; pre-treating the extracts at 46° C. for 5 min. before determining activity assessed thermolability. Specific activities (nmol formaldehyde/hr./mg. protein) were calculated for the 2 cDNA-containing constructs after subtraction of the values obtained with vector alone (to subtract background *E. Coli* MTHFR activity).

The MTHFR cDNA (2.2 kb) (FIG. 6) has an open reading frame of 1980 bp, predicting a protein of 74.6 kDa. The purified porcine liver enzyme has been shown to have subunits of 77 kDa. Western analysis (FIG. 7A) of several human tissues and of porcine liver has revealed a polypeptide of 77 kDa in all the studied tissues, as well as an additional polypeptide of approximately 70 kDa in human fetal liver and in porcine liver, suggesting the presence of isozymes. Two $\mu$g of bacterial extract protein was used for lanes 1–3. The tissues (lanes 4–8) were prepared by homogenization in 0.25M sucrose with protease inhibitors (2 μg/ml each of aprotinin and leupeptin), followed by sonication (3×15 sec.) on ice. The extracts were spun for 15 min. in a microcentrifuge at 14,000 g and 100 μg of supernatant protein was used for Western analysis. h=human; p=porcine.

The wild-type cDNA and a mutagenized cDNA, containing the A→V substitution, were expressed in E. Coli to yield a protein of approximately 70 kDa (FIG. 7A), which co-migrates with the smaller polypeptide mentioned above. Treatment of extracts at 46° C. for 5 minutes revealed that the enzyme containing the substitution was significantly more thermolabile than the wild-type enzyme (p<0.001; FIG. 7B). Two separate experiments (with 3–4 replicates for each construct for each experiment) were performed to measure thermostable activity of the wild-type MTHFR and mutagenized MTHFR A→V cDNAs. The values shown represent mean ±standard error for each experiment, as % of residual activity after heating. The means of the specific activities before heating (expressed as nmol formaldehyde/hr./mg. protein) were as follows: Exp. 1, 3.8 and 5.3 for MTHFR and MTHFR A→V, respectively; Exp. 2, 6.2 and 7.5 for MTHFR and MTHFR A→V, respectively. The expression experiments were not designed to measure differences in specific activity before heating, since variation in efficiencies of expression could contribute to difficulties in interpretation. Curiously though, the specific activity for the mutant construct was higher in both experiments. It is possible that the mutant protein has increased stability in E. Coli, or that inclusion bodies in the extracts contributed to differences in recovery of properly-assembled enzyme.

These studies have identified a common substitution in the MTHFR gene which results in thermolability in vitro and in vivo. The mutation, in the heterozygous or homozygous state, correlates with reduced enzyme activity and increased thermolability of MTHFR in lymphocyte extracts. A significant elevation in plasma homocysteine was observed in individuals who were homozygous for the mutation. Statistically-significant differences for homocysteine levels were not observed between heterozygotes and (−/−) individuals; this observation is not surprising, since plasma homocysteine can be influenced by several environmental factors, including intake of folate, vitamin $B_{12}$, vitamin $B_6$, and methionine, as well as by genetic variation at other loci, such as the cystathionine-β-synthase gene.

The alanine to valine substitution conserves the hydrophobicity of the residue and is associated with small changes in activity, in contrast to non-conservative changes, such as the previously-reported arginine to glutamine change in MTHFR, which is associated with a greater decrease in enzyme activity and severe hyperhomocysteinemia. The alanine residue is situated in a region of homology with the bacterial metF genes. The same region of homology was also observed in the human dihydrofolate reductase (DHFR) gene (FIG. 11), although the alanine residue itself is not conserved; this region of amino acids 130–149 of DHFR contains T136 which has been implicated in folate binding in an analysis of the crystal structure of recombinant human DHFR. It is tempting to speculate that this region in MTHFR is also involved in folate binding and that the enzyme may be stabilized in the presence of folate. This hypothesis is compatible with the well-documented influence of folate on homocysteine levels and with the reported correction of mild hyperhomocysteinemia by folic acid in individuals with premature vascular disease, and in individuals with thermolabile MTHFR.

Although the cDNA is not long enough to encode the larger MTHFR polypeptide, it is capable of directing synthesis of the smaller isozyme. The ATG start codon for this polypeptide is within a good consensus sequence for translation initiation. Whether the isozyme is restricted to liver and what its role is in this tissue remain to be determined.

These data have identified a common genetic change in MTHFR which results in thermolability; these experiments do not directly address the relationship between this change and vascular disease. Nonetheless, this polymorphism represents a diagnostic test for evaluation of MTHFR thermolability in hyperhomocysteinemia. Large case-control studies are required to evaluate the frequency of this genetic change in various forms of occlusive arterial disease and to examine the interaction between this genetic marker and dietary factors. Well-defined populations need to be examined, since the limited data set thus far suggests that population-specific allele frequencies may exist. More importantly, however, the identification of a candidate genetic risk factor for vascular disease, which may be influenced by nutrient intake, represents a critical step in the design of appropriate therapies for the homocysteinemic form of arteriosclerosis.

cDNA for MTHFR and its Potential Utility

The cDNA sequence is a necessary starting point for the detection of MTHFR sequence abnormalities that would identify individuals at risk for cardiovascular and neurological diseases, as well as other disorders affected by folic acid metabolism. Diagnostic tests by DNA analysis are more efficient and accurate than testing by enzymatic/biochemical assays. Less blood is required and results are available in a shorter period of time. The tests could be performed as a routine operation in any laboratory that performs molecular genetic diagnosis, without the specialized reagents/expertise that is required for an enzyme-based test.

The second major utility of the cDNA would be in the design of therapeutic protocols, for correction of MTHFR deficiency. These protocols could directly involve the gene, as in gene therapy trials or in the use of reagents that could modify gene expression. Alternatively, the therapy might require knowledge of the amino acid sequence (derived from the cDNA sequence), as in the use of reagents that would modify enzyme activity. The identification of sequences and/or sequence changes in specific regions of the cDNA or protein, such as FAD binding sites or folate-binding sites, are useful in designing therapeutic protocols involving the above nutrients.

Utility of Invention in Clinical and Diagnostic Studies

Coronary artery disease patients in Montreal (n=153) were studied to examine the frequency of the alanine to valine substitution. Fourteen percent of the patients were homozygous for this mutation. An analysis of 70 control individuals (free of cardiovascular disease) demonstrated that only seven % of these individuals were homozygous for the alanine to valine mutation.

Analysis of homocysteine levels in 123 men of the above patient group indicated that the mutant allele significantly raised homocysteine levels from 10.2 micromoles/L in homozygous normal men to 11.5 and 12.7 in heterozygotes and homozygous mutants, respectively.

Families with a child with spina bifida, a neural tube defect, have been examined for the presence of the alanine to valine mutation. Approximately 16% of mothers who had a child with spina bifida were homozygous for this mutation, while only 5% of control individuals were homozygous. Fathers of children with spina bifida also had an increased prevalence of the homozygous mutant genotype (10%) as did the affected children themselves (13%).

Table 4 indicates the interactive effect of folic acid with the homozygous mutant alanine to valine change. In a study of families from Framingham, Mass. and Utah, individuals who were homozygous mutant but had folate levels above 5 ng/ml did not have increased homocysteine levels compared to individuals with the normal or heterozygous genotype. However, individuals who were homozygous mutant but had folate levels below 5 ng/ml had homocysteine levels that were significantly higher than the other genotypes.

TABLE 4

Mean fasting and PML homocysteine levels for different MTHFR genotypes

| Plasma Homocysteine | MTHFR genotype | | | |
|---|---|---|---|---|
| | Normals (−/−) | Heterozygotes (+/−) | Homozygotes (+/+) | $P_{trend}$ |
| N | 58 | 61 | 30 | |
| Fasting* | 9.4 | 9.2 | 12.1 | 0.02 |
| Folate < 5 ng/mL | 10.2 | 10.4 | 15.2 | 0.002 |
| Folate³ 5 ng/mL | 8.2 | 7.5 | 7.5 | 0.52 |
| Post-Methionine load | 30.0 | 30.9 | 31.3 | 0.62 |

*Significant interaction between folate levels and genotype (p = 0.03)

Table 4 provides preliminary data for therapeutic intervention by folic acid supplementation to individuals who are homozygous for the alanine to valine change. The data suggest that higher levels of plasma folate would lead to normalization of homocysteine levels in mutant individuals and might prevent the occurrence of disorders associated with high homocysteine levels, such as cardiovascular disease, neural tube defects, and possibly other disorders. Folic acid supplementation for mutant individuals might also restore methionine and S-adenosylmethionine levels to normal. This would be relevant for disorders that are influenced by methylation, such as neoplasias, developmental anomalies, neurologic disease, etc.

Genetic Polymorphism in Methylenetetrahydrofolate Reductase (MTHFR) Associated with Decreased Activity A common mutation (C677T) results in a thermolabile enzyme with reduced specific activity (approximately 35% of control values in homozygous mutant individuals). Homozygous mutant individuals (approximately 10% of North Americans) are predisposed to mild hyperhomocysteinemia, when their folate status is low. This genetic-nutrient interactive effect is believed to increase the risk for neural tube defects (NTD) and vascular disease. There has been reported an increased risk for spina bifida in children with the homozygous mutant genotype for C677T. With the present invention, a second common variant in MTHFR (A1298C), an E to A substitution has been characterized. Homozygosity was observed in approximately 10% of Canadian individuals. This polymorphism was associated with decreased enzyme activity; homozygotes had approximately 60% of control activity in lymphocytes.

A sequence change (C1298A) has been identified. Heterozygotes for both the C677T and the A1298C mutation, approximately 15% of individuals, had 50%–60% of control activity, a value that was lower than that seen in single heterozygotes for the C677T variant. No individuals were homozygous for both mutations. A silent genetic variant T1317C, was identified in the same exon. It was relatively infrequent (allele frequency=5%) in the study group, but was common in a small sample of African individuals (allele frequency=39%).

In addition, by virtue of the role of MTHFR in folate-dependent homocysteine metabolism, the C677T mutation predisposes to mild hyperhomocysteinemia, a risk factor for vascular disease, in the presence of low folate status. By the present invention, the frequency of the A1298C variant has been determined and its potential impact on enzyme function has been assessed.

Patients with spina bifida and mothers of patients were recruited from the Spina Bifida Clinic at the Montreal Children's Hospital following approval from the Institutional Review Board. Control children and mothers of controls were recruited from the same institution. Blood samples were used to prepare DNA from peripheral leukocytes, to assay MTHFR activity in lymphocyte extracts, and to measure total plasma homocysteine (tilcy). The presence of the C677T mutation (A to V) was evaluated by PCR and HinfI digestion (2). The A1298C mutation was initially examined by PCR and MboII digestion (5). The silent mutation, T1317C, was identified by SSCP and sequence analysis in a patient with severe MTHFR deficiency and homocystinuria. This patient, an African-American female, already carries a previously-described splice mutation (patient 354 (8)). Since this mutation also creates a MboII site and results in a digestion pattern identical to that of the A1298C mutation, distinct artificially-created restriction sites were used to distinguish between these 2 mutations. Detection of the A1298C polymorphism was performed with the use of the sense primer 5'-GGGAGGAGCTGACCAGTGCAG-3' (SEQ ID NO:15) and the antisense primer (5'-GGGGTCAGGCCAGGGGCAG-3', SEQ ID NO:16), such that the 13 8 bp PCR fragment was digested into 119 bp and 19 bp fragments by Fnu4HI in the presence of the C allele. An antisense primer (5'-GGTTCTCCCGAGAGGTAAAGATC-3', SEQ ID NO:17), which introduces a TaqI site, was similarly designed to identify the C allele of the T3117C polymorphism. Together with a sense primer (5'-CTGGGGATGTGGTGGCACTGC-3', SEQ ID NO:18), the 227 bp fragment is digested into 202 bp and 25 bp fragments.

TABLE 5

Genotype distributions, MTHFR activity (nmol formaldehyde/mg protein/hour), and total plasma homocysteine (tHcy; μM) for mothers and children

| | | E/E | | | E/A | | | A/A | | |
|---|---|---|---|---|---|---|---|---|---|---|
| | | A/A | A/V | V/V | A/A | A/V | V/V | A/A | A/V | V/V |
| Mothers (n = 141) | | | | | | | | | | |
| # | | 24 | 32 | 19 | 27 | 26 | 0 | 13 | 0 | 0 |
| % | | 17 | 23 | 13 | 19 | 18 | 0 | 9 | 0 | 0 |

TABLE 5-continued

Genotype distributions, MTHFR activity (nmol formaldehyde/mg protein/hour), and total plasma homocysteine (tHcy; μM) for mothers and children

|  | E/E | | | E/A | | | A/A | | |
|---|---|---|---|---|---|---|---|---|---|
|  | A/A | A/V | V/V | A/A | A/V | V/V | A/A | A/V | V/V |
| MTHFR | 49.0 ± 18.9 [14] | 33.0 ± 10.8 [19]* | 15.7 ± 4.5 [11]* | 45.0 ± 16.0 [15] | 30.2 ± 19.3 [15]* | — | 32.1 ± 9.0 [7]* | — | — |
| THcy | 9.5 ± 3.1 [24] | 10.0 ± 3.2 [32] | 12.2 ± 7.1 [19]** | 8.4 ± 2.1 [25] | 10.0 ± 3.1 [26] | — | 9.5 ± 2.0 [13] | — | — |
| Children (n = 133) | | | | | | | | | |
| # | 23 | 43 | 18 | 20 | 15 | 1 | 13 | 0 | 0 |
| % | 17 | 32 | 13 | 15 | 11 | 1 | 10 | 0 | 0 |
| MTHFR | 52.0 ± 17.0 [12] | 38.2 ± 15.0 [27]* | 16.2 ± 5.3 [11]* | 35.7 ± 9.7 [18]* | 26.1 ± 5.0 [9]* | 21.6 [1] | 29.5 ± 10.3 [6]* | — | — |
| THcy | 7.6 ± 2.5 [23] | 8.2 ± 3.0 [43] | 9.7 ± 5.1 [18]** | 7.5 ± 2.3 [20] | 8.1 ± 2.8 [15] | 9.5 [1] | 7.4 ± 1.5 [13] | — | — |

The three A1298C genotypes and the three C677T genotypes are designated by the amino acid codes: EE, EA, AA, and AA, AV, VV, respectively. Statistical significance was assessed by student t-test, in comparison with EEAA values.
*(p < 0.05);
**(p < 0.07).
Standard deviations are given and square brackets indicate the number of individuals for whom MTHFR activities and homocysteine levels were available.

The frequencies of the three genotypes for the A1298C mutation (EE, EA and AA) were not different between case and control mothers, or between case and control children (data not shown). Consequently, all the mothers and all the children were grouped together for analyses (Table 5). Nine % of mothers had the homozygous AA genotype while 37% were heterozygous. This frequency is quite similar to the frequency of the homozygous mutant genotype (VV) for the C677T polymorphism. In the MTHFR human cDNA sequence mentioned above, the cDNA contained the C nucleotide at bp 1298 change as a C1298A substitution. Since the A nucleotide is clearly the more frequent base at this position, the A1298C nomenclature was chosen.

Since the C677T mutation (A to V) decreases MTHFR activity and increases homocysteine levels, the three genotype groups for the A1298C (E to A) mutation were further stratified by the genotype for the A to V mutation, to avoid the confounding influence of the latter polymorphism on MTHFR activity and homocysteine levels. The frequencies of the 9 genotypes, with MTHFR activity and homocysteine levels for each genotype, are shown in Table 5. If the mothers and children without either mutation i.e. EE/AA are used as the reference (control) group, the mothers and children that are homozygous for the A1298C mutation (AAAA) have approximately 65% and 57%, respectively, of control MTHFR activity. Heterozygotes for the C677T change alone (EEAV) have approximately 70% of control activity, as reported in other studies, while double heterozygotes (EAAV), 18% of mothers and 11% of children, have an additional loss of activity (approximately 62% and 50% of control values, respectively).

Homocysteine levels were not significantly increased by the A1298C mutation, but homocysteine was elevated (with borderline significance, p<0.07) in mothers and children who were homozygous for the C677T change. The small number of individuals who were homozygous for the A1298C mutation (n=13) may have influenced the power of the statistical analyses and precluded an investigation of the genetic-nutrient interactive effect that leads to mild hyperhomocysteinemia, as seen in individuals with the C677T mutation.

The T1317C substitution does not alter the amino acid (phenylalanine) and is likely a benign change, although a splicing defect cannot be ruled out at the present time. In an evaluation of 38 control mothers from this study, 2 were found to be heterozygous and one was identified as a homozygote, resulting in an allele frequency of 5% (4/76). Since this substitution was identified in an African-American female, control African individuals were also examined (n=9). Seven of these were heterozygous, resulting in an allele frequency of 39% (7/18).

The A1298C mutation clearly reduces MTHFR activity, albeit to a lesser extent than the C677T mutation. Consequently its effect on homocysteine levels is also attenuated and, in fact, may only be significant when an individual carries both mutations and/or has poor nutrient status. However, since double heterozygotes are estimated to represent approximately 15% of the population, this variant should be examined in conjunction with the C677T variant in studies of hyperhomocysteinemia.

The A1298C mutation is clearly polymorphic in Canadian individuals and should be examined in other populations. The A nucleotide is likely to be the ancestral sequence since it represents the more common allele, although the original human MTHFR cDNA sequence (GenBank accession number U09806) carried the C nucleotide. This polymorphism is similar in frequency to the C677T polymorphism. Presumably the two substitutions arose separately on a A1298/C677 or E/A haplotype, since the haplotype with both substitutions (C1298/T677 or A/V) is extremely rare. One such haplotype was seen in a child with the EAVV genotype, suggesting a recombinant chromosome.

Doubly homozygous individuals (AAVV) were not observed in this study. Since the double mutation in cis is rare, it is possible that not enough alleles were studied. Larger studies in other populations might result in the identification of these individuals. Presumably the MTHFR activity would be even lower and homocysteine levels might be higher than those observed thus far.

The C677T polymorphism in exon 4 is within the N-terminal catalytic domain of the enzyme whereas the A1298C polymorphism in exon 7 is within the C-terminal regulatory domain. The more dramatic effect on enzyme activity with the first polymorphism may be a consequence of its location within the catalytic region. The second polymorphism could affect enzyme regulation, possibly by S-adenosylmethionine, an allosteric inhibitor of MTHFR, which is known to bind in the C-terminal region.

Many studies have examined the effects of the C677T polymorphism on MTHFR enzyme activity and on homocysteine levels. Although the correlation between the presence of this substitution and decreased enzyme activity/increased homocysteine levels has been quite good, the variability in results, particularly in heterozygous individuals, may reflect the presence of a second common variant in the population.

The third variant, T1317C, was present on 5% of alleles in Canadian individuals but appears to be extremely common in individuals of African ancestry. The methodology outlined in this report should be used to assess the frequency of the A1298C and T1317C in other populations, since the use of the MboII restriction site for analysis of the A1298C change, as first reported, would not discriminate between the 2 polymorphisms.

The C677T mutation is a risk factor for hyperhomocysteinemia and has been implicated in both neural tube defects and vascular disease.

Gene structure of Human and Mouse Methylenetetrahydrofolate Reductase (MTHFR)

A human cDNA for MTHFR, 2.2 kb in length, has been expressed and shown to result in a catalytically-active enzyme of approximately 70 kDa. Fifteen mutations have been identified in the MTHFR gene: 14 rare mutations associated with severe enzymatic deficiency and one common variant associated with a milder deficiency. The common polymorphism has been implicated in three multifactorial diseases: occlusive vascular disease, neural tube defects and colon cancer. The human gene has been mapped to chromosomal region 1p36.3 while the mouse gene has been localized to distal Chromosome 4. The isolation and characterization of the human and mouse genes for MTHFR is herein reported. A human genomic clone (17 kb) was found to contain the entire cDNA sequence of 2.2 kb; there were 11 exons ranging in size from 102 bp to 432 bp. Intron sizes ranged from 250 bp to 1.5 kb with one exception of 4.2 kb. The mouse genomic clones (19 kb) start 7 kb 5' to exon 1 and extend to the end of the coding sequence. The mouse amino acid sequence is approximately 90% identical to the corresponding human sequence. The exon sizes, locations of intronic boundaries, and intron sizes are also quite similar between the two species. The availability of human genomic clones has been useful in designing primers for exon amplification and mutation detection. The mouse genomic clones may be used to make constructs for gene targeting and generation of mouse models for MTHFR deficiency.

A common polymorphism, C677T has been identified, which converts an alanine codon to valine (Frosst et al., 1995). This common polymorphism, which is present on approximately 35% of alleles in the North American population, encodes the thermolabile variant and predisposes to mild hyperhomocysteinemia when folate status is low (Frosst et al., 1995; Jacques et al., 1996; Christensen et al., 1997). This genetic-nutrient interactive effect is believed to be a risk factor for arteriosclerosis (Frosst et al, 1995) and neural tube defects. In contrast, the mutant homozygous genotype may decrease the risk for colon cancer.

The characterization of the genomic structure for human MTHFR is reported herein. The corresponding analysis of the mouse gene, with a comparison of the overall organization of the gene and the amino acid sequences in these two species, is also shown.

Screening of Genomic Libraries

Genomic libraries were screened using standard methods of plaque hybridization. The 2.2 kb human cDNA was radiolabelled and used as a probe in screening both human and murine genomic libraries. Screening for the human gene was performed on a phage library of partial EcoRI digestion fragments from total genomic DNA (ATCC # 37385), and on a phage library of chromosome 1-specific complete EcoRI digestion fragments (ATCC# 57738). Screening for the mouse gene was performed on a XDASH library of partial Sau3A digestion fragments from total genomic DNA of mouse strain 129SV (obtained from Dr. J. Rossant, University of Toronto). Positive clones were purified by sequential rounds of screening and isolation, and phage DNA was isolated using phage DNA isolation columns (QIAGEN). Human clones were digested with EcoRI to release the inserts, and then with XbaI to facilitate cloning into Bluescript plasmid (Stratagene). The mouse clones were digested with SalI or EcoRI, and the inserts were subcloned into Bluescript.

Characterization of Mouse cDNA Sequences

Mouse genomic clones were sequenced (Sequenase kit, Amersham) using human cDNA primers spanning most of the available 2.2 kb cDNA. These sequences were then used to generate mouse-specific cDNA primers. The mouse-specific primers were used in PCR amplification of overlapping cDNA fragments from reverse-transcribed mouse liver RNA. The PCR products were subcloned into the PCRII vector (Invitrogen) and sequenced. Two different species of mouse (C57Bl/6J and ct) were used to generate MTHFR sequence by RT-PCR, to ensure that the PCR protocol did not generate sequencing errors.

Characterization of Intron Boundaries and Sizes, and Restriction Analysis of Human and Mouse Genes Primers from cDNA sequences of human and mouse were used to sequence the respective genomic clones. Intron boundaries were determined from regions of divergence between cDNA and genomic clone sequences, and by the identification of splice acceptor and donor consensus sites. Intronic sequences were obtained for 40–50 bp from the junctions and are shown in FIGS. 12A–12B (human) and FIGS. 13A–13B (mouse). The same cDNA primers were used in PCR amplification of total genomic DNA and of genomic clones to determine the approximate sizes of introns in the human and mouse genes. Table 6 lists the locations and approximate sizes of introns for both species. The PCR products were analyzed by restriction enzyme digestion to generate a preliminary restriction map of the gene. This restriction map was then confirmed by restriction analysis of the genomic clones in Bluescript.

Referring to FIGS. 12A–12B, the bp location of the exons within the cDNA, in parentheses, is based on the published human cDNA sequence (GenBank accession number U09806). Bp 1 is 12 bp upstream from the ATG in the original cDNA; an asterisk indicates the equivalent base here. Exon 1 contains the ATG start site (underlined), and exon 11 contains the termination codon (underlined). Uppercase characters indicate exonic sequences, and lower case characters are intronic. Consensus splice junction sequences are underlined. The 3' boundary of exon 11 has been designated by the location of the polyA tail.

Referring to FIGS. 13A–13B, the bp location of the exons within the cDNA, in parentheses, is based on the equivalent bp 1 of the human sequences in FIGS. 12A–12B (bp 1 is indicated by an asterisk). Exon 1 contains the ATG start site (underlined), and exon 11 contains the termination codon (doubly underlined). Uppercase characters indicate exonic sequences, and lower case characters are intronic. Consensus splice junction sequences are underlined. The 3' boundary of exon 11 is designated as the termination codon, since the site of polyadenylation is unknown. Also underlined in exon 11 is the first repeat of the 52 bp repeated element.

Figure 14:
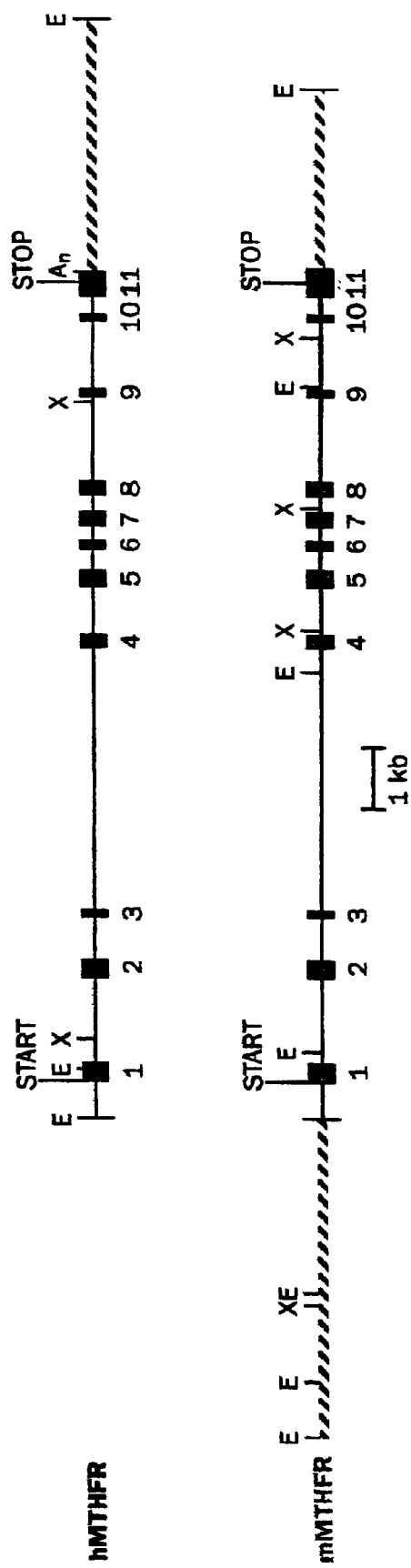
FIG. 14 illustrates intron sizes and locations for both human and mouse genes.

Referring to FIG. 14, exon sizes for human and mouse are reported in FIGS. 12A–12B and FIGS. 13A–13B, respectively. Exons are indicated in shaded boxes. Uncharacterized regions of the gene are hatched, and exon numbering corresponds to FIGS. 12A–12B and 13A–13B. E=EcoRI; X=XbaI; $A_n$=polyadenylation site. The EcoRI restriction site at the 5' end of the mouse gene is part of the phage polylinker sequence.

Referring to FIG. 15, residues that are identical to the human MTHFR sequence are shown as empty boxes, and gaps in amino acid homology are represented by a dash.

Human Genomic Clones

The genomic clones isolated from the human libraries contained a 16 kb EcoRI fragment, encompassing part of exon 1 and exons 2 through 11, and a 1 kb EcoRI fragment containing most of exon 1. Exon 1 is defined as the most 5' exon from the previously published cDNA sequence; it contains the ATG start site that was used to express the human cDNA in bacterial extracts (Frosst et al. 1995). A graphic representation of the human gene and its restriction map are depicted in FIG. 3. The sequences of each exon and 50 bp of flanking intronic sequences are shown in FIGS. 12A–12B. Exons range in size from 102 bp to 432 bp, and the critical dinucleotides in the 5' and 3' splice site consensus sequences (GT and AG, respectively) are underlined. The 3' boundary of exon 11 is defined by the site of polyadenylation in the cDNA; a possible polyadenylation signal (AACCTA) is present 15 bp upstream of the polyadenylation site, although it varies from the consensus sequence. Table 6 lists the locations and approximate sizes of introns as determined by PCR amplification; the introns range in size from approximately 250 bp to 4.2 kb.

Mouse Genomic Clones

Genomic clones isolated from the mouse libraries were digested with EcoRI for subcloning and characterization. Exon nomenclature is based on the corresponding human gene sequences. FIGS. 13A–13B list all known exons and their sizes, with 40 to 50 bp of flanking intronic sequences. FIG. 14 shows a graphic representation of the mouse genomic structure aligned with the human gene. The size of exon 11 is undetermined, since the sequence for this region was determined directly from the genomic clones. The termination codon is located within a region of 52 bp which is repeated 3 times in the gene. The significance of this, if any, is unknown at the present time. The dinucleotides of the splice junctions (underlined in FIGS. 13A–13B) are in agreement with consensus sequences. Table 6 lists the approximate sizes of introns as determined by PCR, and their bp location in the CDNA. The introns range in size from approximately 250 bp to 4.2 kb.

Comparison of the Human and Mouse Genes

The human and mouse genes are very similar in size and structure (FIG. 14). The introns are similar in size, and identical in location within the coding sequence. However, the mouse cDNA is one amino acid shorter in exon 1 which causes a shift in bp numbering of the mouse cDNA (Table 6, FIGS. 13A–13B). Exon 1 was defined from the original published human cDNA, based on the presence of a translation start codon. In both human and mouse genes, the 5' boundary of exon 1 was assigned after the isolation of several non-coding cDNA extensions that are generated by alternative splicing from this junction. Characterization of these 5' cDNA extensions is in progress. The nucleotide sequences of the human and mouse genes are very similar within coding regions, but homology decreases dramatically in the 3' UTR region and within introns.

Human and Mouse Primary Amino Acid Sequence Homology

The primary amino acid sequences of human and mouse were compared to each other, and aligned with the sequence of the MetF (MTHFR) enzyme from bacteria (FIG. 15). The human and mouse amino acid sequences are almost 90% identical. As previously observed, only the 5' half of the mammalian sequences align with the bacterial enzyme; bacterial MTHFR has the same catalytic activity as the mammalian enzyme but lacks the regulatory region in the C-terminal domain. The murine amino acid sequence is two amino acids shorter than the human sequence: one less amino acid in exon 1 and one less in exon 11.

The isolation of the human MTHFR gene and the analysis of gene structure are part of an ongoing effort to study MTHFR deficiency in homocystinuria and in multifactorial diseases. The availability of genetic structure information and of intronic sequences will help in the mutational analysis of patients suffering from MTHFR deficiency and in the characterization of the 5' regulatory region.

Expression analysis of the 2.2kb cDNA in a bacterial expression system resulted in a catalytically-active 70 kDa protein (Frosst et al. 1995). A MTHFR polypeptide of this size was observed in some human tissues on Western blots, but a larger isozyme (77 kDa), corresponding to the estimated size of the porcine polypeptide, was observed in all the examined tissues. These data suggested the presence of protein isoforms for MTHFR that could be tissue-specific (Frosst et al., 1995). Since human or mouse sequences homologous to the N-terminal porcine amino acid sequences have not been identified, it is assumed that the missing sequences required to encode the larger isoform are 5' to the available cDNA sequences. Two mRNAs for human MTHFR (approximately 7.5 and 8.5 kb) have been seen in all tissues on Northern blots (data not shown), suggesting very large UTRs. The isolation of 5' coding sequences has been complicated by the presence of several alternatively-spliced 5' non-coding extensions that splice into exon 1. The alternative splicing into exon 1 has been observed in both human and mouse MTHFR. The long UTRs and the alternative splicing events suggest that the regulation of this important gene may be quite complex.

Nonetheless, the available information has been critical for identification of mutations in patients with various forms of MTHFR deficiency. The mouse sequences in exons 1 and 2 have been useful in the design of antisense oligonucleotides to successfully inhibit MTHFR in mouse embryo cultures and disrupt development of the neural tube (Lanoue et al. 1997). The isolation and characterization of mouse genomic clones is essential for construction of targeting vectors to generate mouse models for MTHFR deficiency.

TABLE 6

Approximate sizes of introns, and their locations in human and mouse MTHFR cDNA

| Intron | Approximate size (kb) | Human location[1] | Mouse location[1] |
| --- | --- | --- | --- |
| 1 | 1.5 | 248–249 | 245–246 |
| 2 | 0.8 | 487–488 | 484–485 |
| 3 | 4.2 | 598–599 | 595–596 |
| 4 | 0.8 | 792–793 | 789–790 |

TABLE 6-continued

Approximate sizes of introns, and their
locations in human and mouse MTHFR cDNA

| Intron | Approximate size (kb) | Human location[1] | Mouse location[1] |
|---|---|---|---|
| 5 | 0.35 | 1043–1044 | 1040–1041 |
| 6 | 0.25 | 1178–1179 | 1175–1176 |
| 7 | 0.3 | 1359–1360 | 1356–1357 |
| 8 | 1.5 | 1542–1543 | 1539–1540 |
| 9 | 1.3 | 1644–1645 | 1641–1642 |
| 10 | 0.3 | 1764–1765 | 1761–1762 |

[1]Base pairs flanking introns, from FIGS. 1 and 2. Bp1 is 12 bp upstream from the ATG, as in the original report of the cDNA sequence (Goyette et al. 1994).

Various doses of methotrexate (a drug used in treatment of cancer and arthritis, possibly other diseases) were added to colon carcinoma lines in culture. Much lower doses of methotrexate are needed to kill the lines that carry the 677C/T mutation in MTHFR, compared to lines that do not carry this mutation. The IC50 (concentration needed to kill half the cells) is approximately 20 nM for lines with the mutation and approximately 150 nM for lines without the mutation. To extrapolate to the human condition, patients with this MTHFR mutation might require lower doses of methotrexate for therapy, or might be subject to methotrexate toxicity at high doses.

TABLE 7

Summary of BMD analysis
Entire cohort: Values are means +/− SE

| | Genotype 1/1 | Genotype 1/2 | Genotype 2/2 |
|---|---|---|---|
| Spinal Z score | −1.06 (0.193) | −1.25 (0.176) | −1.86 (0.238) |
| Femoral neck Z score | −0.69 (0.134) | −0.78 (0.126) | −0.87 (0.228) |
| Trochanter Z score | −0.60 (0.142) | −0.52 (0.134) | −1.15 (0.249) |
| Ward's triangle Z score | −0.67 (0.147) | −0.80 (0.139) | −0.96 (0.257) |

Table 7 indicates the values for bone mineral density in a group of individuals who were examined for the MTHFR C677T mutation.
Genotype 1/1 = normal C/C
Genotype 1/2 = carriers C/T
Genotype 2/2 = homozygons mutant T/T As seen on Table 7, the lower the score, the lower the bone mineral density and therefore the higher the risk for osteoporosis. The results suggest that the homozygons mutant genotype (2/2) is asssociated with lower bone mineral density and therefore higher risk of osteoporosis.

Diagnosis and Therapeutic Outcome of a Psychosis

MTHFR alleles are also useful as diagnostic, therapeutic, prognostic, and pharmacogenomic markers for neurological disorders such as psychoses and in other diseases and disorders that may be treated with anti-psychotic therapeutics.

Psychoses are serious, debilitating mental illnesses which are characterized by loss of contact with reality and may also include any of the following symptoms: delusions, hallucinations, thought disorder, strange behavior or emotions, or withdrawal from social contact. The duration of untreated psychosis may be correlated with worsened patient-prognosis.

Schizophrenia is the most common psychosis, which affects approximately 2 million Americans. Although genetic factors are known to play a role in the etiology of schizophrenia, identification of susceptibility genes has been difficult. This difficulty may be due partially to the variability of the schizophrenia phenotype, including variations in severity of symptoms, response to medications, and long-term outcome. Indeed, one third to one quarter of schizophrenic subjects remain severely symptomatic despite multiple trials with individual or combinations of anti-psychotic therapeutics, also called neuroleptics. This variability may reflect factors such as genetic heterogeneity or the presence of modifier genes. Compared to neuroleptic nonresponders, the group of responders is characterized by a high female to male ratio, better long-term outcome, and more frequently disturbed indices of dopamine neurotransmission.

In addition to the inability to reduce symptoms in a substantial number of schizophrenia patients, current neuroleptic therapeutics also cause a variety of serious side effects. Examples of the adverse effects of conventional neuroleptics include cardiac conduction abnormalities can result in patient deaths, seizures, involuntary repetitive movements (tardive dyskinesia), dulling of cognition, sedation, weight gain, sexual or reproductive dysfunction, blood dyscrasias, jaundice, skin reactions such as uticaria and dermatitis, and extrapyramdial effects. Extrapyramdial side effects involve conditions such as abnormal facial expressions, restlessness or constant movement, and rigidity and tremor at rest (parkinsonian syndrome). Because of the severity of these side effects and the low therapeutic-to-toxic index of conventional neuroleptics, other neuroleptics, called atypical neuroleptics, have been recently developed. Atypical neuroleptics have a lower incidence of extrapyramidal symptoms and tardive dyskinesia; however, they are still associated with weight gain and effects on blood pressure and liver function, as observed for conventional neuroleptics.

Due to the severity and heterogeneity of schizophrenia, improved methods are needed for diagnosing people at risk for or suffering from schizophrenia. Improved methods are also desirable for determining a preferred therapy for a particular diagnosed individual or group of individuals. The selection of a preferred therapy for a particular subject may prevent the subject from having to endure possibly irreversible side effects from therapies that are ineffective for that subject. Reduced side effects of the preferred therapy compared to other therapies may result in greater patient compliance, further increasing the likelihood of therapeutic benefit from the therapy.

We have discovered that the heterozygous form of the C677T mutation in methylenetetrahydrofolate reductase (MTHFR) is more common in patients diagnosed with schizophrenia than in a healthy control population and thus is a risk factor for this disease. In addition, both the heterozygous and homozygous forms of this mutation are associated with an improved response to neuroleptic treatment and long-term outcome.

Because the C677T mutation results in decreased MTHFR activity and increased enzyme thermolability, other MTHFR genotypes or haplotypes having similar characteristics may be associated with schizophrenia or improved response to neuroleptics. For example, another mutation of human MTHFR, A1298C which converts glutamic acid to alanine, also results in reduced activity in the encoded protein, and individuals who are heterozygous for both the C677T and A1298C mutations have even lower MTHFR activity and have higher homocysteine levels than observed in individuals with the single C677T mutation. Other similar mutations include, but are not limited to, G167A, G482A, C559T, C692T, C764T, a G/A G792+1A, C985T, C1015T, C1081T, T1317C, and any combination of these MTHFR mutations.

In this study, two groups of schizophrenic patients selected on the basis of a priori defined criteria of long-term outcome and response to neuroleptics (excellent responders and very poor responders, Table 8) and a control group of health volunteers were compared with regard to the C-to-T substitution at nucleotide 677 of the MTHFR gene, called "V allele."

TABLE 8

Demographic and clinical characteristics of patients and controls

|  | Nonresponders (n = 62) | Responders (n = 43) |
| --- | --- | --- |
| Age (yr.) ± SD | 38.7 ± 6.9 | 40.6 ± 10.5 |
| Gender (% Males) | 74 | 67 |
| Age at 1 C (yr.) | 18.1 ± 3.9 | 24.2 ± 4.8** |
| Subtype, U/P/D/C | 26/30/4/1 | 6/36/1/0** |
| Time as in-patient (%) | 63.5 ± 38 | 8.2 ± 11.8** |
| BPRS score | 48.9 ± 9.0 | 24.4 ± 3.9** |

Age at 1 C = age at first contact with a psychiatric care facility,
U = undifferentiated,
P = paranoid,
D = disorganized,
C = catatonic,
BPRS = Brief psychiatric rating scale.

The heterozygous and homozygous C677T mutations were found more frequently in schizophrenia patients than in control subjects (Table 9). In addition, there was a significant association between schizophrenia and the presence of at least one C677T allele of the MTHFR gene ($\chi^2$=5.44, degrees of freedom (df)=1, p=0.019). This association was due to an over-representation of allele V in neuroleptic responder patients compared to controls ($\chi^2$=16.77, df=1, p=0.00004); non-responder patients did not differ from controls. In addition, the attributable fraction associated with carrying at least one V allele in the group of neuroleptic responder patients was patients and the C677T mutation was statistically stronger in males than in females.

The association between the C677T mutation and schizophrenia was observed for both a recessive (VV vs. AV+AA) as well as a dominant model (VV+AV vs. AA) of transmission of this mutation; however, the latter showed consistently more power to discriminate between responsive patients and controls (Table 9).

These results indicate that good response to neuroleptic medication and good long-term outcome characterize the schizophrenia phenotype associated with allele V of the MTHFR gene. The fact that no association with the V allele was observed in the groups of neuroleptic nonresponder patients indicates, as previously suggested, that these two groups of patients are at least partially different from a pathogenic point of view. The dosage effect of allele V on age-at-onset, a marker of severity of illness that is independent from responsiveness to neuroleptics, suggests that this association is possibly mediated by a schizophrenia subtype. Thus, the classification of schizophrenic patients by the presence or absence of the C677T mutation may be an effective strategy to reduce heterogeneity for studies of the treatment or biology of schizophrenia. Additionally, the association of allele V with the ability of neuroleptic treatment to reverse psychotic symptoms and possibly the deterioration associated with untreated psychosis may be due to the association of allele V with an ability to respond to neuroleptics that is independent of schizophrenia subtype.

While not meant to limit the invention to a particular theory, it also possible the V allele is associated with a disturbance in the one-carbon cycle metabolism regulated by MTHFR, since MTHFR provides the carbon group for the generation of S-adenosylmethionine, a universal methyl donor. A disturbance of one-carbon metabolism may result in a deficiency of methylation reactions that are required for numerous pathways including detoxification, DNA methylation and regulation of biogenic amine metabolism. Another possibility is that the V allelic variant may act as a

TABLE 9

Analysis of genotypic and allelic association of 677C → T polymorphism in MTHFR gene.

| | N of subjects with genotype (%) | | | $\chi^2$ statistic C vs. R | Number of alleles (%) | | |
| --- | --- | --- | --- | --- | --- | --- | --- |
| | A/A | V/A | V/V | (df = 1). | A | V | $\chi^2$ statistic (df = 1) |
| All subjects | | | | | | | C vs. R: $\chi^2$ = 17.52, |
| C | 41 (44.5) | 36 (40.0) | 13 (14.4) | D: $\chi^2$ = 16.12, | 117 (65.0) | 63 (35.0) | p = 0.00003 |
| R | 5 (11.6) | 23 (53.5) | 15 (34.9) | p = 0.00006 | 33 (38.4) | 53 (61.6) | C vs. NR: $\chi^2$ = 0.10, |
| NR | 25 (40.3) | 29 (46.8) | 8 (12.9) | R: $\chi^2$ = 7.49, p = 0.006 | 79 (63.7) | 45 (36.3) | p = 0.74 |
| Males | | | | | | | |
| C | 17 (41.4) | 18 (43.9) | 6 (14.7) | D: $\chi^2$ = 14.0, p = 0.0001 | 53 (63.4) | 30 (36.6) | $\chi^2$ = 12.77, |
| R | 1 (3.5) | 17 (58.6) | 11 (38.8) | R: $\chi^2$ = 5.01, p = 0.025 | 19 (32.7) | 39 (67.3) | p = 0.00035 |
| Females | | | | | | | |
| C | 24 (49.0) | 18 (36.7) | 7 (14.3) | D: $\chi^2$ = 2.02, p = 0.15 | 66 (67.3) | 32 (32.7) | $\chi^2$ = 2.82, p = 0.092 |
| R | 4 (28.6) | 6 (42.9) | 4 (28.5) | R: $\chi^2$ = 1.63, p = 0.20 | 14 (50.0) | 14 (50.0) | |

D = dominant model,
R = recessive model,
C = controls,
R = NLP responder patients,
NR = NLP non responder patients.
P-values are not corrected for multiples testing.

75%, meaning that 75% of the schizophrenia cases may be due to this mutation. The association between responder moderator of the severity of schizophrenia by increasing the plasma concentration of homocysteine. Indeed it has been reported that a homocysteine load causes worsening of psychotic symptoms in schizophrenic patients.

The association of other MTHFR alleles with schizophrenia, or any other disease, or with response to particular therapies may be determined by any standard methods (see, for example, those methods described in WO 00/04194; Ueda et al., Circulation 98:2148–2153, 1998, Tan et al., Lancet 350:995–999, 1997; Poirier et al., Proc. Natl. Acad. Sci. USA 92:12260–12264, 1995; Spire-Vayron de la Moureyre et al., British J. of Pharmacology 125:879–887, 1998; Drazen et al., Nature Genetics 22:168–170, 1999; Smeraldi et al., Molecular Psychiatry 3:508–511, 1998; Kuivenhoven et al. New Eng. J. of Med. 338(2):86–93, 1998; Aarranz et al., Molecular Psychiatry 3:61–66, 1998). Haplotyping may also be used to determine associations between particular mutations or combination of mutations and particular diseases or responses to particular therapies.

Clinical trials for an anti-psychotic therapy may be conducted as described below or using any other appropriate method. The subjects in the trial may be stratified based upon their MTHFR genotype at the relevant polymorphic sites. This stratification may be used to correlate an MTHFR genotype or haplotype with the efficacy or the safety of the therapy and may be performed before, during, or after the clinical trial. The correlation of the safety and efficacy of the therapy in subjects with a particular MTHFR mutation or combination of MTHFR mutations may be considered during the Food and Drug Administration (FDA) approval process and used to determine preferred therapies for the different MTHFR subgroups of subjects.

Briefly, clinical trials generally consist of four phases: Phase I is a safety study generally involving healthy volunteers; Phase II is a dose-ranging, efficacy study involving subjects diagnosed with a condition, and Phase III is a larger safety and efficacy study. If the efficacy data from the Phase III trial are statistically significant, the therapy may be approved by the FDA. Phase IV is a post-marking approval trial that may be used to further refine the approved indication population or to compare one therapy to another one. This process for testing a therapy in humans may also be modified by one skilled in the art depending on specific pharmacokinetic or pharmacodynamic properties of the therapy or the availability of subjects diagnosed with the condition. For example, cytotoxic therapies, such as cancer chemotherapeutics, are not tested in healthy control subjects and generally begin clinical trials with a Phase 11 study.

Clinical trials may be performed using standard protocols (see, for example, Spilker, *Guide to Clinical Trials*, Raven Press, 1991; Tygstrup, ed., *The Randomized Clinical Trial and Therapeutic Decisions* Marcel Dekker; Thall, ed. *Recent Advances in Clinical Trial Design and Analysis*, Cancer Treatment and Research, Ctar 75, Kluwer Academic, 1995; and Piantadosi, *Clinical Trials: A Methodologic Perspective*, Wiley Series in Probability and Statistics, 1997). Examples of possible clinical trials protocols include placebo-controlled, single blinded, double blinded, crossover, and other studies.

For the design of clinical trials to test the contribution of an MTHFR mutation or a combination of MTHFR mutations to variation in patient response to a therapy, one skilled in the art may use readily available methods to determine the appropriate parameters for a particular clinical trial. Examples of such factors include the genetic hypothesis to be tested, the number of subjects required to observe a statistically significant effect (power analysis), the appropriate dosing range, the duration of the trial, and the appropriate endpoints to measure the response to the therapy. The applications of genetic hypothesis testing, power analysis, and statistical analysis of patient response to each phase of a clinical trial have been described previously. Additionally, haplotyping may be used to detect which MTHFR genotype at which position may be correlated with a particular response to a particular therapy.

The endpoints of a clinical trial of an anti-psychotic therapy may include factors associated with the conditions. Examples of possible endpoints include semi-objective grading scales administered by clinical staff. Several standard grading scales have been developed and accepted as assessment tools of the efficacy of a therapy in clinical trials and include, but are not limited to, cognitive assessment, pain, psychotic, behavioral, and global clinical impression scales.

A further consideration for the design of a clinical trial for a compound in the category of psychiatric illness is the duration of the trial. It may take weeks to months before a "wash-out" can be achieved (i.e. reduction of the dose to the point of removal of therapy) for the therapies that the subjects had been receiving prior to the clinical trial. Additionally, many anti-psychotics exhibit dose-dependent efficacy and often require 2–3 weeks before empirical clinical global impression and semi-objective grading scale analysis suggests a therapeutic dose has been achieved. Both the "run-in" period for the achievement of a therapeutic dose and the "run-out" period for the subsequent decrease in the dose for removal of the therapy after the clinical trial must be performed under controlled conditions.

The present invention provides a number of advantages. For example, the methods described herein allow for the determination of a subject at risk for a psychosis for the timely administration of a prophylactic therapy to prevent or delay the psychosis. Thus, this determination of increased risk for a psychosis may occur before the presence of debilitating symptoms that might otherwise be required for a definitive diagnosis. The methods of the invention also have the advantage of only requiring the presence of one mutation in one MTHFR allele instead of requiring a homozygous mutation for the association of the mutation with a psychosis; this is a particular advantage in the diagnosis of schizophrenia which was previously correlated exclusively with homozygous patient genotypes. Additionally, the presence of mutations in MTHFR alleles may be easily and rapidly determined using standard techniques. Moreover, the administration of a preferred therapy to subject at risk for or diagnosed with from a psychosis may result in improved patient-outcome, improved drug-efficacy, or reduced drug-toxicity compared to the administration of other therapies. These results may reduce healthcare costs by decreasing the number of required doctor visits or hospitalizations.

The following example is provided to illustrate the invention. It is not meant to limit the invention in any way.
Association of the C677T MTHFR Mutation with Schizophrenia, Response to Therapy, and Long-term Outcome
Selection of Patients Nonresponding schizophrenic patients (NR, n=43) were selected from a list of schizophrenic patients identified as candidates for treatment or treated with atypical neuroleptics because of treatment resistance to conventional neuroleptics. Three institutions provided these NR patients: Douglas Hospital, Clinique Jeunes Adultes of L. H. Lafontaine Hospital, and the Schizophrenia Clinic of the Royal Ottawa Hospital. Responding patients (R, n=62) were selected from a list of all patients who were considered very good responders to conventional neuroleptics by their treating physician and/or nurse and who were followed in the outpatient clinics attached to the Douglas and L. H. Lafontaine hospitals, which are the only two university-affiliated psychiatric hospitals for the Montreal intra-muros region.

The following criteria for response or resistance to conventional neuroleptics were used in the selection of NR schizophrenic patients. None of the NR patients had experienced remission of psychotic symptoms within the past two years. In the preceding five years, all NR patients had undergone at least three periods of treatment with conventional neuroleptics from at least two distinct families of drugs at a dose equal to, or greater than, 750 mg chlorpromazine (CPZ) equivalents for monotherapy or 1000 mg CPZ for therapy with a combination of neuroleptics. The treatments, which lasted for a continuous period of at least 6 weeks, resulted in no significant decrease in symptoms. Finally, all patients were unable to function without supervision in all, or nearly all, domains of social and vocational activities and had a Global Assessment Score (GAS) (Endicott et al., Arch. Gen. Psychiatry 33:766–771, 1976) greater than 40 within the last 12 months. Decision for non-response was established by the research psychiatrist upon review of medical records, with particular attention to: (i) unusual thought content, (ii) hallucinations, (iii) conceptual disorganization, (iv) motor retardation, and (v) emotional withdrawal (items 3, 4, 12, 13 and 15 of the Brief Psychiatric Rating Scale; BPRS) (Woerner et al., Psychopharmacol. Bull. 24:112–117, 1988). At the time of enrollment, a minimal score of 4 (moderate to severe) on at least three of the five BPRS items (3, 4, 12, 13, 15), a total BPRS score of at least 45 and/or a CGI (Clinical global Impression) score of at least 5 (markedly ill) were required. These criteria for treatment resistance were derived from those of Kane et al. (Arch. Gen. Psychiatry 45(9):789–96, 1988).

Among the selected R patients, all patients had been admitted at least once to a psychiatric institution because of an acute psychotic episode. During each hospitalization, patients experienced a full or partial remission in response to treatment with conventional neuroleptics within 6 to 8 weeks of continuous treatment. All patients were able to function autonomously with only occasional supervision in all, or nearly all, domains of social and vocational activities. None of the R patients had to be admitted to hospitals because of psychotic exacerbation while under continuous neuroleptic treatment. All R patients had at least one psychotic relapse when neuroleptic medication was reduced or discontinued. Remission was defined as a complete or quasi-complete disappearance of schizophrenic symptoms, with limited residual symptoms, based on the treating psychiatrist clinical evaluation and hospital records. At the time of enrollment, total BPRS scores were less than 30 with no more than one item scoring 4 and/or a CGI score less than 3 (borderline mentally ill).

Both NR and R patients were directly interviewed using the Diagnostic Interview for Genetic Studies (DIGS) (Nurnberger et al., Arch. Gen. Psychiatry 51:849–859, 1994), and their medical records were comprehensively reviewed by a research psychiatrist. Complementary information from the treating physician and nurses in charge was also obtained. The severity of the clinical syndrome at the time of examination was evaluated by the BPRS, and the diagnosis as meeting the criteria for NR or R patients was based on all the available data.

The 90 control patients (C) were determined not to have any DSM-IV axis I mental disorders based on DIGS.

All subjects were Caucasian with a majority (52%) of French Canadians. This project was approved by the Research Ethics Board of each participating institution.

Genetic Analysis

Genomic DNA was isolated from peripheral lymphocytes using standard methods. The target sequence was amplified by PCR using the published procedure of Frosst et al. (Nat. Genet. 10(1):111–113, 1995). PCR products were digested with HinfI because the C677T mutation creates a HinfI recognition sequence. The PCR product of 198 bp was digested into fragments of 175 bp and 23 bp if the C677T mutation was present, while the wild-type (alanine) allele remained undigested (198 bp). The digested PCR products were electrophoresed on 9% polyacrylamide gels and photographed. Genotyping and scoring were performed by someone blinded to the diagnosis.

Statistical Analysis

The allele frequencies in the groups of schizophrenia subjects and controls were compared using a Chi square statistic with one degree of freedom. Because a statistically significant difference between patients and controls was observed in the frequency of allele V, pair-wise comparisons between the three groups of subjects (R, NR, and C) were subsequently conducted. To test for a population bias within the subjects tested, an analysis between the R, NR, and C patients for whom both parents were French Canadian and for whom at least one parent did not have French Canadian ancestry was also performed.

Comparison of Responding, Nonresponding, and Control Groups Based on Frequence of the C677T MTHFR Allele R and NR schizophrenic patients did not differ significantly according to age and gender distributions. Controls were significantly older and included more females than the R and NR groups. In keeping with the study design, the two groups of schizophrenia patients differed significantly according to the severity of psychosis, the percent of time spent as inpatient since their first contact with a psychiatric institution, and their age at first contact with psychiatric care facilities (Table 8).

Allele V was significantly more frequent in schizophrenic patients, regardless of the quality of their response to neuroleptics and long-term outcome, compared to controls ($\chi^2=5.44$, df=1, p=0.019). However, the most striking finding was observed when patients were stratified according to their quality of response to conventional neuroleptics and long-term outcome. The group of R patients showed a highly significant increase in the frequency of allele V ($\chi^2=16.77$, df=1, p=0.00004) in contrast to the group of NR patients ($\chi^2=0.053$, df=1, p=0.81). The odds ratio associated with carrying at least one allele V in the group of responder patients was 6.80 with a 95% confidence interval of 5.22 to 8.87.

The same pattern of differences between responders and controls was observed when subjects with two French Canadian parents ($\chi^2=8.91$, df=1, p=0.002) and those with at least one non-French Canadian parent ($\chi^2=6.71$, df=1, p=0.009) were compared separately;. The similar results observed in both subpopulations compared to the overall tested Caucasian population reduces the likelihood of a population stratification bias in the data. The stratification of the data according to gender resulted in a significant difference in males ($\chi^2=12.63$, df=1, p=0.0003) and a trend in females $\chi^2=2.58$, df=1, p=0.10).

Both dominant (VV+AV vs. AA) and recessive (VV vs. AV+AA) models of transmission of the C677T mutation were tested. For both models, the differences between neuroleptic responder patients and controls were significant for the whole group of patients and for the groups stratified according to background of parents (Table 9). Finally, an ANOVA analysis was performed in which the genotype was the grouping variable and the age-at-onset was the outcome variable. A tendency toward a dose effect of allele V was observed for the age-at-onset (F=2.48, df=(2, 94); p=0.088). The average ages at onset ± (SD) were 19.16 (4.49), 20.91 (5.42) and 22.52 (5.53) for patients with genotypes AA, AV, and VV respectively.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for selecting an efficacious therapy for a subject suffering from a schizophrenia, said method comprising the steps of:
   (a) analyzing the MTHFR nucleic acid in a sample obtained from said subject;
   (b) determining the presence of a heterozygous C/T mutation at position 677 that decreases MTHFR activity or reduces MTHFR thermal dability MTHF in said subject, wherein the presence of said mutation is indicative of the efficacy of a therapy; and
   (c) selecting an efficacious neuroleptic therapy for said subject.

2. The method of claim 1, wherein said nucleic acid with said mutation at position 677 is determined to further comprise an additional mutation selected from the group consisting of: G/A mutation at position 167, a G/A mutation at position 482, a CIT mutation a position 559, a C/T mutation at position 692, a C/T mutation at position 764, a G/A mutation at position 792+1, a C/T mutation at position 985, a CIT mutation at position 1015, a C/T mutation at position 1081, an A/C mutation at position 1298, and a T/C mutation at position 1317, wherein said additional mutation decreases MTHFR activity or reduces MTHFR thermal stability.

3. The method of claim 2, wherein said nucleic acid with said mutation at position 677 comprises an A/C mutation at position 1298.

4. The method of claim 1, wherein said nucleic acid is determined to comprise at least two MTHFR mutations at a position other than 677 that further decrease MTHFR activity or further reduce MTHFR thermal stability.

5. The method of claim 4, wherein said mutations at a position other than 677 comprise at least one of a G/A mutation at position 167, a G/A mutation at position 482, a CIT mutation a position 559, a CIT mutation at position 692, a C/T mutation at position 764, a G/A mutation at position 792+1, a C/T mutation at position 985, a C/T mutation at position 1015, a C/T mutation at position 1081, an A/C mutation at position 1298, or a T/C mutation at position 1317.

6. The method of claim 5, wherein said mutations at a position other than 677 comprise an A/C mutation at position 1298.

7. A method for treating a schizophrenia in a subject, said method comprising the steps of:
   (a) analyzing the MTHFR nucleic acid in a sample obtained from said subject;
   (b) determining the presence of a heterozygous C/T mutation at position 677 that decreases MTHFR activity or reduces MTHFR thermal stability in said subject, wherein the presence of said mutation is predictive of the responsiveness of said schizophrenia to a neuroleptic therapy; and
   (c) administering said neuroleptic therapy to said subject.

8. The method of claim 7, wherein said nucleic acid with said mutation at position 677 further comprises a G/A mutation at position 167, a G/A mutation at position 482, a C/T mutation a position 559, a C/T mutation at position 692, a C/T mutation at position 764, a G/A mutation at position 792+1, a C/T mutation at position 985, a C/T mutation at position 1015, a C/T mutation at position 1081, an A/C mutation at position 1298, or a T/C mutation at position 1317, wherein said additional mutation decreases MTHFR activity or reduces MTHFR thermal stability.

9. The method of claim 8, wherein said nucleic acid with said mutation at position 677 comprises an A/C mutation at position 1298.

10. The method of claim 7, wherein said nucleic acid is determined to comprise at least two mutations at a position other than 677 that further decrease MTHFR activity or further reduce MTHFR thermal stability.

11. The method of claim 10, wherein said mutations at a position other than 677 comprise at least one of a G/A mutation at position 167, a G/A mutation at position 482, a C/T mutation a position 559, a C/T mutation at position 692, a C/T mutation at position 764, a G/A mutation at position 792+1, a C/T mutation at position 985, a C/T mutation at position 1015, a C/T mutation at position 1081, an A/C mutation at position 1298, or a T/C mutation at position 1317.

12. The method of claim 11, wherein said mutations at a position other than 677 comprise an A/C mutation at position 1298.

13. The method of claim 1, A further comprising the step of determining the presence of at least one MTHFR mutation at a position other than 677 prior to step (c) wherein said mutation decreases MTHFR activity or reduces MTHFR thermal stability.

14. The method of claim 7, further comprising determining the presence of at least one MTHFR mutation at a position other than 677 prior to step (c), wherein said additional mutation decreases MTHFR activity or reduces MTHFR thermal stability.

15. The method of claim 1, wherein said step (c) further comprises selecting a folic acid therapy.

16. The method of claim 7, wherein said step (c) further comprises administering a folic acid therapy.

* * * * *

UNITED STATES PATENT AND TRADEMARK OFFICE
CERTIFICATE OF CORRECTION

PATENT NO. : 6,833,243 B2
DATED : December 21, 2004
INVENTOR(S) : Rozen

It is certified that error appears in the above-identified patent and that said Letters Patent is hereby corrected as shown below:

Column 63,
Line 39, replace "MTHF" with -- MTHFR --.
Lines 48 and 51, replace "CIT" with -- C/T --.
Line 66, replace both occurrences of "CIT" with -- C/T --.

Column 65,
Line 6, replace "TIC" with -- T/C --.

Signed and Sealed this

Tenth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,833,243 B2 Page 1 of 1
APPLICATION NO. : 09/931795
DATED : December 21, 2004
INVENTOR(S) : Rima Rozen It is certified that error appears in the above-identified patent and that said Letters Patent is hereby corrected as shown below:

Title Page
In Section (73) Assignee, Replace "Nuvelo, Inc., Sunnyvale, CA (US)" with --McGill University, Montreal, (CA)--.

Signed and Sealed this

Eighth Day of April, 2008

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 2220
<212> TYPE: DNA
<213> ORGANISM: Homo sapiens
<220> FEATURE:
<221> NAME/KEY: CDS
<222> LOCATION: (1)...(1980)

<400> SEQUENCE: 1 aat tcc gga gcc atg gtg aac gaa gcc aga gga aac agc agc ctc aac      48
Asn Ser Gly Ala Met Val Asn Glu Ala Arg Gly Asn Ser Ser Leu Asn
 1               5                  10                  15 ccc tgc ttg gag ggc agt gcc agc agt ggc agt gag agc tcc aaa gat      96
Pro Cys Leu Glu Gly Ser Ala Ser Ser Gly Ser Glu Ser Ser Lys Asp
            20                  25                  30 agt tcg aga tgt tcc acc ccg ggc ctg gac cct gag cgg cat gag aga     144
Ser Ser Arg Cys Ser Thr Pro Gly Leu Asp Pro Glu Arg His Glu Arg
        35                  40                  45 ctc cgg gag aag atg agg cgg cga ttg gaa tct ggt gac aag tgg ttc     192
Leu Arg Glu Lys Met Arg Arg Arg Leu Glu Ser Gly Asp Lys Trp Phe
    50                  55                  60 tcc ctg gaa ttc ttc cct cct cga act gct gag gga gct gtc aat ctc     240
Ser Leu Glu Phe Phe Pro Pro Arg Thr Ala Glu Gly Ala Val Asn Leu
65                  70                  75                  80 atc tca agg ttt gac cgg atg gca gca ggt ggc ccc ctc tac ata gac     288
Ile Ser Arg Phe Asp Arg Met Ala Ala Gly Gly Pro Leu Tyr Ile Asp
                85                  90                  95 gtg acc tgg cac cca gca ggt gac cct ggc tca gac aag gag acc tcc     336
Val Thr Trp His Pro Ala Gly Asp Pro Gly Ser Asp Lys Glu Thr Ser
            100                 105                 110 tcc atg atg atc gcc agc acc gcc gtg aac tac tgt ggc ctg gag acc     384
Ser Met Met Ile Ala Ser Thr Ala Val Asn Tyr Cys Gly Leu Glu Thr
        115                 120                 125 atc ctg cac atg acc tgc tgc cgt cag cgc ctg gag gag atc acg ggc     432
Ile Leu His Met Thr Cys Cys Arg Gln Arg Leu Glu Glu Ile Thr Gly
    130                 135                 140 cat ctg cac aaa gct aag cag ctg ggc ctg aag aac atc atg gcg ctg     480
His Leu His Lys Ala Lys Gln Leu Gly Leu Lys Asn Ile Met Ala Leu
145                 150                 155                 160 cgg gga gac cca ata ggt gac cag tgg gaa gag gag gga ggc ttc       528
Arg Gly Asp Pro Ile Gly Asp Gln Trp Glu Glu Glu Gly Gly Phe
                165                 170                 175 aac tac gca gtg gac ctg gtg aag cac atc cga agt gag ttt ggt gac     576
Asn Tyr Ala Val Asp Leu Val Lys His Ile Arg Ser Glu Phe Gly Asp
            180                 185                 190 tac ttt gac atc tgt gtg gca ggt tac ccc aaa ggc cac ccc gaa gca     624
Tyr Phe Asp Ile Cys Val Ala Gly Tyr Pro Lys Gly His Pro Glu Ala
        195                 200                 205 ggg agc ttt gag gct gac ctg aag cac ttg aag gag aag gtg tct gcg     672
```

-continued

```
                Gly Ser Phe Glu Ala Asp Leu Lys His Leu Lys Glu Lys Val Ser Ala
                    210                 215                 220 gga gcc gat ttc atc atc acg cag ctt ttc ttt gag gct gac aca ttc         720
Gly Ala Asp Phe Ile Ile Thr Gln Leu Phe Phe Glu Ala Asp Thr Phe
225                 230                 235                 240 ttc cgc ttt gtg aag gca tgc acc gac atg ggc atc act tgc ccc atc         768
Phe Arg Phe Val Lys Ala Cys Thr Asp Met Gly Ile Thr Cys Pro Ile
                245                 250                 255 gtc ccc ggg atc ttt ccc atc cag ggc tac cac tcc ctt cgg cag ctt         816
Val Pro Gly Ile Phe Pro Ile Gln Gly Tyr His Ser Leu Arg Gln Leu
            260                 265                 270 gtg aag ctg tcc aag ctg gag gtg cca cag gag atc aag gac gtg att         864
Val Lys Leu Ser Lys Leu Glu Val Pro Gln Glu Ile Lys Asp Val Ile
        275                 280                 285 gag cca atc aaa gac aac gat gct gcc atc cgc aac tat ggc atc gag         912
Glu Pro Ile Lys Asp Asn Asp Ala Ala Ile Arg Asn Tyr Gly Ile Glu
    290                 295                 300 ctg gcc gtg agc ctg tgc cag gag ctt ctg gcc agt ggc ttg gtg cca         960
Leu Ala Val Ser Leu Cys Gln Glu Leu Leu Ala Ser Gly Leu Val Pro
305                 310                 315                 320 ggc ctc cac ttc tac acc ctc aac cgc gag atg gct acc aca gag gtg        1008
Gly Leu His Phe Tyr Thr Leu Asn Arg Glu Met Ala Thr Thr Glu Val
                325                 330                 335 ctg aag cgc ctg ggg atg tgg act gag gac ccc agg cgt ccc cta ccc        1056
Leu Lys Arg Leu Gly Met Trp Thr Glu Asp Pro Arg Arg Pro Leu Pro
                340                 345                 350 tgg gct ctc agt gcc cac ccc aag cgc cga gag gaa gat gta cgt ccc        1104
Trp Ala Leu Ser Ala His Pro Lys Arg Arg Glu Glu Asp Val Arg Pro
            355                 360                 365 atc ttc tgg gcc tcc aga cca aag agt tac atc tac cgt acc cag gag        1152
Ile Phe Trp Ala Ser Arg Pro Lys Ser Tyr Ile Tyr Arg Thr Gln Glu
370                 375                 380 tgg gac gag ttc cct aac ggc cgc tgg ggc aat tcc tct tcc cct gcc        1200
Trp Asp Glu Phe Pro Asn Gly Arg Trp Gly Asn Ser Ser Ser Pro Ala
385                 390                 395                 400 ttt ggg gag ctg aag gac tac tac ctc ttc tac ctg aag agc aag tcc        1248
Phe Gly Glu Leu Lys Asp Tyr Tyr Leu Phe Tyr Leu Lys Ser Lys Ser
                405                 410                 415 ccc aag gag gag ctg ctg aag atg tgg ggg gag gag ctg acc agt gaa        1296
Pro Lys Glu Glu Leu Leu Lys Met Trp Gly Glu Glu Leu Thr Ser Glu
                420                 425                 430 gca agt gtc ttt gaa gtc ttt gtt ctt tac ctc tcg gga gaa cca aac        1344
Ala Ser Val Phe Glu Val Phe Val Leu Tyr Leu Ser Gly Glu Pro Asn
            435                 440                 445 cgg aat ggt cac aaa gtg act tgc ctg ccc tgg aac gat gag ccc ctg        1392
Arg Asn Gly His Lys Val Thr Cys Leu Pro Trp Asn Asp Glu Pro Leu
        450                 455                 460 gcg gct gag acc agc ctg ctg aag gag gag ctg ctg cgg gtg aac cgc        1440
Ala Ala Glu Thr Ser Leu Leu Lys Glu Glu Leu Leu Arg Val Asn Arg
465                 470                 475                 480 cag ggc atc ctc acc atc aac tca cag ccc aac atc aac ggg aag ccg        1488
Gln Gly Ile Leu Thr Ile Asn Ser Gln Pro Asn Ile Asn Gly Lys Pro
                485                 490                 495 tcc tcc gac ccc atc gtg ggc tgg ggc ccc agc ggg ggc tat gtc ttc        1536
Ser Ser Asp Pro Ile Val Gly Trp Gly Pro Ser Gly Gly Tyr Val Phe
                500                 505                 510 cag aag gcc tac tta gag ttt ttc act tcc cgc gag aca gcg gaa gca        1584
Gln Lys Ala Tyr Leu Glu Phe Phe Thr Ser Arg Glu Thr Ala Glu Ala
            515                 520                 525
```

-continued

```
ctt ctg caa gtg ctg aag aag tac gag ctc cgg gtt aat tac cac ctt   1632
Leu Leu Gln Val Leu Lys Lys Tyr Glu Leu Arg Val Asn Tyr His Leu
        530                 535                 540 gtc aat gtg aag ggt gaa aac atc acc aat gcc cct gaa ctg cag ccg   1680
Val Asn Val Lys Gly Glu Asn Ile Thr Asn Ala Pro Glu Leu Gln Pro
545                 550                 555                 560 aat gct gtc act tgg ggc atc ttc cct ggg cga gag atc atc cag ccc   1728
Asn Ala Val Thr Trp Gly Ile Phe Pro Gly Arg Glu Ile Ile Gln Pro
                565                 570                 575 acc gta gtg gat ccc gtc agc ttc atg ttc tgg aag gac gag gcc ttt   1776
Thr Val Val Asp Pro Val Ser Phe Met Phe Trp Lys Asp Glu Ala Phe
            580                 585                 590 gcc ctg tgg att gag cgg tgg gga aag ctg tat gag gag gag tcc ccg   1824
Ala Leu Trp Ile Glu Arg Trp Gly Lys Leu Tyr Glu Glu Glu Ser Pro
        595                 600                 605 tcc cgc acc atc atc cag tac atc cac gac aac tac ttc ctg gtc aac   1872
Ser Arg Thr Ile Ile Gln Tyr Ile His Asp Asn Tyr Phe Leu Val Asn
610                 615                 620 ctg gtg gac aat gac ttc cca ctg gac aac tgc ctc tgg cag gtg gtg   1920
Leu Val Asp Asn Asp Phe Pro Leu Asp Asn Cys Leu Trp Gln Val Val
625                 630                 635                 640 gaa gac aca ttg gag ctt ctc aac agg ccc acc cag aat gcg aga gaa   1968
Glu Asp Thr Leu Glu Leu Leu Asn Arg Pro Thr Gln Asn Ala Arg Glu
                645                 650                 655 acg gag gct cca tgaccctgcg tcctgacgcc ctgcgttgga gccactcctg       2020
Thr Glu Ala Pro
            660 tcccgccttc ctcctccaca gtgctgcttc tcttgggaac tccactctcc ttcgtgtctc   2080 tcccaccccg gcctccactc ccccacctga caatggcagc tagactggag tgaggcttcc   2140 aggctcttcc tggacctgag tcggccccac atgggaacct agtactctct gctctaaaaa   2200 aaaaaaaaaa aaaggaattc                                              2220

<210> SEQ ID NO 2
<211> LENGTH: 660
<212> TYPE: PRT
<213> ORGANISM: Homo sapiens

<400> SEQUENCE: 2

Asn Ser Gly Ala Met Val Asn Glu Ala Arg Gly Asn Ser Ser Leu Asn
1               5                   10                  15

Pro Cys Leu Glu Gly Ser Ala Ser Gly Ser Glu Ser Ser Lys Asp
            20                  25                  30

Ser Ser Arg Cys Ser Thr Pro Gly Leu Asp Pro Glu Arg His Glu Arg
        35                  40                  45

Leu Arg Glu Lys Met Arg Arg Leu Glu Ser Gly Asp Lys Trp Phe
    50                  55                  60

Ser Leu Glu Phe Phe Pro Pro Arg Thr Ala Glu Gly Ala Val Asn Leu
65                  70                  75                  80

Ile Ser Arg Phe Asp Arg Met Ala Ala Gly Gly Pro Leu Tyr Ile Asp
                85                  90                  95

Val Thr Trp His Pro Ala Gly Asp Pro Gly Ser Asp Lys Glu Thr Ser
            100                 105                 110

Ser Met Met Ile Ala Ser Thr Ala Val Asn Tyr Cys Gly Leu Glu Thr
        115                 120                 125

Ile Leu His Met Thr Cys Cys Arg Gln Arg Leu Glu Glu Ile Thr Gly
    130                 135                 140
```

-continued

```
His Leu His Lys Ala Lys Gln Leu Gly Leu Lys Asn Ile Met Ala Leu
145                 150                 155                 160

Arg Gly Asp Pro Ile Gly Asp Gln Trp Glu Glu Glu Gly Gly Phe
                165                 170                 175

Asn Tyr Ala Val Asp Leu Val Lys His Ile Arg Ser Glu Phe Gly Asp
            180                 185                 190

Tyr Phe Asp Ile Cys Val Ala Gly Tyr Pro Lys Gly His Pro Glu Ala
        195                 200                 205

Gly Ser Phe Glu Ala Asp Leu Lys His Leu Lys Glu Lys Val Ser Ala
    210                 215                 220

Gly Ala Asp Phe Ile Ile Thr Gln Leu Phe Phe Glu Ala Asp Thr Phe
225                 230                 235                 240

Phe Arg Phe Val Lys Ala Cys Thr Asp Met Gly Ile Thr Cys Pro Ile
                245                 250                 255

Val Pro Gly Ile Phe Pro Ile Gln Gly Tyr His Ser Leu Arg Gln Leu
            260                 265                 270

Val Lys Leu Ser Lys Leu Glu Val Pro Gln Glu Ile Lys Asp Val Ile
        275                 280                 285

Glu Pro Ile Lys Asp Asn Asp Ala Ala Ile Arg Asn Tyr Gly Ile Glu
    290                 295                 300

Leu Ala Val Ser Leu Cys Gln Glu Leu Leu Ala Ser Gly Leu Val Pro
305                 310                 315                 320

Gly Leu His Phe Tyr Thr Leu Asn Arg Glu Met Ala Thr Thr Glu Val
                325                 330                 335

Leu Lys Arg Leu Gly Met Trp Thr Glu Asp Pro Arg Arg Pro Leu Pro
            340                 345                 350

Trp Ala Leu Ser Ala His Pro Lys Arg Glu Glu Asp Val Arg Pro
        355                 360                 365

Ile Phe Trp Ala Ser Arg Pro Lys Ser Tyr Ile Tyr Arg Thr Gln Glu
    370                 375                 380

Trp Asp Glu Phe Pro Asn Gly Arg Trp Gly Asn Ser Ser Pro Ala
385                 390                 395                 400

Phe Gly Glu Leu Lys Asp Tyr Tyr Leu Phe Tyr Leu Lys Ser Lys Ser
                405                 410                 415

Pro Lys Glu Glu Leu Leu Lys Met Trp Gly Glu Glu Leu Thr Ser Glu
            420                 425                 430

Ala Ser Val Phe Glu Val Phe Val Leu Tyr Leu Ser Gly Glu Pro Asn
        435                 440                 445

Arg Asn Gly His Lys Val Thr Cys Leu Pro Trp Asn Asp Glu Pro Leu
    450                 455                 460

Ala Ala Glu Thr Ser Leu Leu Lys Glu Glu Leu Leu Arg Val Asn Arg
465                 470                 475                 480

Gln Gly Ile Leu Thr Ile Asn Ser Gln Pro Asn Ile Asn Gly Lys Pro
                485                 490                 495

Ser Ser Asp Pro Ile Val Gly Trp Gly Pro Ser Gly Gly Tyr Val Phe
            500                 505                 510

Gln Lys Ala Tyr Leu Glu Phe Phe Thr Ser Arg Glu Thr Ala Glu Ala
        515                 520                 525

Leu Leu Gln Val Leu Lys Lys Tyr Glu Leu Arg Val Asn Tyr His Leu
    530                 535                 540

Val Asn Val Lys Gly Glu Asn Ile Thr Asn Ala Pro Glu Leu Gln Pro
545                 550                 555                 560

Asn Ala Val Thr Trp Gly Ile Phe Pro Gly Arg Glu Ile Ile Gln Pro
```

-continued

```
                        565                 570                 575
Thr Val Val Asp Pro Val Ser Phe Met Phe Trp Lys Asp Glu Ala Phe
            580                 585                 590
Ala Leu Trp Ile Glu Arg Trp Gly Lys Leu Tyr Glu Glu Ser Pro
        595                 600                 605
Ser Arg Thr Ile Ile Gln Tyr Ile His Asp Asn Tyr Phe Leu Val Asn
    610                 615                 620
Leu Val Asp Asn Asp Phe Pro Leu Asp Asn Cys Leu Trp Gln Val Val
625                 630                 635                 640
Glu Asp Thr Leu Glu Leu Leu Asn Arg Pro Thr Gln Asn Ala Arg Glu
                645                 650                 655
Thr Glu Ala Pro
            660

<210> SEQ ID NO 3
<211> LENGTH: 2219
<212> TYPE: DNA
<213> ORGANISM: Homo sapiens
<220> FEATURE:
<221> NAME/KEY: CDS
<222> LOCATION: (13)...(1983)

<400> SEQUENCE: 3
aattccggag cc atg gtg aac gaa gcc aga gga aac agc agc ctc aac ccc    51
              Met Val Asn Glu Ala Arg Gly Asn Ser Ser Leu Asn Pro
                1               5                   10 tgc ttg gag ggc agt gcc agc agt ggc agt gag agc tcc aaa gat agt     99
Cys Leu Glu Gly Ser Ala Ser Ser Gly Ser Glu Ser Ser Lys Asp Ser
 15                  20                  25 tcg aga tgt tcc acc ccg ggc ctg gac cct gag cgg cat gag aga ctc    147
Ser Arg Cys Ser Thr Pro Gly Leu Asp Pro Glu Arg His Glu Arg Leu
 30                  35                  40                  45 cgg gag aag atg agg cgg cga ttg gaa tct ggt gac aag tgg ttc tcc    195
Arg Glu Lys Met Arg Arg Arg Leu Glu Ser Gly Asp Lys Trp Phe Ser
                 50                  55                  60 ctg gaa ttc ttc cct cct cga act gct gag gga gct gtc aat ctc atc    243
Leu Glu Phe Phe Pro Pro Arg Thr Ala Glu Gly Ala Val Asn Leu Ile
             65                  70                  75 tca agg ttt gac cgg atg gca gca ggt ggc ccc ctc tac ata gac gtg    291
Ser Arg Phe Asp Arg Met Ala Ala Gly Gly Pro Leu Tyr Ile Asp Val
         80                  85                  90 acc tgg cac cca gca ggt gac cct ggc tca gac aag gag acc tcc tcc    339
Thr Trp His Pro Ala Gly Asp Pro Gly Ser Asp Lys Glu Thr Ser Ser
     95                  100                 105 atg atg atc gcc agc acc gcc gtg aac tac tgt ggc ctg gag acc atc    387
Met Met Ile Ala Ser Thr Ala Val Asn Tyr Cys Gly Leu Glu Thr Ile
110                 115                 120                 125 ctg cac atg acc tgc tgc cgt cag cgc ctg gag gag atc acg ggc cat    435
Leu His Met Thr Cys Cys Arg Gln Arg Leu Glu Glu Ile Thr Gly His
                130                 135                 140 ctg cac aaa gct aag cag ctg ggc ctg aag aac atc atg gcg ctg cgg    483
Leu His Lys Ala Lys Gln Leu Gly Leu Lys Asn Ile Met Ala Leu Arg
            145                 150                 155 gga gac cca ata ggt gac cag tgg gaa gag gag gag gga ggc ttc aac    531
Gly Asp Pro Ile Gly Asp Gln Trp Glu Glu Glu Glu Gly Gly Phe Asn
        160                 165                 170 tac gca gtg gac ctg gtg aag cac atc cga agt gag ttt ggt gac tac    579
Tyr Ala Val Asp Leu Val Lys His Ile Arg Ser Glu Phe Gly Asp Tyr
    175                 180                 185
```

-continued

| | | |
|---|---|---|
| ttt gac atc tgt gtg gca ggt tac ccc aaa ggc cac ccc gaa gca ggg<br>Phe Asp Ile Cys Val Ala Gly Tyr Pro Lys Gly His Pro Glu Ala Gly<br>190                         195                    200                   205 | 627 |
| agc ttt gag gct gac ctg aag cac ttg aag gag aag gtg tct gcg gga<br>Ser Phe Glu Ala Asp Leu Lys His Leu Lys Glu Lys Val Ser Ala Gly<br>                      210                    215                   220 | 675 |
| gcc gat ttc atc atc acg cag ctt ttc ttt gag gct gac aca ttc ttc<br>Ala Asp Phe Ile Ile Thr Gln Leu Phe Phe Glu Ala Asp Thr Phe Phe<br>225                         230                    235 | 723 |
| cgc ttt gtg aag gca tgc acc gac atg ggc atc act tgc ccc atc gtc<br>Arg Phe Val Lys Ala Cys Thr Asp Met Gly Ile Thr Cys Pro Ile Val<br>     240                   245                   250 | 771 |
| ccc ggg atc ttt ccc atc cag ggc tac cac tcc ctt cgg cag ctt gtg<br>Pro Gly Ile Phe Pro Ile Gln Gly Tyr His Ser Leu Arg Gln Leu Val<br>255                         260                    265 | 819 |
| aag ctg tcc aag ctg gag gtg cca cag gag atc aag gac gtg att gag<br>Lys Leu Ser Lys Leu Glu Val Pro Gln Glu Ile Lys Asp Val Ile Glu<br>270                         275                    280                   285 | 867 |
| cca atc aaa gac aac gat gct gcc atc cgc aac tat ggc atc gag ctg<br>Pro Ile Lys Asp Asn Asp Ala Ala Ile Arg Asn Tyr Gly Ile Glu Leu<br>                      290                    295                   300 | 915 |
| gcc gtg agc ctg tgc cag gag ctt ctg gcc agt ggc ttg gtg cca ggc<br>Ala Val Ser Leu Cys Gln Glu Leu Leu Ala Ser Gly Leu Val Pro Gly<br>            305                    310                   315 | 963 |
| ctc cac ttc tac acc ctc aac cgc gag atg gct acc aca gag gtg ctg<br>Leu His Phe Tyr Thr Leu Asn Arg Glu Met Ala Thr Thr Glu Val Leu<br>                    320                    325                   330 | 1011 |
| aag cgc ctg ggg atg tgg act gag gac ccc agg cgt ccc cta ccc tgg<br>Lys Arg Leu Gly Met Trp Thr Glu Asp Pro Arg Arg Pro Leu Pro Trp<br>335                         340                    345 | 1059 |
| gct ctc agt gcc cac ccc aag cgc cga gag gaa gat gta cgt ccc atc<br>Ala Leu Ser Ala His Pro Lys Arg Arg Glu Glu Asp Val Arg Pro Ile<br>350                         355                    360                   365 | 1107 |
| ttc tgg gcc tcc aga cca aag agt tac atc tac cgt acc cag gag tgg<br>Phe Trp Ala Ser Arg Pro Lys Ser Tyr Ile Tyr Arg Thr Gln Glu Trp<br>                      370                    375                   380 | 1155 |
| gac gag ttc cct aac ggc cgc tgg ggc aat tcc tct tcc cct gcc ttt<br>Asp Glu Phe Pro Asn Gly Arg Trp Gly Asn Ser Ser Ser Pro Ala Phe<br>            385                    390                   395 | 1203 |
| ggg gag ctg aag gac tac tac ctc ttc tac ctg aag agc aag tcc ccc<br>Gly Glu Leu Lys Asp Tyr Tyr Leu Phe Tyr Leu Lys Ser Lys Ser Pro<br>                    400                    405                   410 | 1251 |
| aag gag gag ctg ctg aag atg tgg ggg gag gag ctg acc agt gaa gca<br>Lys Glu Glu Leu Leu Lys Met Trp Gly Glu Glu Leu Thr Ser Glu Ala<br>415                         420                    425 | 1299 |
| agt gtc ttt gaa gtc ttt gtt ctt tac ctc tcg gga gaa cca aac cgg<br>Ser Val Phe Glu Val Phe Val Leu Tyr Leu Ser Gly Glu Pro Asn Arg<br>430                         435                    440                   445 | 1347 |
| aat ggt cac aaa gtg act tgc ctg ccc tgg aac gat gag ccc ctg gcg<br>Asn Gly His Lys Val Thr Cys Leu Pro Trp Asn Asp Glu Pro Leu Ala<br>                         450                    455                   460 | 1395 |
| gct gag acc agc ctg ctg aag gag gag ctg ctg cgg gtg aac cgc cag<br>Ala Glu Thr Ser Leu Leu Lys Glu Glu Leu Leu Arg Val Asn Arg Gln<br>                    465                    470                   475 | 1443 |
| ggc atc ctc acc atc aac tca cag ccc aac atc aac ggg aag ccg tcc<br>Gly Ile Leu Thr Ile Asn Ser Gln Pro Asn Ile Asn Gly Lys Pro Ser<br>                      480                    485                   490 | 1491 |
| tcc gac ccc atc gtg ggc tgg ggc ccc agc ggg ggc tat gtc ttc cag<br>Ser Asp Pro Ile Val Gly Trp Gly Pro Ser Gly Gly Tyr Val Phe Gln<br>                         495                    500                   505 | 1539 |

```
aag gcc tac tta gag ttt ttc act tcc cgc gag aca gcg gaa gca ctt    1587
Lys Ala Tyr Leu Glu Phe Phe Thr Ser Arg Glu Thr Ala Glu Ala Leu
510                 515                 520                 525 ctg caa gtg ctg aag aag tac gag ctc cgg gtt aat tac cac ctt gtc    1635
Leu Gln Val Leu Lys Lys Tyr Glu Leu Arg Val Asn Tyr His Leu Val
                530                 535                 540 aat gtg aag ggt gaa aac atc acc aat gcc cct gaa ctg cag ccg aat    1683
Asn Val Lys Gly Glu Asn Ile Thr Asn Ala Pro Glu Leu Gln Pro Asn
            545                 550                 555 gct gtc act tgg ggc atc ttc cct ggg cga gag atc atc cag ccc acc    1731
Ala Val Thr Trp Gly Ile Phe Pro Gly Arg Glu Ile Ile Gln Pro Thr
        560                 565                 570 gta gtg gat ccc gtc agc ttc atg ttc tgg aag gac gag gcc ttt gcc    1779
Val Val Asp Pro Val Ser Phe Met Phe Trp Lys Asp Glu Ala Phe Ala
    575                 580                 585 ctg tgg att gag cgg tgg gga aag ctg tat gag gag gag tcc ccg tcc    1827
Leu Trp Ile Glu Arg Trp Gly Lys Leu Tyr Glu Glu Glu Ser Pro Ser
590                 595                 600                 605 cgc acc atc atc cag tac atc cac gac aac tac ttc ctg gtc aac ctg    1875
Arg Thr Ile Ile Gln Tyr Ile His Asp Asn Tyr Phe Leu Val Asn Leu
                610                 615                 620 gtg gac aat gac ttc cca ctg gac aac tgc ctc tgg cag gtg gtg gaa    1923
Val Asp Asn Asp Phe Pro Leu Asp Asn Cys Leu Trp Gln Val Val Glu
            625                 630                 635 gac aca ttg gag ctt ctc aac agg ccc acc cag aat gcg aga gaa acg    1971
Asp Thr Leu Glu Leu Leu Asn Arg Pro Thr Gln Asn Ala Arg Glu Thr
        640                 645                 650 gag gct cca tga ccctgcgtcc tgacgccctg cgttggagcc actcctgtcc        2023
Glu Ala Pro  *
    655 cgccttcctc ctccacagtg ctgcttctct tgggaactcc actctccttc gtgtctctcc  2083 cacccccggcc tccactcccc cacctgacaa tggcagctag actggagtga ggcttccagg 2143 ctcttcctgg acctgagtcg gccccacatg ggaacctagt actctctgct ctaaaaaaaa  2203 aaaaaaaaaa ggaatt                                                   2219

<210> SEQ ID NO 4
<211> LENGTH: 656
<212> TYPE: PRT
<213> ORGANISM: Homo sapiens

<400> SEQUENCE: 4

Met Val Asn Glu Ala Arg Gly Asn Ser Ser Leu Asn Pro Cys Leu Glu
1               5                   10                  15

Gly Ser Ala Ser Ser Gly Ser Glu Ser Ser Lys Asp Ser Ser Arg Cys
            20                  25                  30

Ser Thr Pro Gly Leu Asp Pro Glu Arg His Glu Arg Leu Arg Glu Lys
        35                  40                  45

Met Arg Arg Arg Leu Glu Ser Gly Asp Lys Trp Phe Ser Leu Glu Phe
    50                  55                  60

Phe Pro Pro Arg Thr Ala Glu Gly Ala Val Asn Leu Ile Ser Arg Phe
65                  70                  75                  80

Asp Arg Met Ala Ala Gly Gly Pro Leu Tyr Ile Asp Val Thr Trp His
                85                  90                  95

Pro Ala Gly Asp Pro Gly Ser Asp Lys Glu Thr Ser Ser Met Met Ile
            100                 105                 110

Ala Ser Thr Ala Val Asn Tyr Cys Gly Leu Glu Thr Ile Leu His Met
```

-continued

```
                115                 120                 125
Thr Cys Cys Arg Gln Arg Leu Glu Glu Ile Thr Gly His Leu His Lys
130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Gly Phe Asn Tyr Ala Val
                165                 170                 175

Asp Leu Val Lys His Ile Arg Ser Glu Phe Gly Asp Tyr Phe Asp Ile
                180                 185                 190

Cys Val Ala Gly Tyr Pro Lys Gly His Pro Glu Ala Gly Ser Phe Glu
                195                 200                 205

Ala Asp Leu Lys His Leu Lys Glu Lys Val Ser Ala Gly Ala Asp Phe
210                 215                 220

Ile Ile Thr Gln Leu Phe Phe Glu Ala Asp Thr Phe Phe Arg Phe Val
225                 230                 235                 240

Lys Ala Cys Thr Asp Met Gly Ile Thr Cys Pro Ile Val Pro Gly Ile
                245                 250                 255

Phe Pro Ile Gln Gly Tyr His Ser Leu Arg Gln Leu Val Lys Leu Ser
                260                 265                 270

Lys Leu Glu Val Pro Gln Glu Ile Lys Asp Val Ile Glu Pro Ile Lys
                275                 280                 285

Asp Asn Asp Ala Ala Ile Arg Asn Tyr Gly Ile Glu Leu Ala Val Ser
                290                 295                 300

Leu Cys Gln Glu Leu Leu Ala Ser Gly Leu Val Pro Gly Leu His Phe
305                 310                 315                 320

Tyr Thr Leu Asn Arg Glu Met Ala Thr Thr Glu Val Leu Lys Arg Leu
                325                 330                 335

Gly Met Trp Thr Glu Asp Pro Arg Arg Pro Leu Pro Trp Ala Leu Ser
                340                 345                 350

Ala His Pro Lys Arg Arg Glu Glu Asp Val Arg Pro Ile Phe Trp Ala
                355                 360                 365

Ser Arg Pro Lys Ser Tyr Ile Tyr Arg Thr Gln Glu Trp Asp Glu Phe
370                 375                 380

Pro Asn Gly Arg Trp Gly Asn Ser Ser Ser Pro Ala Phe Gly Glu Leu
385                 390                 395                 400

Lys Asp Tyr Tyr Leu Phe Tyr Leu Lys Ser Lys Ser Pro Lys Glu Glu
                405                 410                 415

Leu Leu Lys Met Trp Gly Glu Glu Leu Thr Ser Glu Ala Ser Val Phe
                420                 425                 430

Glu Val Phe Val Leu Tyr Leu Ser Gly Glu Pro Asn Arg Asn Gly His
                435                 440                 445

Lys Val Thr Cys Leu Pro Trp Asn Asp Glu Pro Leu Ala Ala Glu Thr
450                 455                 460

Ser Leu Leu Lys Glu Glu Leu Leu Arg Val Asn Arg Gln Gly Ile Leu
465                 470                 475                 480

Thr Ile Asn Ser Gln Pro Asn Ile Asn Gly Lys Pro Ser Ser Asp Pro
                485                 490                 495

Ile Val Gly Trp Gly Pro Ser Gly Gly Tyr Val Phe Gln Lys Ala Tyr
                500                 505                 510

Leu Glu Phe Phe Thr Ser Arg Glu Thr Ala Glu Ala Leu Leu Gln Val
                515                 520                 525

Leu Lys Lys Tyr Glu Leu Arg Val Asn Tyr His Leu Val Asn Val Lys
530                 535                 540
```

```
Gly Glu Asn Ile Thr Asn Ala Pro Glu Leu Gln Pro Asn Ala Val Thr
545                 550                 555                 560

Trp Gly Ile Phe Pro Gly Arg Glu Ile Ile Gln Pro Thr Val Val Asp
                565                 570                 575

Pro Val Ser Phe Met Phe Trp Lys Asp Glu Ala Phe Ala Leu Trp Ile
            580                 585                 590

Glu Arg Trp Gly Lys Leu Tyr Glu Glu Ser Pro Ser Arg Thr Ile
        595                 600                 605

Ile Gln Tyr Ile His Asp Asn Tyr Phe Leu Val Asn Leu Val Asp Asn
    610                 615                 620

Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
                645                 650                 655

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
agcctcaacc cctgcttgga gg                                           22

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
tgacagtttg ctccccaggc ac                                           22

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
tgaaggagaa ggtgtctgcg gga                                          23

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
aggacggtgc ggtgagagtg g                                            21

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
```

```
cactgtggtt ggcatggatg atg                                               23

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
ggctgctctt ggaccctcct c                                                 21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
tgcttccggc tccctctagc c                                                 21

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
cctcccgctc ccaagaacaa ag                                                22

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
tgaaggagaa ggtgtctgcg gga                                               23

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
aggacggtgc ggtgagagtg                                                   20

<210> SEQ ID NO 15
<211> LENGTH: 21
<212> TYPE: DNA
<213> ORGANISM: Artificial Sequence
<220> FEATURE:
<223> OTHER INFORMATION: Synthetic Primer

<400> SEQUENCE: 15
gggaggagct gaccagtgca g                                                 21

<210> SEQ ID NO 16
<211> LENGTH: 19
<212> TYPE: DNA
```

-continued

```
<213> ORGANISM: Artificial Sequence
<220> FEATURE:
<223> OTHER INFORMATION: Synthetic Primer

<400> SEQUENCE: 16
ggggtcaggc cagggcag                                              19

<210> SEQ ID NO 17
<211> LENGTH: 23
<212> TYPE: DNA
<213> ORGANISM: Artificial Sequence
<220> FEATURE:
<223> OTHER INFORMATION: Synthetic Primer

<400> SEQUENCE: 17
ggttctcccg agaggtaaag atc                                        23

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
ctggggatgt ggtggcactg c                                          21
```